(12) United States Patent
Dunbar et al.

(10) Patent No.: US 12,338,488 B2
(45) Date of Patent: Jun. 24, 2025

(54) LOGIC DRIVEN POLYNUCLEOTIDE SCANNING FOR MAPPING FEATURES IN A NANOPORE DEVICE

(71) Applicant: Nooma Bio, Inc., Santa Cruz, CA (US)

(72) Inventors: William B. Dunbar, Santa Cruz, CA (US); Xu Liu, Santa Cruz, CA (US)

(73) Assignee: Oxford Nanopore Technologies plc, Oxford (GB)

( * ) Notice: Subject to any disclaimer, the term of this patent is extended or adjusted under 35 U.S.C. 154(b) by 720 days.

(21) Appl. No.: 17/665,349

(22) Filed: Feb. 4, 2022

(65) Prior Publication Data

US 2022/0282312 A1 Sep. 8, 2022

Related U.S. Application Data

(63) Continuation of application No. PCT/US2020/045257, filed on Aug. 6, 2020.

(60) Provisional application No. 63/003,129, filed on Mar. 31, 2020, provisional application No. 62/962,838, filed on Jan. 17, 2020, provisional application No. 62/883,449, filed on Aug. 6, 2019.

(51) Int. Cl.
*C12Q 1/6825* (2018.01)
*C12Q 1/6869* (2018.01)
*G01N 27/447* (2006.01)
*G01N 33/487* (2006.01)

(52) U.S. Cl.
CPC ......... *C12Q 1/6825* (2013.01); *C12Q 1/6869* (2013.01); *G01N 27/44791* (2013.01); *G01N 33/48721* (2013.01)

(58) Field of Classification Search
CPC ............... C12Q 1/6825; C12Q 1/6827; C12Q 1/6869; C12Q 2563/116; C12Q 2565/607; C12Q 2565/629; C12Q 2565/631; G01N 27/44791; G01N 33/48721
See application file for complete search history.

(56) References Cited

U.S. PATENT DOCUMENTS

| 7,731,826 B2 * | 6/2010 | Hibbs ................. C12Q 1/6869 |
| | | 435/6.19 |
| 8,273,532 B2 | 9/2012 | Gershow et al. |
| 2009/0136958 A1 | 5/2009 | Gershow et al. |

(Continued)

FOREIGN PATENT DOCUMENTS

| JP | 2014-074599 A | 4/2014 |
| WO | WO 2017/145239 A1 | 8/2017 |
| WO | WO 2018/236673 A1 | 12/2018 |

OTHER PUBLICATIONS

Gershow, M. et al. "Recapturing and Trapping Single Molecules with a Solid State Nanopore." Author Manuscript, Nature Nanotechnology, vol. 2, No. 12, Dec. 2007, pp. 775-779.

(Continued)

*Primary Examiner* — Jennifer Wecker
(74) *Attorney, Agent, or Firm* — Fenwick & West LLP

(57) ABSTRACT

The present disclosure provides an automated method of mapping one or more features of a target polynucleotide. Also provided in the present disclosure are automated methods for sequencing a polynucleotide sequence. Also provided in the present disclosure are methods of extended recapture of a polynucleotide in a nanopore device. Also provided in the present disclosure are devices and systems for carrying out the methods of the present disclosure.

22 Claims, 43 Drawing Sheets

Specification includes a Sequence Listing.

(56) References Cited

U.S. PATENT DOCUMENTS

| | | |
|---|---|---|
| 2015/0160160 A1 | 6/2015 | Dunbar et al. |
| 2015/0283514 A1* | 10/2015 | Aguilar ............... B01D 67/009 156/182 |
| 2016/0216234 A1 | 7/2016 | Stein et al. |
| 2017/0145481 A1 | 5/2017 | Kim et al. |
| 2019/0022647 A1 | 1/2019 | Aoki et al. |
| 2019/0136307 A1 | 5/2019 | Predki et al. |

OTHER PUBLICATIONS

Liu, X. et al. "Controlling DNA Tug-of-War in a Dual Nanopore Device." Small, vol. 15, No. 30, Jul. 26, 2019, pp. 1-33.
Liu, X. et al. "Entropic Cages for Trapping DNA Near a Nanopore." Nature Communications, vol. 6, Article 6222, Feb. 4, 2015, pp. 1-9.
Liu, X. et al. "Flossing DNA in a Dual Nanopore Chip." Supplementary Material, Small, vol. 16, No. 3, Jan. 23, 2020, pp. 1-24.
Liu, X. et al. "Flossing DNA in a Dual Nanopore Device." Small, vol. 16, No. 3, Jan. 23, 2020, pp. 1-11.
PCT International Search Report and Written Opinion, PCT Application No. PCT/US2020/045257, Nov. 9, 2020, 16 pages.
Zhang, Y. et al. "Single Molecule DNA Resensing Using a Two-Pore Devise." Small, vol. 14, No. 47, Nov. 22, 2018, pp. 1-11.

* cited by examiner

FIG. 3
Single Pore Testing
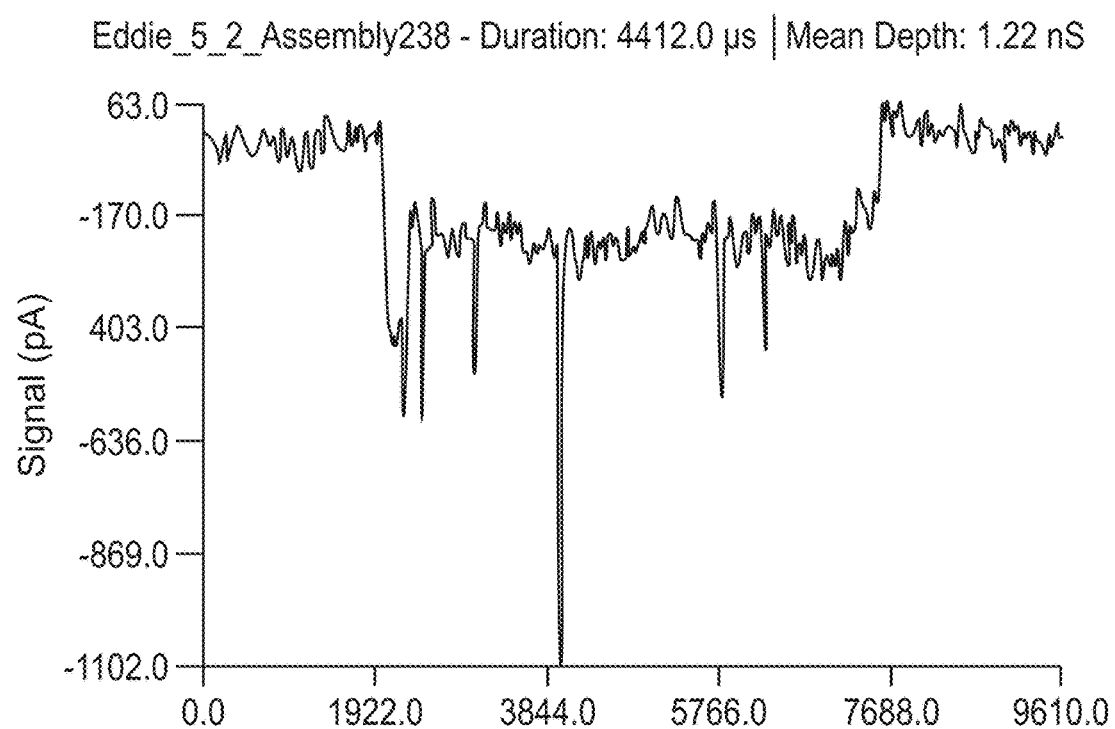
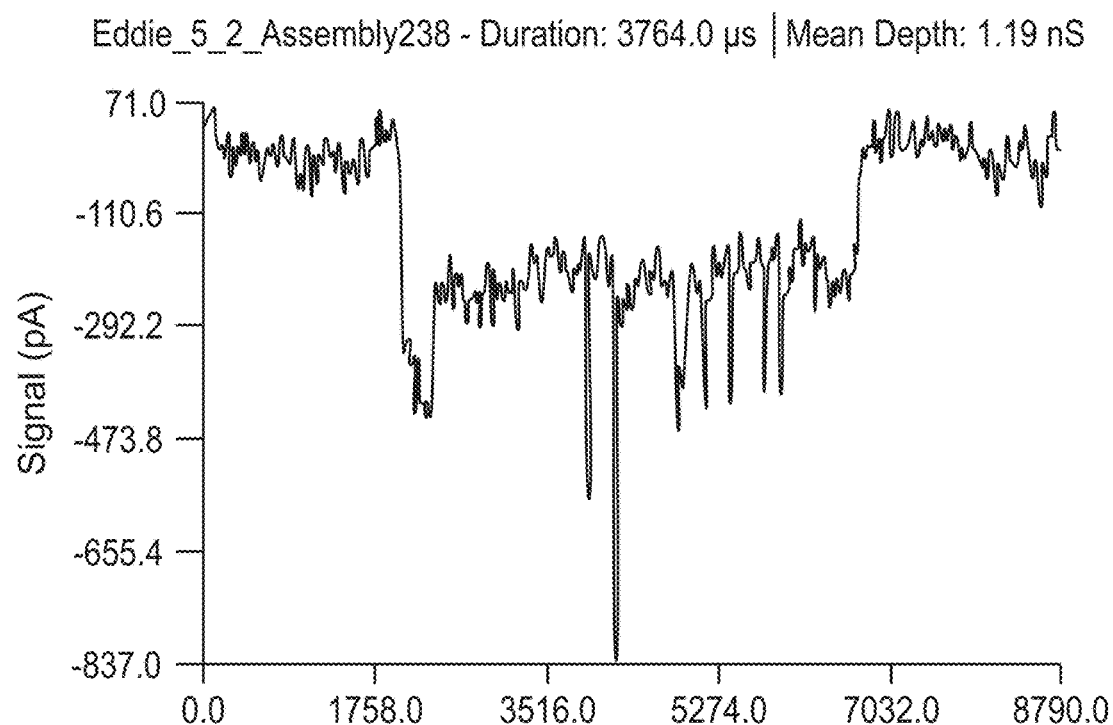

FIG. 3 (Cont.)
Single Pore Testing
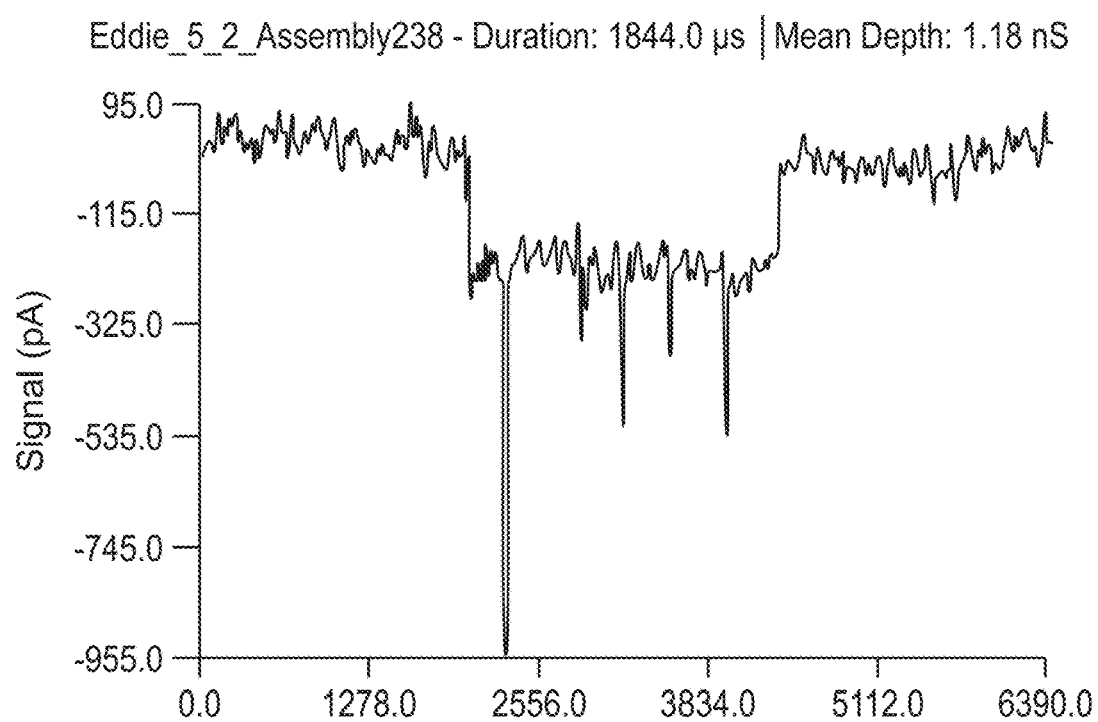
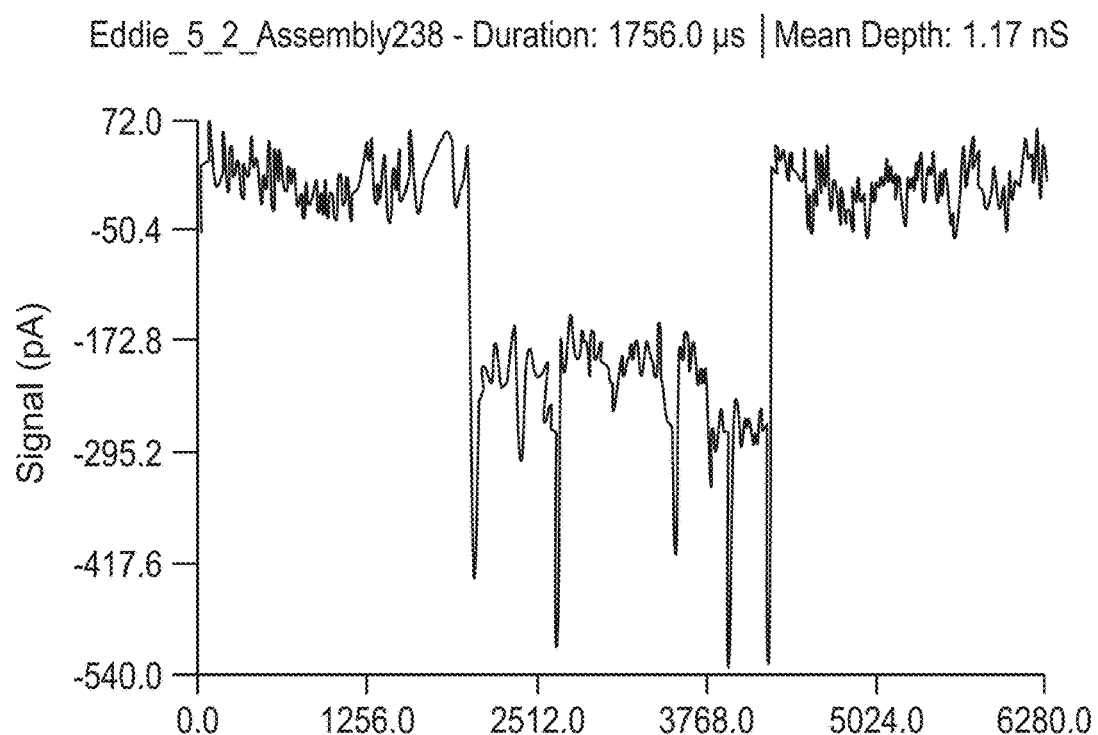

Single Pore Testing

State Signal Meaning

FIG. 8 (Cont.)
f
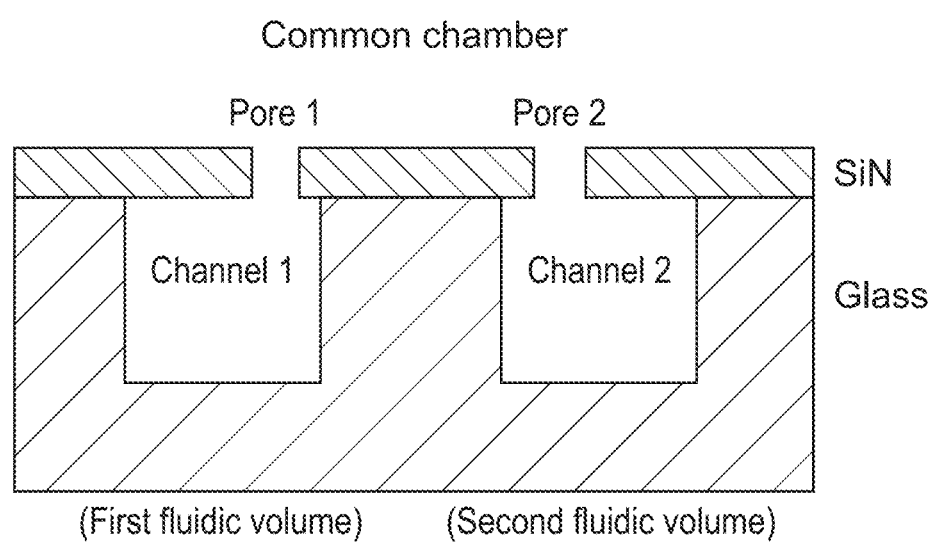
g
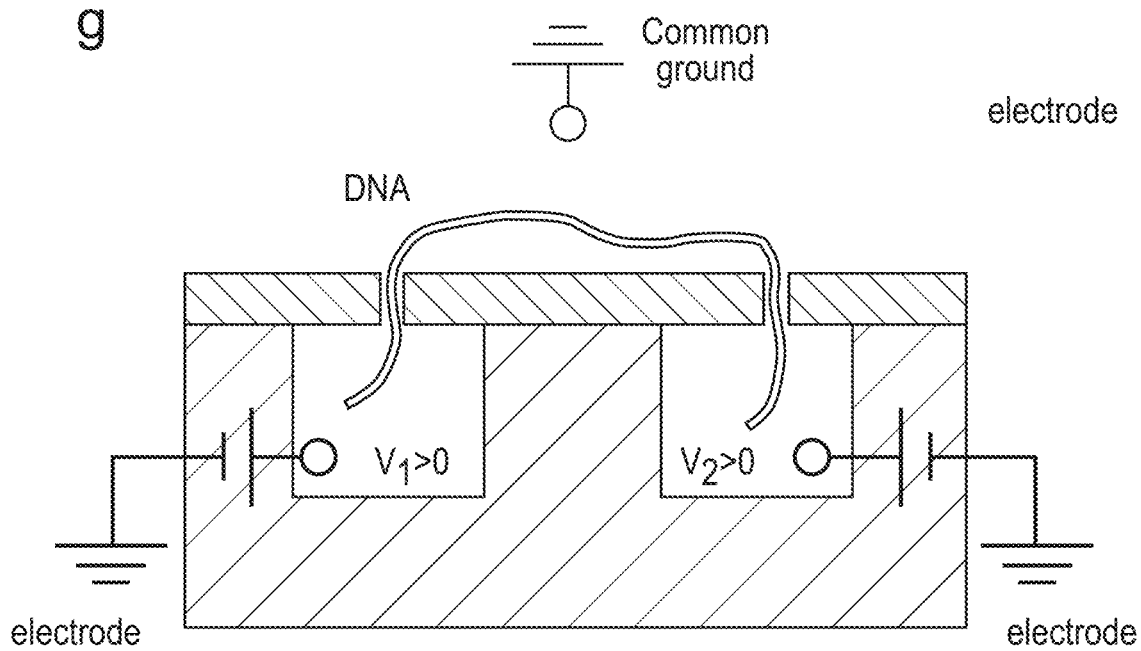
Zhang, et al. Small

FIG. 11
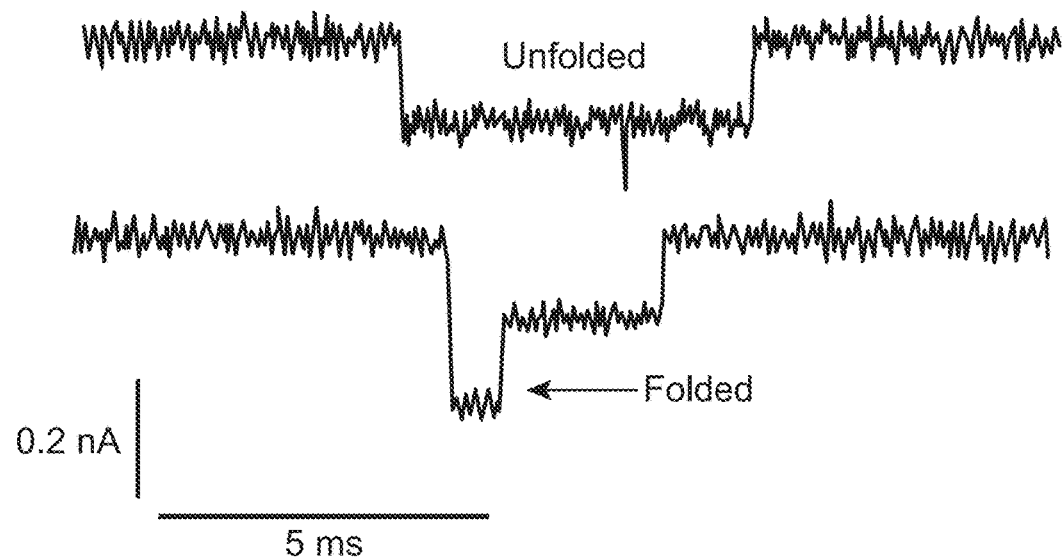
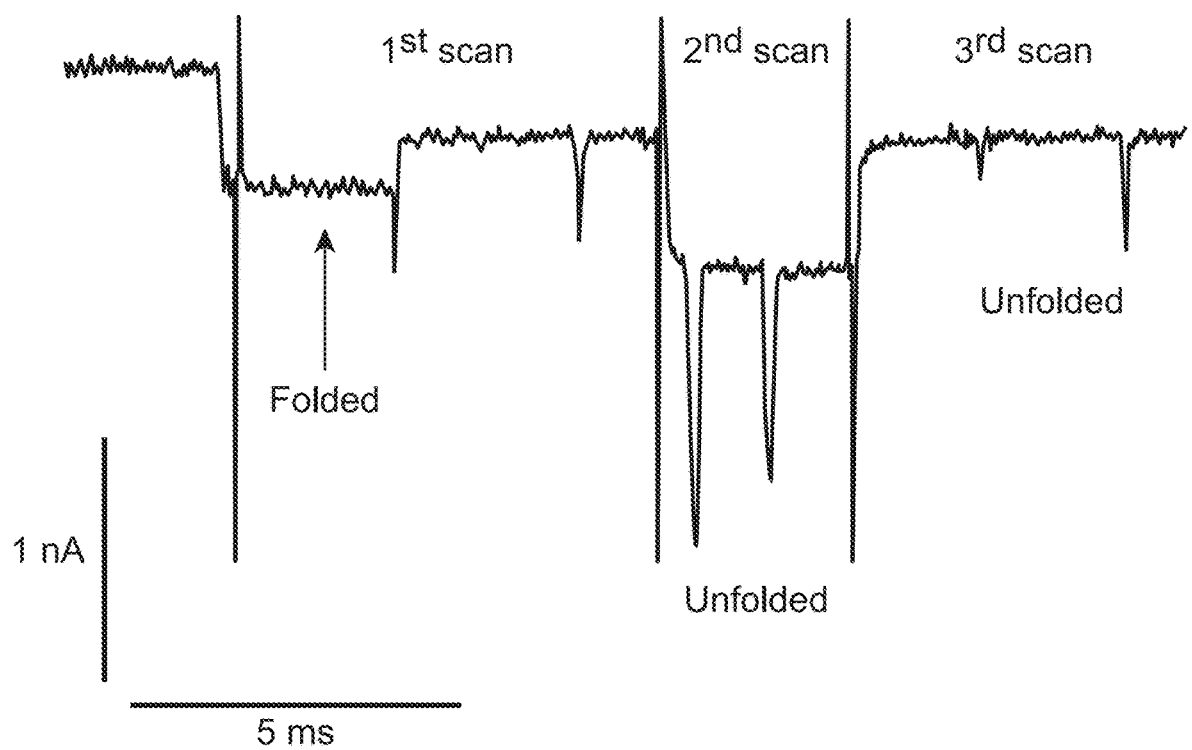

FIG. 11 (Cont.)
c
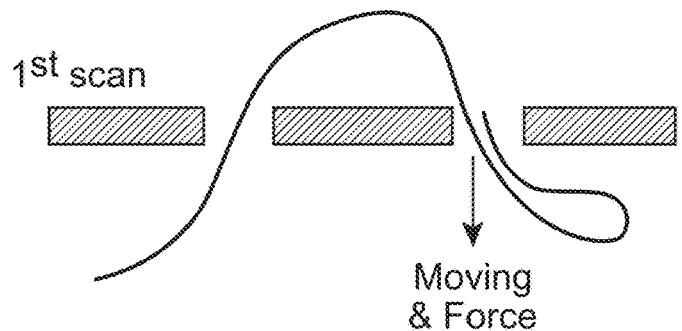
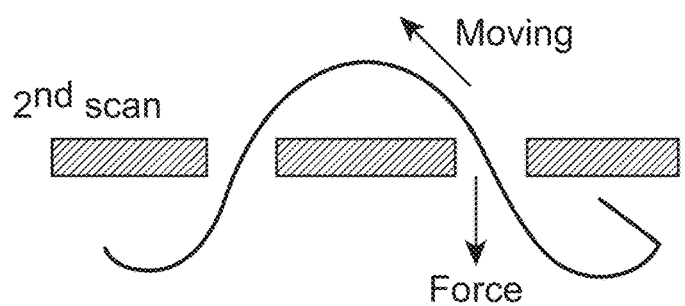
d
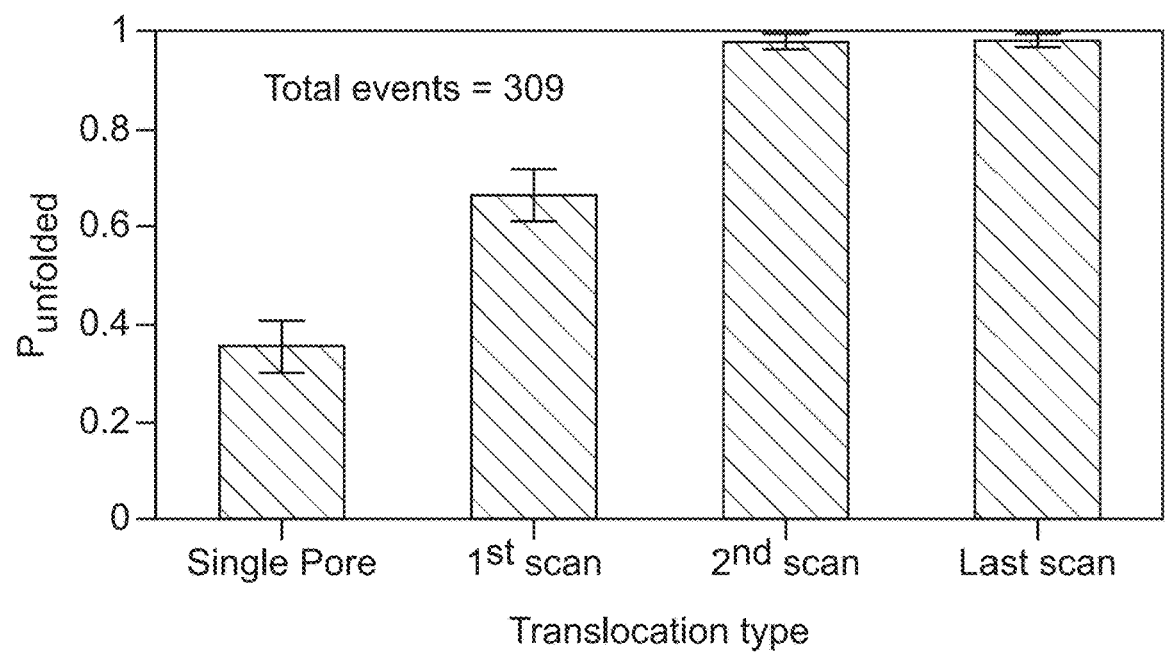

FIG. 13

| Event [a] | Number of cycles | Scan direction | Pore 2 tag-to-tag separation [μm] [b] | Combined tag-to-tag separations [μm] [b] |
|---|---|---|---|---|
| (i) [c] | 48 | R-to-L | a. 0.10 ± 0.005 (32)<br>b. - (0) | a. 0.12 ± 0.006 (56)<br>b. 1.4 ± 0.031 (21) |
| (ii) | 30 | L-to-R<br>R-to-L | 1.5 ± 0.12 (28)<br>1.5 ± 0.026 (15) | 1.5 ± 0.12 (48)<br>1.5 ± 0.017 (38) |
| (iii) | 70 | L-to-R<br>R-to-L | 1.3 ± 0.045 (68)<br>1.4 ± 0.017 (32) | 1.3 ± 0.034 (116)<br>1.3 ± 0.011 (96) |
| (iv) | 31 | L-to-R<br>R-to-L | 0.31 ± 0.022 (9)<br>0.3 ± 0.005 (28) | 0.31 ± 0.022 (9)<br>0.31 ± 0.004 (55) |
| (v) | 65 | L-to-R<br>R-to-L | 0.2 ± 0.008 (18)<br>0.21 ± 0.003 (57) | 0.2 ± 0.009 (20)<br>0.21 ± 0.002 (119) | a) Events (i-iiii) and (iv)-(v) are from chips E and F (Table S1), respectively.

b) Mean ± standard deviation of the mean (number of samples).

c) Three tags were detected to produce two adjacent separations, listed as (a) and (b). L-to-R results had larger errors due to larger pore-to-pore speed fluctuation (coefficient of variation is 83%, Table S3), and so were excluded.

FIG. 21

| Event & No., Cycles# | Scan Dir.‡ | Entry Tag Speed (μm/ms)† | Exit Tag Speed (μm/ms)† | Pore-to-Pore Speed (μm/ms)† | Pore 2 Tag-to-Tag Separations (μm)* | Combined Tag-to-Tag Separations (μm)* |
|---|---|---|---|---|---|---|
| (i), 48 | L-to-R | 0.86 ± 0.18 (72) | 0.65 ± 0.21 (101) | 0.35 ± 0.29 (41) | a.0.074 ± 0.0068 (23) b.0.77 ± 0.046 (2) | a.0.073 ± 0.0051 (39) b.1 ± 0.078 (17) |
| | R-to-L | 0.92 ± 0.25 (94) | 0.75 ± 0.33 (88) | 0.81 ± 0.16 (57) | a.0.1 ± 0.0049 (32) b. — (0) | a.0.12 ± 0.0063 (56) b.1.4 ± 0.031 (21) |
| (ii), 27 | L-to-R | 0.63 ± 0.19 (27) | 0.82 ± 0.21 (48) | 0.73 ± 0.22 (26) | 6.6 ± 0.28 (21) | 6.6 ± 0.25 (24) |
| | R-to-L | 0.77 ± 0.26 (41) | 0.81 ± 0.26 (27) | 0.81 ± 0.15 (27) | 9.3 ± 0.77 (20) | 8.9 ± 0.62 (26) |
| (iii), 30 | L-to-R | 0.64 ± 0.19 (50) | 0.43 ± 0.21 (60) | 0.48 ± 0.25 (49) | 1.5 ± 0.12 (28) | 1.5 ± 0.12 (48) |
| | R-to-L | 1.2 ± 0.22 (39) | 0.82 ± 0.19 (47) | 1.2 ± 0.15 (38) | 1.5 ± 0.026 (15) | 1.5 ± 0.017 (38) |
| (iv), 70 | L-to-R | 0.53 ± 0.21 (118) | 0.52 ± 0.21 (138) | 0.54 ± 0.17 (118) | 1.3 ± 0.045 (68) | 1.3 ± 0.034 (116) |
| | R-to-L | 0.94 ± 0.3 (102) | 0.76 ± 0.22 (134) | 1.1 ± 0.17 (99) | 1.4 ± 0.017 (32) | 1.3 ± 0.011 (96) |
| (v), 38 | L-to-R | 0.51 ± 0.24 (74) | 0.66 ± 0.24 (92) | 1.2 ± 0.2 (73) | a.0.23 ± 0.0087 (38) b.1.0 ± 0.078 (13) | a.0.24 ± 0.0057 (72) b.1.0 ± 0.078 (13) |
| (vi), 24 | L-to-R | 0.19 ± 0.14 (39) | 0.6 ± 0.19 (47) | 0.46 ± 0.14 (35) | a.4 ± 0.1 (9) b.5.2 ± 0.038 (9) | a.4 ± 0.073 (17) b.5.2 ± 0.038 (9) |
| (vii), 11 | L-to-R | 0.13 ± 0.094 (23) | 0.62 ± 0.15 (22) | 0.41 ± 0.11 (21) | 1.4 ± 0.036 (8) | 1.4 ± 0.024 (16) |
| (viii), 31 | L-to-R | 0.91 ± 0.3 (12) | 0.75 ± 0.12 (22) | 0.93 ± 0.41 (12) | 0.31 ± 0.022 (9) | 0.31 ± 0.022 (9) |
| | R-to-L | 0.94 ± 0.16 (58) | 0.76 ± 0.12 (57) | 0.99 ± 0.19 (56) | 0.3 ± 0.005 (28) | 0.31 ± 0.0039 (55) |
| (ix), 65 | L-to-R | 0.68 ± 0.19 (38) | 0.66 ± 0.2 (74) | 0.71 ± 0.25 (38) | 0.2 ± 0.0083 (18) | 0.2 ± 0.009 (20) |
| | R-to-L | 0.96 ± 0.17 (122) | 0.79 ± 0.15 (128) | 0.95 ± 0.16 (121) | 0.21 ± 0.0025 (57) | 0.21 ± 0.0021 (119) |

\# Events (i-iv), (v), (vi-vii) and (viii)-(ix) are from common chips E, G, A and F (Table S1), respectively.
‡ R-to-L not reported where an insufficient number of tags were detected.
† Mean ± standard deviation (count). No data was trimmed.
\* Mean ± standard deviation of the mean (count). One or two (a,b) separations are reported where two or three tags, respectively, were reliably detected.

Channel Geometry

Channel Resistance $$R = \frac{1}{2} \cdot \frac{1}{\sigma} \cdot \frac{L}{s} = \frac{1}{2\sigma \cdot 1.5\,\mu m} \cdot \frac{L}{W-100} \cdot \ln\frac{W}{100}$$

For 2 M LiCl: $\sigma = 12.2\,S/m$

Nanopore: $R = \frac{1}{\sigma} \cdot \frac{4L}{\pi d^2 + 1/d} = 2.7\,M\Omega$

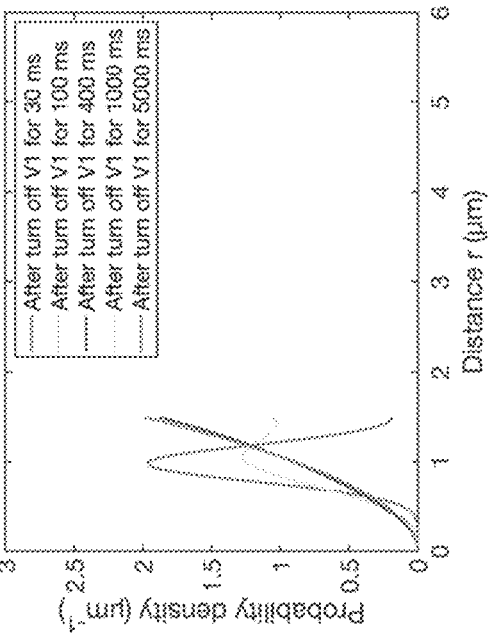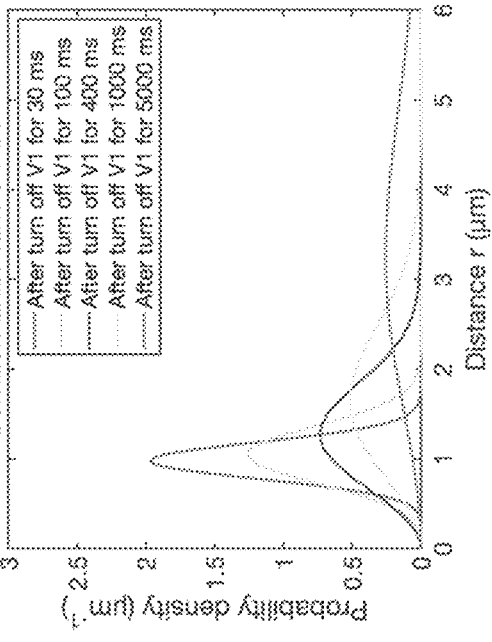
FIG. 28

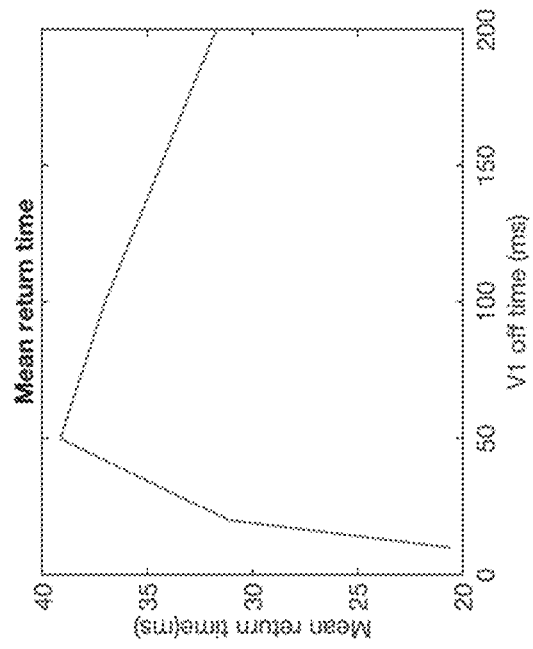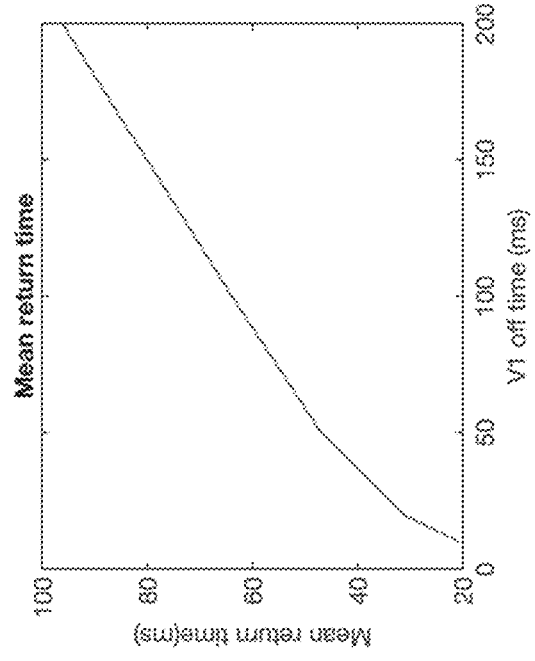
FIG. 29

LOGIC DRIVEN POLYNUCLEOTIDE SCANNING FOR MAPPING FEATURES IN A NANOPORE DEVICE

CROSS-REFERENCE

This application is a continuation of PCT/US2020/045257, filed on Aug. 6, 2020, which claims priority benefit to U.S. Provisional Patent Application Nos. 63/003,129, filed Mar. 31, 2020; 62/962,838 filed on Jan. 17, 2020; and 62/883,449, filed on Aug. 6, 2019, each of which applications are incorporated herein by reference in their entirety.

SEQUENCE LISTING

The instant application contains a Sequence Listing, which has been submitted via EFS-Web and is hereby incorporated by reference in its entirety. Said ASCII copy, created on Feb. 2, 2022, is named 51706 US_CRF_sequencelisting.txt, and is 4,096 bytes in size.

INTRODUCTION

Precise mapping of the binding position of molecular motifs along, individual dsDNA strands in highly heterogeneous samples is core to a wide range of genomics applications "beyond" sequencing. One candidate approach for molecular feature mapping is based on measuring modulations in the ionic current arising when a double stranded DNA (dsDNA) is electrically driven through a solid-state nanopore (ss-nanopore). Nanopores are attractive as they have a purely electrical read-out, leading to a small footprint and substantial cost reductions. There is (1) a need for consistent linearization of translocating molecules, (2) need to reduce effect of molecular fluctuations that introduce random error and (3) need to develop strategies to perform accurate genomic distance calibration.

SUMMARY

The present disclosure provides an automated method of mapping one or more features of a target polynucleotide. Also provided in the present disclosure are automated methods for sequencing a polynucleotide sequence. Also provided in the present disclosure are methods of extended recapture of a polynucleotide in a nanopore device. Also provided in the present disclosure are devices and systems for carrying out the methods of the present disclosure.

Aspects of the present disclosure a method for partially or fully recapturing a polynucleotide in a nanopore device that was previously captured, the method comprising: a) providing a device with at least one nanopore, the device comprising: (i) a first pore positioned between, and fluidically connecting, a chamber and a first fluidic volume, the first fluidic volume being a geometrically constrained enclosure, (ii) the first fluidic volume comprising an inlet and an outlet for fluidic filling and electrode access, wherein the first pore is connected to the first fluidic volume in a location in between the inlet and outlet, (iii) at least one electrode positioned within the first fluidic volume, and at least one electrode positioned within the chamber, (iv) a sensor configured to provide: a voltage between the electrode within the first fluidic volume and the electrode within the chamber, and a current measurement that detects capture and translocation of the polynucleotide into and through the first pore; b) loading the polynucleotide into the chamber of the device; c) applying a first voltage to capture and translocate the polynucleotide from the chamber in a first direction through the first pore and into the first fluidic volume; d) detecting in a first sensor current when the polynucleotide has translocated through the first pore in the first direction; e) applying a second voltage equal to zero mV for a time period while the polynucleotide is contained within the first fluidic volume; 0 applying a third voltage to recapture and partially or fully translocate the polynucleotide from the first fluidic volume through the first pore and into the chamber; and g) detecting in the first sensor current when the polynucleotide has partially or fully translocated through the first pore.

In some embodiments, the nanopore device further comprises a second pore.

In some embodiments, the first fluidic volume is a fluidic channel.

In some embodiments, the polynucleotide exhibits a minimum time duration during said detecting step (d) that it was captured and translocated through the first pore prior to executing step (e), as an indication that the polynucleotide is above a minimum length.

In some embodiments, the polynucleotide is identified as a target when the minimum time duration is longer than a threshold, and identified as a non-target when the time duration is shorter than the threshold.

In some embodiments, said detecting in step (d) that the polynucleotide was captured and translocated through the first pore at the first voltage, maintaining the first voltage for a time period ranging from 30 ms to 500 ms or longer.

In some embodiments, the second voltage equal to zero in step (e) is maintained for a time period ranging from 10 ms to 5 sec or longer.

In some embodiments, the second voltage equal to zero in step (e) is maintained for a time period sufficient to allow the molecule to entropically relax to an equilibrium configuration.

In some embodiments, the first end of the polynucleotide is positioned away from the at least first pore at a distance ranging from 5 microns to 5 millimeters or more.

In some embodiments, the second end of the polynucleotide is positioned away from the at least first pore at a distance ranging from 2 microns to 5 millimeters or more.

In some embodiments, the method further comprises repeating steps c) through g).

In some embodiments, the chamber is positioned above the at least first pore.

In some embodiments, the chamber is connected to a common ground relative to the first voltage.

In some embodiments, the nanopore device further comprises a second pore.

In some embodiments, the second pore is fluidically connected to a second fluidic volume, wherein the second fluidic volume being a geometrically constrained enclosure with a second inlet and a second outlet, and the second pore is fluidically connected to the second fluidic volume between the inlet and the outlet.

In some embodiments, the second fluidic volume is a second fluidic channel.

In some embodiments, the second pore is connected to the chamber and the second fluidic volume.

In some embodiments, the chamber is positioned above the first and second pore.

In some embodiments, the first voltage is applied between the first fluidic volume and the chamber.

In some embodiments, the nanopore device comprises at least one electrode positioned within the second fluidic volume, wherein the at least one electrode is configured to provide a voltage at the at second pore that is independently controllable from the voltage at the first pore.

In some embodiments, the nanopore device comprises dual-amplifier electronics configured for voltage control and current measurement at the first pore and the second pore.

In some embodiments, the method further comprises, detecting a second sensor current.

In some embodiments, the method further comprises, after detecting the second sensor current, adjusting the first voltage at the first pore and setting a first voltage at the second pore so that at least a portion of the polynucleotide moves through the first pore and the second pore.

In some embodiments, the first voltage at the second pore is higher than the first voltage at the first pore.

In some embodiments, the first voltage at the second pore is higher than the third voltage at the first pore.

In some embodiments, the third voltage is higher than the first voltage.

In some embodiments, the second voltage is 0 mV.

In some embodiments, the first voltage ranges from 50-900 mV.

In some embodiments, the first voltage ranges from 50-900 mV.

In some embodiments, the third voltage ranges from 50-900 mV.

In some embodiments, the first voltage at the second pore ranges from 50-900 mV.

In some embodiments, the first voltage at the first pore, the third voltage at the first pore, and the first voltage at the second pore independently ranges from 50 mV to 900 mV in magnitude.

In some embodiments, the first fluidic volume being a geometrically constrained enclosure is on a side opposite of the first pore. In some embodiments, the second fluidic volume being a geometrically constrained enclosure is on a side opposite of the second pore.

In some embodiments, the polynucleotide is substantially linearized. In some embodiments, the polynucleotide is substantially linearized by the action of the adjustments to the first voltage, the second voltage, the third voltage, or a combination thereof.

In some embodiments, said polynucleotide moves in a second direction in step f), wherein the second direction being from the first fluidic volume through the first pore.

In some embodiments, the method further comprises adjusting the third voltage at the first pore, the first voltage at the second pore, or both, to change the direction of the polynucleotide so that at least a portion of the polynucleotide moves from the second pore through the first pore in the first direction.

In some embodiments, said adjusting the third voltage at the first pore, the first voltage at the second pore, or both, so that at least a portion of the polynucleotide moves in the first direction and/or second direction is repeated for a period of time ranging from 30 ms to 5 minutes or longer until the polynucleotide exits the device.

In some embodiments, the first voltage is applied between the chamber and the second fluidic volume of the device.

In some embodiments, the first voltage is applied during a time period ranging from 30 ms to 500 ms or longer.

In some embodiments, the method further comprises detecting a first set of features on the polynucleotide when the polynucleotide is in both pores in the first direction.

In some embodiments, the method further comprises detecting a second set of features on the polynucleotide when the polynucleotide is in both pores simultaneously in the second direction.

In some embodiments, the method comprises adjusting the first voltage so that the polynucleotide moves through the first pore for a time period ranging from 30 ms to 500 ms or longer.

In some embodiments, the polynucleotide passes through the first pore, the chamber, and the second pore.

In some embodiments, the method further comprises detecting a third sensor current at the first pore and a fourth second current at the second pore when the polynucleotide is in both pores in the first or second direction.

In some embodiments, the method further comprises detecting a fifth sensor current at the first pore and a sixth sensor current at the second pore when the polynucleotide is in both pores in the first or second direction.

In some embodiments, the first voltage creates voltage gradient across the first pore and along the length of the first fluidic volume.

In some embodiments, the third voltage creates voltage gradient across the at second pore and along the length of the second fluidic volume.

In some embodiments, the resistance of the first fluidic channel is inversely proportional to the first fluidic channel width.

In some embodiments, the resistance of the second fluidic channel is inversely proportional to the second fluidic channel width.

In some embodiments, the resistance of the first fluidic channel and/or the second fluidic channel is proportional to the volume of the first fluidic channel and/or second fluidic channel.

In some embodiments, the resistance of the first fluidic channel and/or second fluidic channel is proportional to the volume of the first fluidic channel and/or second fluidic channel.

In some embodiments, the resistance of the first fluidic channel and/or second fluidic channel is proportional to the radius of the first fluidic channel and/or second fluidic channel.

In some embodiments, the resistance of the first fluidic channel and/or second fluidic channel is proportional to the cross-sectional radius of the first fluidic channel and/or second fluidic channel.

In some embodiments, the polynucleotide is substantially linearized.

In some embodiments, the polynucleotide is substantially linearized by the action of the adjustments to the first voltage, the second voltage, the third voltage, or the combination of the first voltage, the second voltage, and the third voltage.

In some embodiments, the method further comprises controlling, with a controller, when the polynucleotide requires rescanning of the one or more features of the polynucleotide for a second or third time.

In some embodiments, the first fluidic channel and/or second fluidic channel comprises a geometrically constrained volume.

In some embodiments, the controller determines which of the one or more features of the polynucleotide to perform additional recapturing of the one or more features in the first direction and/or the second direction.

In some embodiments, the method further comprises moving away from one or more features of the polynucleotide already recaptured.

In some embodiments, the first voltage, the second voltage, and the third voltage range from 0 mV to 1000 mV.

In some embodiments, the first voltage, the second voltage, and the third voltage range from 0 mV to 100 mV.

In some embodiments, the first voltage, the second voltage, and the third voltage range from 100 mV to 200 mV.

In some embodiments, the first voltage, the second voltage, and the third voltage range from 200 mV to 300 mV.

In some embodiments, the first voltage, the second voltage, and the third voltage range from 300 mV to 400 mV.

In some embodiments, the first voltage, the second voltage, and the third voltage range from 400 mV to 500 mV.

In some embodiments, the first voltage to the first pore is lower than the second voltage.

In some embodiments, the first voltage to the first pore is higher than the second voltage.

In some embodiments, the first voltage to the first pore and the second voltage to the second pore are the same.

In some embodiments, the first voltage to the first pore and the second voltage to the first pore are the same in the first direction.

In some embodiments, the first voltage to the first pore is lower than the second voltage to the first pore in the second direction.

In some embodiments, the first voltage to the first pore is lower than the third voltage to the second pore in the third direction.

In some embodiments, the first voltage to the first pore is higher than the third voltage to the second pore in the fourth direction.

In some embodiments, the method further comprises controlling the direction of the polynucleotide through the first and/or second pore via a controller, a processor, and a non-transitory computer-readable medium comprising instructions that cause the processor to: change the direction of the polynucleotide.

In some embodiments, the processor comprises a field programmable gate array (FPGA) or an application-specific integrated circuit (ASIC).

In some embodiments, the controller comprises a field programmable gate array (FPGA) or an application-specific integrated circuit (ASIC).

In some embodiments, the controller is a microcontroller.

In some embodiments, said recapturing provides for detection of the polynucleotide comprising a polynucleotide sequence with a length ranging from 300 base pairs to about 3,000,000 base pairs.

In some embodiments, the first fluidic channel and/or second fluidic channel has a length ranging from about 0.05 mm to about 8 mm from the inlet to the outlet.

In some embodiments, the first fluidic channel and/or second fluidic channel has a width ranging from 20-500 µm.

In some embodiments, the first fluidic channel and/or the second fluidic channel has a depth ranging from 0.5 µm to about 2 µm.

In some embodiments, the sensor is further configured to provide: a voltage between the said electrode within the second fluidic volume and said electrode within the chamber, and a current measurement that detects capture and translocation of the polynucleotide into and through the first pore and second pore.

In some embodiments, the length of the polynucleotide is at least 3 2 times, at least 3 times, at least 4 times, or at least 5 times the distance between the first pore and the second pore, between the chamber and the first fluidic volume, and/or between the chamber and the second fluidic volume.

In some embodiments, the first voltage is maintained for a time period ranging from 0-1000 milliseconds, 0-20 milliseconds, 20-50 seconds, 50-100 seconds, 100-500 seconds, or 500-1000 seconds.

In some embodiments, the first voltage is maintained for a time period ranging from 20 ms or more, 50 ms or more, 120 ms or more, 150 ms or more, 300 ms or more, 500 ms or more, 1000 milliseconds or more, 20 seconds or more, 60 seconds or more, 120 seconds or more, 150 seconds or more, 300 seconds or more, 500 seconds or more, or 1000 seconds or more.

In some embodiments, the first voltage is maintained for the time period after capture and translocation of the target polynucleotide through the first pore.

Aspects of the present disclosure include a method for mapping one or more features of a target polynucleotide, the method comprising the steps of: a) providing a device for controlling the movement of the target polynucleotide through a first and second pore simultaneously, the device comprising: (i) a first pore positioned between, and fluidically connecting, a chamber and a first fluidic volume, the first fluidic volume being a geometrically constrained enclosure, (ii) a second pore positioned between, and fluidically connecting, the chamber and a second fluidic volume, the second fluidic volume being a geometrically constrained enclosure; (iii) the first fluidic volume and the second fluidic volume, each comprising an inlet and an outlet for fluidic filling and electrode access, wherein the first pore is connected to the geometrically constrained enclosure of the first fluidic volume in a location in between the inlet and outlet, and wherein the second pore is connected to the geometrically constrained enclosure of the second fluidic volume in a location in between the inlet and outlet, (iv) at least one electrode positioned within the first fluidic volume, at least one electrode positioned within the second fluidic volume, and at least one electrode positioned within the chamber, (v) a sensor configured to provide: a voltage between the said electrode within the first fluidic volume and said electrode within the chamber; a voltage between the said electrode within the second fluidic volume and said electrode within the chamber, and a current measurement that detects capture and partial or full translocation of the polynucleotide into and through the first pore; and a current measurement that detects capture and partial or full translocation of the polynucleotide into and through the second pore; b) loading the target polynucleotide into the chamber of the device; c) applying a first voltage at the first pore and a first voltage at the second pore to capture and translocate the target polynucleotide through the first pore and into the first fluidic volume; d) applying a second voltage at the first pore and a second voltage at the second pore to recapture and partially or fully translocate the target polynucleotide from the first fluidic volume through the first pore; e) applying a third voltage at the first pore, and a third voltage at the second pore so that at least a portion of the target polynucleotide is captured by the second pore while remaining in the first pore; f) applying a fourth voltage at the first pore and a fourth voltage at the second pore to control the direction of motion of the target polynucleotide; and g) detecting in a first sensor current, a first set of features on the polynucleotide, as each feature passes through the first pore and again in a second sensor current as each feature passes through the second pore.

In some embodiments, the method further comprises h) applying a fifth voltage at the first pore and a fifth voltage at the second pore to reverse the direction of motion of the target polynucleotide; and i) detecting in the second sensor current, a second set of features in the polynucleotide, as each feature passes through the second pore and again in the first sensor current as each feature passes through the first pore.

In some embodiments, the first fluidic volume being a geometrically constrained enclosure is on a side opposite of the first pore. In some embodiments, the second fluidic volume being a geometrically constrained enclosure is on a side opposite of the second pore.

In some embodiments, the chamber is positioned above the first and second pores of the device.

In some embodiments, the third voltage at the second pore in step (e) is greater than the third voltage at the first pore.

In some embodiments, the third voltage at the first pore in step (e) is 0 mV.

In some embodiments, the target polynucleotide in step (d) is partially translocated from the first fluidic volume through the first pore.

In some embodiments, the target polynucleotide in step (d) is fully translocated from the first fluidic volume through the first fluidic pore.

In some embodiments, the method comprises repeating step (c) and (d) prior to step (e).

In some embodiments, the magnitude of the fourth voltage at the first pore is greater than the magnitude of the third voltage at the first pore to control the direction of the target polynucleotide.

In some embodiments, the magnitude of the fourth voltage at the first pore is less than the magnitude of the fourth voltage at the second pore such that the target polynucleotide continues to move toward the second pore, wherein the polarity of the fourth voltage at the first pore is such that the voltage is pulling the target polynucleotide toward the first fluidic volume from the chamber, and the polarity of the fourth voltage at the second pore is such that the voltage is pulling the target polynucleotide toward the second fluidic volume from the chamber.

In some embodiments, the magnitude of the fourth voltage at the first pore in step (f) is less than the magnitude of the fourth voltage at the second pore.

In some embodiments, the magnitude of the fifth voltage at the first pore in step (h) is greater than the magnitude of the fifth voltage at the second pore.

In some embodiments, the polarity of the first voltage at the first pore in step (c) is such that the voltage is pulling the target polynucleotide from the chamber toward the first fluidic volume.

In some embodiments, the fluidic volume has a positive polarity relative to the chamber during translocation of the target polynucleotide in step (c).

In some embodiments, the polarity of the second voltage at first pore in step (d) is such that the voltage is pulling the target polynucleotide from the first fluidic volume toward the chamber.

In some embodiments, the chamber has a positive polarity relative to the first fluidic volume during partial or full translocation of the target polynucleotide in step (d).

In some embodiments, in step (c), the target polynucleotide partially or fully translocates from the chamber through the first pore and into the first fluidic channel for a time period ranging from 30 ms to 500 ms or longer.

In some embodiments, in step (d), the target polynucleotide partially or fully translocates from the first fluidic channel through the first pore and into the chamber in a first direction for a time period ranging from 30 ms to 500 ms or longer.

In some embodiments, the method comprises, before each detection step, scanning for one or more features of the polynucleotide.

In some embodiments, the method further comprises detecting one or more features on the polynucleotide as each feature passes through the second pore in step g) that are not already detected when passing through the first pore.

In some embodiments, the method comprises, between steps c) and d), scanning for one or more features on the target polynucleotide, and detecting the first set of features when the target polynucleotide passes through the first pore.

In some embodiments, steps c) through i) comprises a first cycle of feature detection in both directions.

In some embodiments, the method further comprises repeating steps c) through i) to detect a third and fourth set of features, in a second cycle of feature detection in both directions.

In some embodiments, the first voltage at the first pore is applied between the first fluidic volume and the chamber, and the first voltage at the second pore is applied between the chamber and the second fluidic volume of the device.

In some embodiments, the first fluidic volume is a first fluidic channel, and the second fluidic volume is a second fluidic channel.

In some embodiments, the polynucleotide partially or fully translocates from the first fluidic channel through the first pore and into the chamber for a time period ranging from 30 ms to 500 ms or longer.

In some embodiments, a portion of the target polynucleotide moves from the first pore through the second pore for a time period ranging from 30 ms to 500 ms or longer.

In some embodiments, at least a portion of the target polynucleotide moves from the chamber through the second pore and into the second fluidic channel for a time period ranging from 30 ms to 500 ms or longer.

In some embodiments, the target polynucleotide translocates through the first pore, through the second pore, or through the first pore and the second pore.

In some embodiments, detecting the set of features of the polynucleotide is accomplished with an ionic current event from the first pore, the second pore, or both.

In some embodiments, said detecting comprises detecting a first ionic current event when the one or more features is passing through the first pore in a first direction in step (g), and a second ionic current event when the one or more features is passing through the second pore in the first direction in step (g).

In some embodiments, said detecting comprises detecting a third ionic current event when the one or more features is passing through the first pore in a second direction in step (h), and a fourth ionic current event when the one or more features is passing through the second pore in the second direction in step (h).

In some embodiments, the first end of the polynucleotide is positioned in the first fluidic channel away from the first pore at a distance ranging from 5 microns to 5 millimeters or more.

In some embodiments, the second end of the target polynucleotide is positioned in the first fluidic channel away from the at least first pore at a distance ranging from 5 microns to 5 millimeters or more.

In some embodiments, the target polynucleotide moves from the second pore into the second fluidic channel.

In some embodiments, at least a portion of the target polynucleotide moves from the second fluidic channel through the second pore and into the chamber for a time period ranging from 5 ms to 500 ms.

In some embodiments, the first end of the target polynucleotide is positioned in the second fluidic channel away from the second pore at a distance ranging from 5 microns to 5 millimeters or more.

In some embodiments, the second end of the target polynucleotide is positioned in the second fluidic channel away from the second pore at a distance ranging from 2 microns to 5 millimeters or more.

In some embodiments, the first voltage at the first pore is maintained for a time period ranging from 0-1000 milliseconds, 0-20 milliseconds, 20-50 seconds, 50-100 seconds, 100-500 seconds, or 500-1000 seconds.

In some embodiments, the first voltage at the first pore is maintained for a time period ranging from 20 ms or more, 50 ms or more, 120 ms or more, 150 ms or more, 300 ms or more, 500 ms or more, 1000 milliseconds or more, 20 seconds or more, 60 seconds or more, 120 seconds or more, 150 seconds or more, 300 seconds or more, 500 seconds or more, or 1000 seconds or more.

In some embodiments, the first voltage is maintained at the time period after capture and translocation of the target polynucleotide through the first pore.

In some embodiments, the method further comprises, between steps c) and d), adjusting the first voltage to an intermediate voltage of 0 mV for a time period ranging from 0-1000 milliseconds, 0-20 milliseconds, 20-50 seconds, 50-100 seconds, 100-500 seconds, or 500-1000 seconds.

In some embodiments, the method further comprises, between steps c) and d), adjusting the first voltage to an intermediate voltage of 0 mV for a time period ranging from 10 ms to 5 seconds or longer.

In some embodiments, the method further comprises, between steps c) and d), adjusting the first voltage to an intermediate voltage of 0 mV for a time period ranging from 10 ms to 5 seconds or longer, 5 seconds to 50 seconds or longer, 50 seconds to 60 seconds or longer, 60 seconds to 120 seconds or longer, 120 seconds to 180 seconds or longer, 180 seconds to 240 or longer, or 240 seconds to 300 seconds or longer.

In some embodiments, said adjusting the first voltage to the intermediate voltage of 0 mV is maintained for a time period sufficient to allow the polynucleotide to entropically relax to an equilibrium configuration.

In some embodiments, the polynucleotide is within the geometrically constrained enclosure of the first fluidic volume or the second fluidic volume for a time period ranging from 10 ms to 5 seconds or longer, 5 seconds to 50 seconds or longer, 50 seconds to 60 seconds or longer, 60 seconds to 120 seconds or longer, 120 seconds to 180 seconds or longer, 180 seconds to 240 or longer, or 240 seconds to 300 seconds or longer.

In some embodiments, the polynucleotide is within the geometrically constrained enclosure of the second fluidic volume for a time period ranging from 10 ms to 5 seconds or longer, 5 seconds to 50 seconds or longer, 50 seconds to 60 seconds or longer, 60 seconds to 120 seconds or longer, 120 seconds to 180 seconds or longer, 180 seconds to 240 or longer, or 240 seconds to 300 seconds or longer.

In some embodiments, the first voltage, second voltage, third voltage, and/or fourth voltage at the first pore each independently range from 0 mV to 900 mV in magnitude; and the first voltage, second voltage, third voltage, and/or fourth voltage at the second pore each independently range from 0 mV to 900 mV in magnitude.

In some embodiments, the third voltage at the first pore in step (e) is 0 mV.

In some embodiments, the third voltage at the second pore in step (e) ranges from 25 mV to 600 mV.

In some embodiments, the method further comprises computing, with a processor, the speed of the one or more features of the polynucleotide from the time difference between detection of the one or more features in the first pore and the second pore, and the known distance between the first pore and the second pore.

In some embodiments, the method further comprises computing, with a processor, the distances between the one or more features by using the computed speed of a feature of the polynucleotide, from the time between one or more features detected in the sensor current from the first pore, the sensor current from the second pore, or both.

In some embodiments, the polynucleotide exhibits a minimum time duration during said detecting step (g) and detection step (i) that it was captured and partially or fully translocated through the first pore and/or through said second pore, as an indication that the polynucleotide is above a minimum length.

In some embodiments, where a feature on the polynucleotide is identified as a target when the minimum time duration is longer than a threshold, and a feature is identified as a non-target when the time duration is shorter than the threshold.

In some embodiments, the method further comprises computing, with a processor, the speed of the one or more features of the target polynucleotide for every scan.

In some embodiments, the method further comprises computing, with a processor, the statistics on the speed of the one or more features using the distribution of speeds for every scan.

In some embodiments, the method further comprises computing, with a processor, the time history of the speed of the target polynucleotide using the speed of all the features in a given scan and given direction of scanning.

In some embodiments, the target polynucleotide is substantially linearized.

In some embodiments, the first fluidic channel and/or second fluidic channel has a length ranging from about 0.01 mm to about 5 mm.

In some embodiments, the first fluidic channel and/or second fluidic channel has a depth ranging from about 0.05 µm to about 2 µm.

In some embodiments, the first fluidic channel and/or second fluidic channel has a width ranging from 50-500 µm.

In some embodiments, the target polynucleotide is substantially linearized by the action of the adjustments to the first voltage, or the second voltage, or both.

In some embodiments, the first voltage creates voltage gradient across the at least first pore and along the length of the first fluidic channel.

In some embodiments, the second voltage creates voltage gradient across the at second pore and along the length of the second fluidic channel.

In some embodiments, the resistance of the first fluidic channel is inversely proportional to the first fluidic channel width.

In some embodiments, the resistance of the second fluidic channel is inversely proportional to the second fluidic channel width.

In some embodiments, the resistance of the first fluidic channel and/or second fluidic channel is proportional to the volume of the first fluidic channel and/or second fluidic channel.

In some embodiments, the resistance of the first fluidic channel and/or second fluidic channel is proportional to the volume of the first fluidic channel and/or second fluidic channel.

In some embodiments, the resistance of the first fluidic channel and/or second fluidic channel is proportional to the radius of the first fluidic channel and/or second fluidic channel.

In some embodiments, the resistance of the first fluidic channel and/or second fluidic channel is proportional to the cross-sectional radius of the first fluidic channel and/or second fluidic channel.

In some embodiments, the target polynucleotide is substantially linearized by the action of the adjustments to the first voltage, the second voltage, the third voltage, and/or fourth voltage at the first pore, the second pore, or both.

In some embodiments, the first fluidic channel and/or second fluidic channel comprises a geometrically constrained volume.

In some embodiments, the controller determines which of the one or more features of the target polynucleotide to perform additional recapturing of the one or more features in a first direction and/or a second direction.

In some embodiments, the method further comprises moving away from one or more features of the polynucleotide already recaptured.

In some embodiments, the method further comprises controlling, with a controller, the: a) number of features to scan for; b) number of features to re-scan; c) type of features to scan or re-scan for; d) number of cycles to scan or re-scan for; e) movement of the target polynucleotide; f) direction of the target polynucleotide; g) speed of the target polynucleotide; or h) a combination thereof.

In some embodiments, the method further comprises controlling the number of features to scan.

In some embodiments, the controller determines which of the one or more features to perform additional scans on.

In some embodiments, the method further comprises moving away from one or more features already scanned.

In some embodiments, the method further comprises scanning for regions on the polynucleotide that have not yet been scanned.

In some embodiments, the method further comprises building, with a processor, a consensus map for each polynucleotide.

In some embodiments, said building comprises a machine learning algorithm that is trained to detect one or more features based on training data and probabilistic models.

In some embodiments, the method further comprises building, with a processor, a local map for each polynucleotide in real-time.

In some embodiments, the method further comprises repeating steps c) through i) until the target polynucleotide exits the pore device.

In some embodiments, the method prevents exiting of the target polynucleotide from the chamber of the device for a time period ranging from 5 ms to 5 minutes.

In some embodiments, the method prevents exiting of the target polynucleotide from the first fluidic channel or the second fluidic channel of the device for a time period ranging from 5 ms to 5 minutes.

In some embodiments, the one or more features comprises: a) one or more payload molecules bound to the polynucleotide; b) one or more payload molecules hybridized to the polynucleotide; c) one of more payload molecules incorporated into the genome of the polynucleotide; d) a molecular motif on a polynucleotide sequence of the target polynucleotide; or e) a combination thereof.

In some embodiments, the method further comprises determining the distance between each of the one or more features of the target polynucleotide.

In some embodiments, the method further comprises determining the distance between each feature in the first set of features of the target polynucleotide.

In some embodiments, the method further comprises determining the distance between each feature in the second set of features of the target polynucleotide.

In some embodiments, the first cycle comprises one or more scans performed by a processor to detect the first set of features.

In some embodiments, the first cycle comprises two or more scans, three or more scans, four or more scans, five or more scans, six or more scans, seven or more scans, eight or more scans, nine or more scans, or ten or more scans.

In some embodiments, the second cycle comprises one or more scans performed by a processor to detect the third set of features.

In some embodiments, the second cycle comprises two or more scans, three or more scans, four or more scans, five or more scans, six or more scans, seven or more scans, eight or more scans, nine or more scans, or ten or more scans.

In some embodiments, the method further comprises repeating steps c) through i) for a third cycle, a fourth cycle, and a fifth cycle; or when the polynucleotide exits the device.

In some embodiments, the first set of features is one feature or more, two features or more, three features or more, four features or more, five features or more, six features or more, seven features or more, eight features or more, nine features or more, or ten features or more.

In some embodiments, the second set of features are greater than the first set of features.

In some embodiments, the set of features across sets of scans are combined to generate maps of locations and distances between features, for each target polynucleotide.

In some embodiments, the one or more features comprises: a DNA-binding protein; a polypeptide; an anti-DNA antibody; streptavidin; a transcription factor; a histone; a peptide nucleic acid (PNA); a DNA-hairpin; a DNA molecule; an aptamer; a 5-methylcytosines (5mC) region; a 5-hydroxymethylcytosines (5hmC) region; a nucleotide base; two or more nucleotide bases; or a combination thereof.

In some embodiments, the polynucleotide sequence has a length ranging from 5 base pairs to about 3,000,000 base pairs.

In some embodiments, the target polynucleotide is selected from the group consisting of: a double-stranded DNA, a single-stranded DNA, double-stranded RNA, single-stranded RNA, and DNA-RNA hybrid.

In some embodiments, the method further comprises controlling the direction of the target polynucleotide through the first and second pore via a controller, a processor, and a non-transitory computer-readable medium comprising instructions that cause the processor to: change the direction of the target polynucleotide when a first set of features is detected.

In some embodiments, said adjusting the first voltage and the second voltage occurs in real-time, wherein said adjusting is performed by an active feedback controller using hardware and software.

In some embodiments, the method further comprises controlling, with a feedback controller, the first or second voltage based on feedback of the first or second or both ionic current measurements.

In some embodiments, the processor comprises a field programmable gate array (FPGA) or an application-specific integrated circuit (ASIC).

In some embodiments, the controller comprises a field programmable gate array (FPGA) or an application-specific integrated circuit (ASIC).

In some embodiments, the controller is a microcontroller.

In some embodiments, the FPGA or ASIC executes control logic to change the: a) number of features to scan for; b) number of features to re-scan; c) type of features to scan or re-scan for; d) number of cycles to scan or re-scan for; e) movement of the target polynucleotide; f) direction of the target polynucleotide; g) speed of the target polynucleotide; h) voltage of the first and second pore; or i) a combination thereof.

In some embodiments, the first set of features and the second set of features are the same.

In some embodiments, the first set of features and the second set of features are different from one another.

In some embodiments, the controller is configured to perform a control voltage frequency sweep of the polynucleotide in a first direction, second direction, or both.

In some embodiments, the controller is configured to perform a control voltage amplitude sweep of the polynucleotide in a first direction, second direction, or both.

In some embodiments, the controller is configured to adjust the speed of the polynucleotide.

In some embodiments, the speed ranges from 0.1 base pairs per millisecond to 10 base pairs per millisecond.

In some embodiments, the controller is configured to adjust the first and second voltages in order to perform a plurality of scans of the polynucleotide at a plurality of speeds.

In some embodiments, said performing the plurality of scans of the polynucleotide at the plurality of speeds improves the accuracy of the detection of one or more features.

In some embodiments, the method comprises performing a plurality of scans of the polynucleotide at a plurality of speeds.

In some embodiments, the controller is configured to control the speed range of the polynucleotide in a first direction, second direction, or both.

In some embodiments, the controller is configured to control the voltage range of the first and second pores when the polynucleotide moves through the first and second pore in a first direction, second direction, or both.

In some embodiments, the controller is configured to determine an optimal speed range of the polynucleotide in the first direction, second direction, or both, wherein the optimal speed range of the polynucleotide reduces the effect of Brownian motion on the polynucleotide.

In some embodiments, controlling the speed range of the polynucleotide comprises determining the optimal speed of the polynucleotide for sequencing.

BRIEF DESCRIPTION OF THE DRAWINGS

FIG. 11 shows that flossing increases linearization of DNA in dual pore device. (a) Typical $I_1$ traces of single pore events, including both unfolded folded examples. Only single pore events that resulted in eventual co-capture were included in subsequent probability calculations (pre-i step events in FIG. 16). (b) Typical $I_2$ trace of a multi-scan event in which scan I shows folding and subsequent scans do not. (c) Illustration of a mechanism by which the folded part (initially only in $I_2$) gets removed by the 2nd scan when the molecule moves R-to-L, as described in the text. (d) The probability P (±95% error bar) is the fraction of events that are unfolded, for the different translocation types. A total of 309 events experienced all four types in sequential order.

FIG. 13 depicts Table 1 with five different multi-scan events with at least 30 cycles. The table reports the number of cycles, which is equal to the number of scans in each direction, and the number of tag-pairs that contributed to each separation distance estimate.

FIG. 21 depicts Table S3 showing statistics related to tag separation estimation from nine multi-scan events.

FIG. 28 shows a non-limiting example of when the target polynucleotide is pushed through the first pore for a time period of approximately 30 ms, and then the first voltage is adjusted to 0 mV "OFF" when the device includes a channel, and when the device does not include a channel.

FIG. 29 shows a non-limiting example of polynucleotide detection/capture time when the device includes a channel and when the device does not include a channel.

Figure 1:
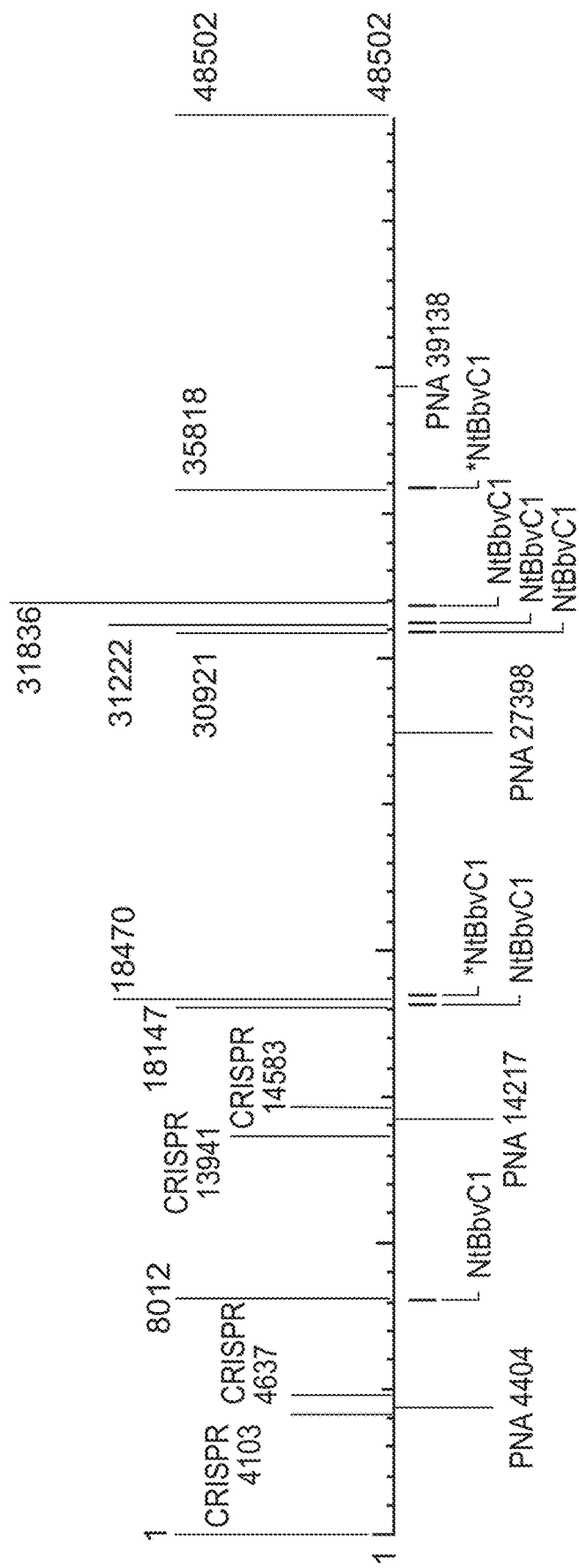
FIG. 1 depicts DNA based tagging of a λ-DNA molecule. The tags depicted are in the identical positions as per mono-streptavidin. The DNA is nicked using the same nicking enzyme. Instead of incorporating a biotin labeled dUTP at the nick site, an N3-dUTP is incorporated. Excess dUTP is removed by filtration. A 90-nucleotide oligo with a 5'DCBO group is reacted with the DNA overnight (e.g., using copperless click reaction). The 5'DBCO nucleotide comprises a nucleotide sequence AAA AAA AAA AGG GAA AGG GAA AGG GAA AGA AAA AAA AAA AAA AAA AAA AGG GAA AGG GAA AAA AAA AAG AGA GAG AGA GAG AGA GAA GAG (SEQ ID NO:1).

The figures depict embodiments of the present invention for purposes of illustration only. One skilled in the art will readily recognize from the following discussion that alternative embodiments of the structures and methods illustrated herein may be employed without departing from the principles of the invention described herein.

Definitions

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

By "cleavage" it is meant the breakage of the covalent backbone of a target nucleic acid molecule (e.g., RNA, DNA). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events.

"Nuclease" and "endonuclease" are used interchangeably herein to mean an enzyme which possesses catalytic activity for nucleic acid cleavage (e.g., ribonuclease activity (ribonucleic acid cleavage), deoxyribonuclease activity (deoxyribonucleic acid cleavage), etc.). A "genome editing endonuclease" is an endonuclease that can be used for the editing of a cell's genome (e.g., by cleaving at a targeted location within the cell's genomic DNA). Examples of genome editing endonucleases include but are not limited to class 2 CRISPR/Cas endonucleases such as: (a) type II CRISPR/Cas proteins, e.g., a Cas9 protein; (b) type V CRISPR/Cas proteins, e.g., a Cpf1 protein, a C2c1 protein, a C2c3 protein, and the like; and (c) type VI CRISPR/Cas proteins, e.g., a C2c2 protein.

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

In some instances, a component (e.g., a nucleic acid component; a protein component; and the like) includes a label moiety. The terms "label", "detectable label", or "label moiety" as used herein refer to any moiety that provides for signal detection and may vary widely depending on the particular nature of the assay. Label moieties of interest include both directly detectable labels (direct labels) (e.g., a fluorescent label) and indirectly detectable labels (indirect labels) (e.g., a binding pair member). A fluorescent label can be any fluorescent label (e.g., a fluorescent dye (e.g., fluorescein, Texas red, rhodamine, ALEXAFLUOR® labels, and the like), a fluorescent protein (e.g., green fluorescent protein (GFP), enhanced GFP (EGFP), yellow fluorescent protein (YFP), red fluorescent protein (RFP), cyan fluorescent protein (CFP), cherry, tomato, tangerine, and any fluorescent derivative thereof), etc.). Suitable detectable (directly or indirectly) label moieties may include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label)(e.g., $^3$H, $^{125}$I, $^{35}$S, $^{14}$C, or $^{32}$P); an enzyme (an indirect label) (e.g., peroxidase, alkaline phosphatase, galactosidase, luciferase, glucose oxidase, and the like); a fluorescent protein (a direct label) (e.g., green fluorescent protein, red fluorescent protein, yellow fluorescent protein, and any convenient derivatives thereof); a metal label (a direct label); a colorimetric label; a binding pair member; and the like. By "partner of a binding pair" or "binding pair member" it is meant one of a first and a second moiety, wherein the first and the second moiety have a specific binding affinity for each other. Suitable binding pairs include, but are not limited to: antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Any binding pair member can be suitable for use as an indirectly detectable label moiety.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a ribonucleoprotein complex" includes a plurality of such complexes and reference to "the mutant dystrophin gene" includes reference to one or more mutant dystrophin genes and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides an automated method of mapping one or more features of a target polynucleotide. Also provided in the present disclosure are automated methods for sequencing a polynucleotide sequence. Also provided in the present disclosure are methods for differential detection of methylated and non-methylated regions in a polynucleotide sequence. Also provided in the present disclosure are methods of extended recapture of a polynucleotide in a nanopore device. Also provided are methods for sequencing a polynucleotide in a nanopore device. Also provided in the present disclosure are devices and systems for carrying out the methods of the present disclosure.

System and Devices

The present disclosure includes devices and systems for carrying out the methods disclosed herein. The present disclosure provides devices and systems for mapping one or more features of a polynucleotide sequence of a target polynucleotide through a first and a second pore. The present disclosure also provides devices and systems for capturing a target polynucleotide. The present disclosure also provides devices and systems for sequencing a polynucleotide sequence of a target polynucleotide through a first and second pore.

Aspects of the present disclosure include a dual-pore, dual-amplifier device for sequencing a polynucleotide sequence of a target polynucleotide through a first and a second pore. In some cases, the device comprises (i) an electrode connected configured to provide a first voltage at the first pore of the device, and provide a second voltage at the second pore of the device; (ii) a first pore; (iii) a second pore; wherein the first pore and the second pore are configured such that the target polynucleotide is capable of simultaneously moving across both pores in a first direction or a second direction, and in a controlled manner; (iv) one or more sensors capable of identifying: a first set of features, in a first cycle, from the target polynucleotide, during movement of the target polynucleotide through the first pore and the second pore in the first direction and, a second set of features, in the first cycle, from the target polynucleotide, during movement of the target polynucleotide through the second pore and the first pore in the second direction; (v) a processor; and (vi) a non-transitory computer-readable medium comprising instructions that cause the processor to: a) determine, from the one or more sensors, the simultaneous presence of the target polynucleotide in both pores; b) scan for one or more features of the target polynucleotide; c) count the first set of features in the first cycle in the first direction, and, responsive to that count, adjust one or both of the first and second voltages, to produce a first force and an opposing second force acting on said target polynucleotide, wherein said first and second forces change the direction and the speed of the movement of the target polynucleotide so that at least a portion of the target polynucleotide moves from the second pore to the first pore in the second direction; and d) repeat steps a) through c) to detect a third and fourth set of features, in a second cycle.

In some embodiments, the device comprises a first chamber. As used herein, the term "upper chamber" is used interchangeably with the term "fluidic channel", such as a first fluidic channel. In some embodiments, the device comprises a middle chamber. As used herein, the term "middle chamber" is used interchangeably with the term "the chamber". In some embodiments, the device comprises a first pore connecting the upper chamber and middle chamber. In some embodiments, the device comprises a second pore connecting the middle chamber and a lower chamber. As used herein, the term "lower chamber" is used interchangeably with the term "fluidic channel", such as a second fluidic channel. In some embodiments, the device comprises a lower chamber. In some embodiments, the device comprises a second fluidic channel. In some embodiments, the first fluidic channel, the second fluidic channel, and/or the chamber contain one or more electrodes for connecting to a power supply so that a separate voltage can be established across each of the pores between the chambers. In some embodiments, the device comprises an electrode connected to a power supply configured to provide a first voltage between the first fluidic channel and the chamber of the device, and provides a second voltage between the chamber and a second fluidic channel of the device. In some embodiments, the chamber is positioned above the first and second pores. In some embodiments, the chamber is positioned above the first and second fluidic channels. In some embodiments, the chamber is positioned below the first and second pores. In some embodiments, the chamber is positioned between the first and second pores. In some embodiments, the chamber is positioned between the first and second fluidic channels.

In some embodiments, the first pore and the second pore are configured such that the target polynucleotide is capable of simultaneously moving across both pores in a first direction or a second direction, and in a controlled manner. In some embodiments, the dual-pore device comprises one or more sensors. In some embodiments, the one or more sensors are capable of identifying a first set of features from the target polynucleotide. In some embodiments, the sensor is capable if identifying a first set of features, in a first cycle (e.g. a first cycle having one or more scans), during movement of the target polynucleotide through the first pore and the second pore in a first direction, wherein the first direction being from the first pore to the second pore. In some embodiments, the one or more sensors is capable of identifying a second set of features, in the first cycle, from the target polynucleotide, during movement of the target polynucleotide through the second pore and the first pore in the second direction. In some embodiments, the first direction is from the first pore to the second pore. In some embodiments, the second direction is from the second pore to the first pore. In some embodiments, the dual-pore device comprises a processor. In some embodiments, the dual-pore device comprises a non-transitory computer-readable medium comprising instructions that cause the processor to determine, from the one or more sensors, the simultaneous presence of the target polynucleotide in both pores. In some embodiments, the instructions cause the processor to scan for one or more features of the target polynucleotide. In some embodiments, the instructions cause the processor to count the first set of features in the first cycle in the first direction, and, responsive to that count, adjust one or both of the first and second voltages, to produce a first force and an opposing second force acting on said target polynucleotide. In some embodiments, the first and second forces change the direction and the speed of the movement of the target polynucleotide so that at least a portion of the target polynucleotide moves from the second pore to the first pore in the second direction. In some embodiments, the process is repeated to detect a second set of features, in a second cycle. In some embodiments, the process to detect third and fourth sets of features, in a second cycle. In some embodiments, the steps are repeated until the polynucleotide exits the dual-pore device.

Aspects of the present disclosure include a device for mapping one or more features of a target polynucleotide through a first and a second pore, the device comprising: (i) a first pore positioned between a chamber and a first fluidic volume, wherein the first pore is fluidically connected to the chamber and to the first fluidic volume, and wherein the first fluidic volume being a geometrically constrained enclosure on a side opposite of the first pore, (ii) a second pore positioned between the chamber and a second fluidic volume, wherein the second pore is fluidically connected to the chamber and to the second fluidic volume, and wherein the second fluidic volume being a geometrically constrained enclosure on a side opposite of the second pore; (iii) the enclosure of the first fluidic volume and the second fluidic volume, each comprising an inlet and an outlet for fluidic filling and electrode access, wherein the first pore is connected to the geometrically constrained enclosure of the first fluidic volume in a location in between the inlet and outlet, and wherein the second pore is connected to the geometrically constrained enclosure of the second fluidic volume in a location in between the inlet and outlet, (iv) at least one electrode positioned within the first fluidic volume, at least one electrode positioned within the second fluidic volume, and at least one electrode positioned within the chamber, (v) one or more sensors configured for independent voltage control and current measurement at each pore; (vi) a processor; and (vii) a non-transitory computer-readable medium comprising instructions that cause the processor to: a) apply a first voltage at the first pore and a first voltage at the second pore to capture and translocate the target polynucleotide through the first pore and into the first fluidic volume; b) apply a second voltage at the first pore and a second voltage at the second pore to recapture and partially or fully translocate the target polynucleotide from the first fluidic volume through the first pore; c) apply a third voltage at the first pore, and a third voltage at the second pore so that at least a portion of the target polynucleotide is captured by the second pore while remaining in the first pore; d) apply a fourth voltage at the first pore and a fourth voltage at the second pore to control the direction of motion of the target polynucleotide; e) detect in a first sensor current, a first set of features on the polynucleotide, as each feature passes through the first pore and again in a second sensor current as each feature passes through the second pore; f) apply a fifth voltage at the first pore and a fifth voltage at the second pore to reverse the direction of motion of the target polynucleotide; g) detect in the second sensor current, a second set of features in the target polynucleotide, as each feature passes through the second pore and again in the first sensor current as each feature passes through the first pore.

In some embodiments, further comprising instructions that cause the processor to: scan, after step a), for one or more features of the target polynucleotide as at least a portion of the target polynucleotide passes through the first pore; and detect the first set of features when the target polynucleotide passes through the first pore.

In some embodiments, further comprising instructions that cause the processor to: scan, after step b), scan for one or more features of the target polynucleotide as at least a portion of the target polynucleotide passes through the first pore.

In some embodiments, further comprising instructions that cause the processor to: scan, after step d), for one or more features of the target polynucleotide as at least a portion of the target polynucleotide passes through the first pore and again as each feature passes through the second pore.

In some embodiments, further comprising instructions that cause the processor to: scan, after step f), for one or more features of the target polynucleotide as at least a portion of the target polynucleotide passes through the second pore and again as each feature passes through the first pore.

In some embodiments, applying the voltage in step b) is responsive to a number of features detected when at least a portion of the target polynucleotide passes the first pore.

In some embodiments, adjusting the voltage in step c) is responsive to a number of features detected when at least a portion of the target polynucleotide passes through the first pore.

In some embodiments, applying the voltage in step f) is responsive to a number of features detected when at least a portion of the target polynucleotide passes through the first pore and again at least a portion of the target polynucleotide passes through the second pore.

In some embodiments, further comprising instructions that cause the processor to repeat steps c) through g).

In some embodiments, further comprising instructions that cause the processor to detect one or more features on the target polynucleotide as each feature passes through the first pore and again as the each feature passes through the second pore in step e) that have not already been detected.

In some embodiments, steps c) through g) comprises a first cycle of feature detection in both directions.

In some embodiments, further comprising repeating steps c) through g) to detect a third and fourth set of features, in a second cycle of feature detection in both directions.

In some embodiments, the instructions further cause the processor to repeat c) until the target polynucleotide exits the device.

In some embodiments, the device comprises at least one electrode positioned within the first fluidic channel, and at least one electrode positioned within the second fluidic channel.

In some embodiments, the one or more sensors comprises dual-amplifier electronics configured for voltage control and current measurement at the first pore and the second pore.

In some embodiments, the first voltage at the first pore and the second voltage at the second pore are independently controlled, wherein the first voltage and the second voltage ranges from 0 mV to 1000 mV.

In some embodiments, the first pore and the second pore are about 10 nm to 2 μm apart from each other.

In some embodiments, the device is a dual-nanopore chip comprising a length of 2 mm or more, 3 mm or more, 4 mm or more, 5 mm or more, 6 mm or more, 7 mm or more, or 8 mm or more; and a width of 2 mm or more, 3 mm or more, 4 mm or more, 5 mm or more, 6 mm or more, 7 mm or more, or 8 mm or more.

In some embodiments, the diameter of the pore ranges from about 2 nm to about 50 nm.

In some embodiments, the diameter of the pore is about 20 nm.

In some embodiments, the first pore and the second pore are about 500 nm apart from each other.

In some embodiments, the first pore has a depth of at least about 0.3 nm separating the first channel and the chamber and the second pore has a depth of at least about 0.3 nm separating the chamber and the second channel.

In some embodiments, the chamber is connected to a common ground relative to the first voltage at the first pore and second voltage at the second pore.

The device of any of the preceding claims, wherein the device further comprises a controller.

In some embodiments, the controller is configured to vary the number of features of the polynucleotide to scan.

In some embodiments, the controller is configured to vary the number of scans.

In some embodiments, the controller is configured to control the location of the polynucleotide that is scanned.

In some embodiments, the controller is configured to change the region of the polynucleotide that is scanned.

In some embodiments, the controller is configured to control the: a) number of features to scan for; b) number of features to re-scan;

c) type of features to scan or re-scan for; d) number of cycles to scan or re-scan for; e) movement of the target polynucleotide; 0 direction of the target polynucleotide; g) speed of the target polynucleotide; h) voltage of the first and second pore; or i) a combination thereof.

In some embodiments, the processor comprises a field programmable gate array (FPGA) or an application-specific integrated circuit (ASIC).

In some embodiments, the controller comprises a field programmable gate array (FPGA) or an application-specific integrated circuit (ASIC).

In some embodiments, the controller is a microcontroller.

In some embodiments, the FPGA or ASIC executes control logic to change the: a) number of features to scan for; b) number of features to re-scan; c) type of features to scan or re-scan for; d) number of cycles to scan or re-scan for; e) movement of the target polynucleotide; f) direction of the target polynucleotide; g) speed of the target polynucleotide; h) voltage of the first and second pore; or i) a combination thereof.

In some embodiments, the controller is configured to control the direction of movement of the polynucleotide.

In some embodiments, further comprising instructions that cause the processor to build a local map of a region of the polynucleotide containing the one or more features based on the scans.

In some embodiments, further comprising instructions that cause the processor to build a consensus map of a region of the polynucleotide containing the one or more features based on the scans.

In some embodiments, wherein said building comprises a machine learning algorithm that is trained to detect one or more features based on training data and probabilistic models.

In some embodiments, further comprising instructions that cause the processor to compute the speed of a feature of the target polynucleotide from the time difference between detection of the feature in the first pore and the second pore, and the known distance between pore one and pore two.

In some embodiments, further comprising instructions that cause the processor to compute the distances between features from the speed of a feature of the target polynucleotide, from the time between features detected in the current signal from the first pore, the second pore, or both.

In some embodiments, further comprising instructions that cause the processor to compute the speed of a feature of the target polynucleotide for every scan, and to compute statistics on the speed of the feature by using the distribution of speeds.

In some embodiments, further comprising instructions that cause the processor to combine the speed of all the features and compute the time history of the speed of the polynucleotide in a given scan and given direction of scanning.

In some embodiments, further comprising instructions that cause the processor to perform a frequency sweep of the polynucleotide in a first direction, second direction, or both.

In some embodiments, further comprising instructions that cause the processor to perform an amplitude sweep of the polynucleotide in a first direction, second direction, or both.

In some embodiments, further comprising instructions that cause the processor to adjust the speed of the polynucleotide.

In some embodiments, the speed ranges from 1 base pair per millisecond to 10 base pairs per millisecond.

In some embodiments, further comprising instructions that cause the processor to adjust the first and second voltages in order to perform a plurality of scans of the polynucleotide at a plurality of speeds.

In some embodiments, said performing the plurality of scans of the polynucleotide at the plurality of speeds improves the accuracy of the detection of one or more features.

In some embodiments, further comprising instructions that cause the processor perform a plurality of scans of the polynucleotide at a plurality of speeds.

In some embodiments, further comprising instructions that cause the processor to control the speed range of the polynucleotide in a first direction, second direction, or both.

In some embodiments, further comprising instructions that cause the processor to control the voltage range of the first and second pores when the polynucleotide moves through the first and second pore in a first direction, second direction, or both.

In some embodiments, further comprising instructions that cause the processor to determine an optimal speed range of the polynucleotide in the first direction, second direction, or both, wherein the optimal speed range of the polynucleotide reduces the effect of Brownian motion on the polynucleotide.

In some embodiments, controlling the speed range of the polynucleotide comprises determining the optimal speed range of the polynucleotide for sequencing.

Aspects of the present disclosure include systems for carrying out the methods described herein. Aspects of the present disclosure include a system comprising: a) a device for mapping one or more features of a target polynucleotide through a first and a second pore, the device comprising: (i) a first pore positioned between a chamber and a first fluidic volume, wherein the first pore is fluidically connected to the chamber and to the first fluidic volume, and wherein the first fluidic volume being a geometrically constrained enclosure on a side opposite of the first pore, (ii) a second pore positioned between the chamber and a second fluidic volume, wherein the second pore is fluidically connected to the chamber and to the second fluidic volume, and wherein the second fluidic volume being a geometrically constrained enclosure on a side opposite of the second pore; (iii) the enclosure of the first fluidic volume and the second fluidic volume, each comprising an inlet and an outlet for fluidic filling and electrode access, wherein the first pore is connected to the geometrically constrained enclosure of the first fluidic volume in a location in between the inlet and outlet, and wherein the second pore is connected to the geometrically constrained enclosure of the second fluidic volume in a location in between the inlet and outlet, (iv) at least one electrode positioned within the first fluidic volume, at least one electrode positioned within the second fluidic volume, and at least one electrode positioned within the chamber, (v) one or more sensors configured for independent voltage control and current measurement at each pore; (b) a processor; and (c) a non-transitory computer-readable medium comprising instructions that cause the processor to: i) apply a first voltage at the first pore and a first voltage at the second pore to capture and translocate the target polynucleotide through the first pore and into the first fluidic volume; ii) apply a second voltage at the first pore and a second voltage at the second pore to recapture and partially or fully translocate the target polynucleotide from the first fluidic volume through the first pore; iii) apply a third voltage at the first pore, and a third voltage at the second pore so that at least a portion of the target polynucleotide is captured by the second pore while remaining in the first pore; iv) apply a fourth voltage at the first pore and a fourth voltage at the second pore to control the direction of motion of the target polynucleotide; v) detect in a first sensor current, a first set of features on the polynucleotide, as each feature passes through the first pore and again in a second sensor current as each feature passes through the second pore; vi) apply a fifth voltage at the first pore and a fifth voltage at the second pore to reverse the direction of motion of the target polynucleotide; vii) detect in the second sensor current, a second set of features in the target polynucleotide, as each feature passes through the second pore and again in the first sensor current as each feature passes through the first pore.

In some embodiments, further comprising instructions that cause the processor to: scan, after step i), for one or more features of the target polynucleotide as at least a portion of the target polynucleotide passes through the first pore; and detect the first set of features when the target polynucleotide passes through the first pore.

In some embodiments, further comprising instructions that cause the processor to: scan, after step ii), scan for one or more features of the target polynucleotide as at least a portion of the target polynucleotide passes through the first pore.

In some embodiments, further comprising instructions that cause the processor to: scan, after step iv), for one or more features of the target polynucleotide as at least a portion of the target polynucleotide passes through the first pore and again as each feature passes through the second pore.

In some embodiments, further comprising instructions that cause the processor to: scan, after step vii), for one or more features of the target polynucleotide as at least a portion of the target polynucleotide passes through the second pore and again as each feature passes through the first pore.

In some embodiments, applying the voltage in step ii) is responsive to a number of features detected when at least a portion of the target polynucleotide passes the first pore.

In some embodiments, adjusting the voltage in step iii) is responsive to a number of features detected when at least a portion of the target polynucleotide passes through the first pore.

In some embodiments, applying the voltage in step vii) is responsive to a number of features detected when at least a portion of the target polynucleotide passes through the first pore and again at least a portion of the target polynucleotide passes through the second pore.

In some embodiments, further comprising instructions that cause the processor to repeat steps iii) through vii).

In some embodiments, further comprising instructions that cause the processor to detect one or more features on the target polynucleotide as each feature passes through the first pore and again as the each feature passes through the second pore in step e) that have not already been detected.

In some embodiments, steps iii) through vii) comprises a first cycle of feature detection in both directions.

In some embodiments, further comprising repeating steps iii) through vii) to detect a third and fourth set of features, in a second cycle of feature detection in both directions.

In some embodiments, the instructions further cause the processor to repeat iii) through vii) until the target polynucleotide exits the device.

In some embodiments, the device comprises at least one electrode positioned within the first fluidic channel, and at least one electrode positioned within the second fluidic channel.

In some embodiments, the one or more sensors comprises dual-amplifier electronics configured for voltage control and current measurement at the first pore and the second pore.

In some embodiments, the first voltage at the first pore and the second voltage at the second pore are independently controlled, wherein the first voltage and the second voltage ranges from 0 mV to 1000 mV.

In some embodiments, the first pore and the second pore are about 10 nm to 2 μm apart from each other.

In some embodiments, the device is a dual-nanopore chip comprising a length of 2 mm or more, 3 mm or more, 4 mm or more, 5 mm or more, 6 mm or more, 7 mm or more, or 8 mm or more; and a width of 2 mm or more, 3 mm or more, 4 mm or more, 5 mm or more, 6 mm or more, 7 mm or more, or 8 mm or more.

In some embodiments, the diameter of the pore ranges from about 2 nm to about 50 nm.

In some embodiments, the diameter of the pore is about 20 nm.

In some embodiments, the first pore and the second pore are about 500 nm apart from each other.

In some embodiments, the first pore has a depth of at least about 0.3 nm separating the first channel and the chamber and the second pore has a depth of at least about 0.3 nm separating the chamber and the second channel.

In some embodiments, the chamber is connected to a common ground relative to the first voltage at the first pore and second voltage at the second pore.

The device of any of the preceding claims, wherein the device further comprises a controller.

In some embodiments, the controller is configured to vary the number of features of the polynucleotide to scan.

In some embodiments, the controller is configured to vary the number of scans.

In some embodiments, the controller is configured to control the location of the polynucleotide that is scanned.

In some embodiments, the controller is configured to change the region of the polynucleotide that is scanned.

In some embodiments, the controller is configured to control the: a) number of features to scan for; b) number of features to re-scan; c) type of features to scan or re-scan for; d) number of cycles to scan or re-scan for; e) movement of the target polynucleotide; direction of the target polynucleotide; g) speed of the target polynucleotide; h) voltage of the first and second pore; or i) a combination thereof.

In some embodiments, the processor comprises a field programmable gate array (FPGA) or an application-specific integrated circuit (ASIC).

In some embodiments, the controller comprises a field programmable gate array (FPGA) or an application-specific integrated circuit (ASIC).

In some embodiments, the controller is a microcontroller.

In some embodiments, the FPGA or ASIC executes control logic to change the: a) number of features to scan for; b) number of features to re-scan; c) type of features to scan or re-scan for; d) number of cycles to scan or re-scan for; e) movement of the target polynucleotide; f) direction of the target polynucleotide; g) speed of the target polynucleotide; h) voltage of the first and second pore; or i) a combination thereof.

In some embodiments, the controller is configured to control the direction of movement of the polynucleotide.

In some embodiments, further comprising instructions that cause the processor to build a local map of a region of the polynucleotide containing the one or more features based on the scans.

In some embodiments, further comprising instructions that cause the processor to build a consensus map of a region of the polynucleotide containing the one or more features based on the scans.

In some embodiments, wherein said building comprises a machine learning algorithm that is trained to detect one or more features based on training data and probabilistic models.

In some embodiments, further comprising instructions that cause the processor to compute the speed of a feature of the target polynucleotide from the time difference between detection of the feature in the first pore and the second pore, and the known distance between pore one and pore two.

In some embodiments, further comprising instructions that cause the processor to compute the distances between features from the speed of a feature of the target polynucleotide, from the time between features detected in the current signal from the first pore, the second pore, or both.

In some embodiments, further comprising instructions that cause the processor to compute the speed of a feature of the target polynucleotide for every scan, and to compute statistics on the speed of the feature by using the distribution of speeds.

In some embodiments, further comprising instructions that cause the processor to combine the speed of all the features and compute the time history of the speed of the polynucleotide in a given scan and given direction of scanning.

In some embodiments, further comprising instructions that cause the processor to perform a frequency sweep of the polynucleotide in a first direction, second direction, or both.

In some embodiments, further comprising instructions that cause the processor to perform an amplitude sweep of the polynucleotide in a first direction, second direction, or both.

In some embodiments, further comprising instructions that cause the processor to adjust the speed of the polynucleotide.

In some embodiments, the speed ranges from 1 base pair per millisecond to 10 base pairs per millisecond.

In some embodiments, further comprising instructions that cause the processor to adjust the first and second voltages in order to perform a plurality of scans of the polynucleotide at a plurality of speeds.

In some embodiments, said performing the plurality of scans of the polynucleotide at the plurality of speeds improves the accuracy of the detection of one or more features.

In some embodiments, further comprising instructions that cause the processor perform a plurality of scans of the polynucleotide at a plurality of speeds.

In some embodiments, further comprising instructions that cause the processor to control the speed range of the polynucleotide in a first direction, second direction, or both.

In some embodiments, further comprising instructions that cause the processor to control the voltage range of the first and second pores when the polynucleotide moves through the first and second pore in a first direction, second direction, or both.

In some embodiments, further comprising instructions that cause the processor to determine an optimal speed range of the polynucleotide in the first direction, second direction, or both, wherein the optimal speed range of the polynucleotide reduces the effect of Brownian motion on the polynucleotide.

In some embodiments, controlling the speed range of the polynucleotide comprises determining the optimal speed range of the polynucleotide for sequencing.

Aspects of the present disclosure include systems for carrying out the methods using the devices described herein. Aspects of the system include a) a dual-pore, dual-amplifier device for mapping one or more features of a polynucleotide sequence of a target polynucleotide through a first and a second pore, the device comprising: (i) an electrode connected to a power supply configured to provide a first voltage between a first fluidic channel and a chamber of the device, and provide a second voltage between the chamber and a second fluidic channel of the device; (ii) a first pore; (iii) a second pore; wherein the first pore and the second pore are configured such that the target polynucleotide is capable of simultaneously moving across both pores in a first direction or a second direction, and in a controlled manner; (iv) one or more sensors capable of identifying: a first set of features, in a first cycle, from the target polynucleotide, during movement of the target polynucleotide through the first pore and the second pore in the first direction and, a second set of features, in the first cycle, from the target polynucleotide, during movement of the target polynucleotide through the second pore and the first pore in the second direction; c) a processor; and d) a non-transitory computer-readable medium, comprising instructions that cause the processor to: i) determine, from the sensor, the simultaneous presence of the target polynucleotide in both pores; ii) scan for one or more features of the target polynucleotide; iii) count the first set of features in the first cycle in the first direction, and, responsive to that count, adjust one or both of the first and second voltages, to produce a first force and an opposing second force acting on said target polynucleotide, wherein said first and second forces change the direction and the speed of the movement of the target polynucleotide so that at least a portion of the target polynucleotide moves from the second pore to the first pore in the second direction; and iv) repeat steps i) through iii) to detect a third and fourth set of features, in a second cycle.

Aspects of the present disclosure include a device for capturing a polynucleotide in a nanopore device, and then after extended distances and/or time periods, partially or fully recapturing the polynucleotide in the nanopore device, the device comprising the device comprising: (i) a first pore positioned between a chamber and a first fluidic volume, wherein the first pore is fluidically connected to the chamber and to the first fluidic volume, and wherein the first fluidic volume being a geometrically constrained enclosure on a side opposite of the first pore, (ii) the enclosure of the first fluidic volume comprising an inlet and an outlet for fluidic filling and electrode access, wherein the first pore is connected to the geometrically constrained enclosure of the first fluidic volume in a location in between the inlet and outlet, (iii) at least one electrode positioned within the first fluidic volume, and at least one electrode positioned within the chamber, (iv) a sensor configured to provide: a voltage between the said electrode within the first fluidic volume and said electrode within the chamber, and a current measurement that detects capture and translocation of the polynucleotide into and through the first pore; v) a processor; and vi) a non-transitory computer-readable medium, comprising instructions that cause the processor to: a) apply a first voltage to capture and translocate the polynucleotide from the chamber in a first direction through the first pore and into the first fluidic volume; b) detect in a first sensor current when the polynucleotide has translocated through the first pore in the first direction; c) apply a second voltage equal to zero for a time period while the polynucleotide is contained within the first fluidic volume; d) apply a third voltage to recapture and partially or fully translocate the polynucleotide from the first fluidic volume through the first pore and into the chamber; and e) detect in the first sensor current when the polynucleotide has partially or fully translocated through the first pore.

Aspects of the present disclosure include a system for capturing a polynucleotide in a nanopore device, and then after extended distances and/or time periods, partially or fully recapturing the polynucleotide, the system comprising (a) a nanopore device comprising: (i) a first pore positioned between a chamber and a first fluidic volume, wherein the first pore is fluidically connected to the chamber and to the first fluidic volume, and wherein the first fluidic volume being a geometrically constrained enclosure on a side opposite of the first pore, (ii) the enclosure of the first fluidic volume comprising an inlet and an outlet for fluidic filling and electrode access, wherein the first pore is connected to the geometrically constrained enclosure of the first fluidic volume in a location in between the inlet and outlet, (iii) at least one electrode positioned within the first fluidic volume, and at least one electrode positioned within the chamber, (b) a sensor configured to provide: a voltage between the said electrode within the first fluidic volume and said electrode within the chamber, and a current measurement that detects capture and translocation of the polynucleotide into and through the first pore; (c) a processor; and (d) a non-transitory computer-readable medium, comprising instructions that cause the processor to: i) apply a first voltage to capture and translocate the polynucleotide from the chamber in a first direction through the first pore and into the first fluidic volume; ii) detect in a first sensor current when the polynucleotide has translocated through the first pore in the first direction; iii) apply a second voltage equal to zero for a time period while the polynucleotide is contained within the first fluidic volume; iv) apply a third voltage to recapture and partially or fully translocate the polynucleotide from the first fluidic volume through the first pore and into the chamber; and v) detect in the first sensor current when the polynucleotide has partially or fully translocated through the first pore.

Nanopore Devices

Figure 8:
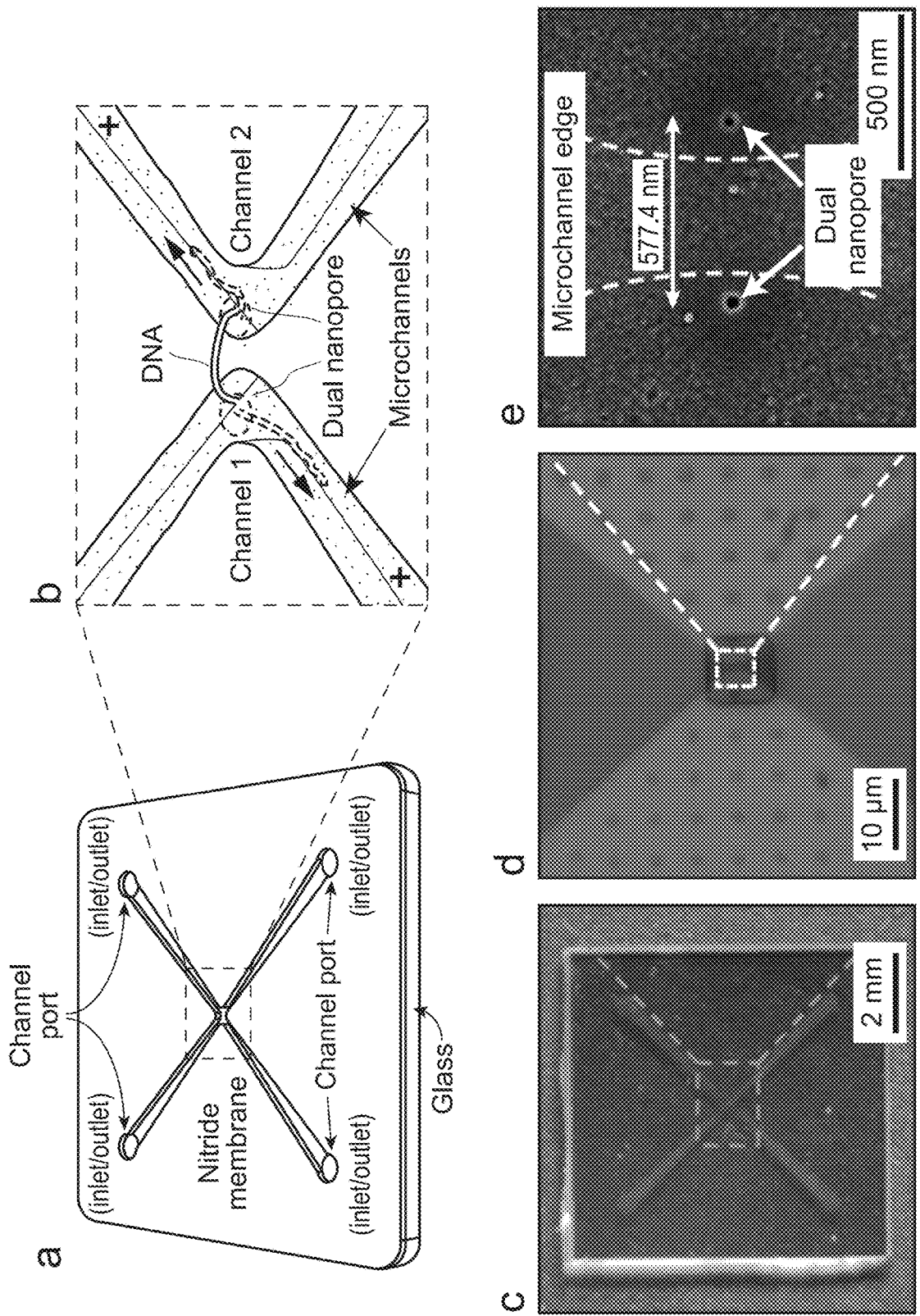
FIG. 8 depicts a 3D schematic of the dual-pore device. The two nanopores are placed on the same membrane. Two "V" shaped microchannels were checked on the glass, and the whole surface is covered with SiN membrane. The two channels guide the buffer to the center, where thee is a micrometer bridge separating the two channels. Nanopores were drilled on the tip of the channel. The same DNA molecule can be spanned in the two nanopores to achieve two-pore control. C, D, E, are the top view of the device in different magnification. C showed the whole chip in 8 mm×8 mm footprint size. D is the zoom in view showing the elbow of the v channels. E is the focus ion beam image showing the 2 nanopores. F is the side view showing the material: glass substrate and SiN membrane. For clarification, left side is depicted as channel 1 and pore 1, and right side is depicted as channel 2 and pore 2. G is the electrode setup to pull the same molecule into the channels at the same time. This design enables easy access to the two pores individually, since the electrode can be placed in the access ports in the corner and in the center common ground.

In some embodiments, a dual-pore nanopore device includes at least one nanopore (as shown in FIG. 8) that forms an opening in a structure separating an interior space of the nanopore device into two volumes. The nanopore devices also includes at least a sensor in electrical communication with the opening and configured to identify objects (for example, by detecting changes in electrical signal parameters indicative of objects) passing through the nanopore. Nanopore devices that may be used for the methods and systems described herein are also disclosed in PCT Publication Nos. WO/2013/012881 and WO/2018/236673, U.S. Application Publication No. 2017/0145481, and U.S. Pat. No. 9,863,912, which are hereby incorporated by reference in their entirety. Amplifiers and circuitry in the nanopore devices that may be used for the methods and systems are also disclosed in U.S. Application Publication No. 2017/0145481, which is hereby incorporated by reference in its entirety.

In some embodiments, the nanopore(s) in the nanopore device(s) are nanoscale or microscale in relation to characteristic feature dimensions. In one aspect, each pore has a size that allows a small or large molecule (e.g., nucleic acid molecule or fragment) or microorganism to pass. In examples, nanopores can have a diameter from 1 nm through 100 nm; however, in variations of the examples, nanopores can have a diameter less than 1 nm or greater than 100 nm. In some embodiments, the diameter of the pores range from about 2 nm to about 50 nm. In some embodiments, the diameter of the pores is about 20 nm. In variations, a nanopore has a depth ranging from 1-10,000 nm; however, in other variations, a nanopore can have a depth less than 1 nm or greater than 10,000 nm. Furthermore, during an experimental run, nanopore dimensions may vary (within a suitable range), as described in further detail below.

In some embodiments, each of the pores in the dual-pore device independently has a depth. In one embodiments, each pore has a depth that is least about 0.3 nm. In some embodiments, each pore has a depth that is at least about 0.6 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, or 90 nm. In some embodiments, each pore has a depth that is no more than about 100 nm. Alternatively, the depth is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 or 10 nm. In some embodiments, the pore has a depth that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm. In some embodiments, the first pore has a depth of at least about 0.3 nm separating the first fluidic channel and the chamber and the second pore has a depth of at least about 0.3 nm separating the chamber and the second fluidic channel.

In some aspects, each of the pores in the dual-pore device independently has a size that allows a small or large molecule or microorganism to pass. In some embodiments, each pore is at least about 1 nm in diameter. Alternatively, each pore is at least about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 35 nm, 40 nm, 45 nm, 50 nm, 60 nm, 70 nm, 80 nm, 90 nm or 100 nm in diameter.

In some aspects, the pore has a diameter that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In some embodiments, a nanopore of a nanopore device has a substantially round shape. "Substantially round", as used here, refers to a shape that is at least about 80 or 90% in the form of a cylinder. However, in alternative embodiments, a nanopore device can include nanopores that are square, rectangular, triangular, oval, hexangular, or of another morphology.

In some embodiments, the nanopore extends through a membrane. For example, the pore may be a protein channel inserted in a lipid bilayer membrane or it may be engineered by drilling, etching, or otherwise forming the pore through a solid-state substrate such as silicon dioxide, silicon nitride, grapheme, or layers formed of combinations of these or other materials.

In some embodiments, nanopores of a device can be spaced apart at distances ranging from 5-15,000 nm. In some embodiments, the nanopores of a device can be spaced apart at distances ranging from 10 to 1000 nm. However, in other variations, nanopores can be spaced apart less than 5 nm or greater than 15,000 nm. Furthermore, nanopores can be arranged in any position so long as they allow fluid communication between the chambers and have the prescribed size and distance between them. In some embodiments, the first pore and the second pore are about 10 nm to 500 nm apart from each other. In some embodiments, the first pore and the second pore are about 500 nm apart from each other. In one variation, the nanopores are placed so that there is no direct blockage between them. Still, in one aspect, the pores are substantially coaxial.

In some cases, the diameter of the pores ranges from about 2 nm to about 50 nm. In some cases, the diameter of the pore is about 20 nm. In some cases, the diameter of the first and/or second pore ranges from about 2 nm to about 50 nm. In some cases, the diameter of the first and/or second pore ranges from about 2 nm to about 8 nm. In some cases, the diameter of the first and/or second pore ranges from about 10 nm to about 20 nm. In some cases, the diameter of the pore ranges from about 20 nm to about 30 nm. In some cases, the diameter of the first and/or second pore ranges from about 30 nm to about 40 nm. In some cases, the diameter of the first and/or second pore ranges from about 40 nm to about 50 nm. In some cases, the diameter of the first and/or second pore is about 2 nm, about 4 nm, about 6 nm, about 8 nm, about 10 nm, about 12 nm, about 14 nm, about 16 nm, about 18 nm, about 20 nm, about 22 nm, about 24 nm, about 26 nm, about 28 nm, about 30 nm, about 32 nm, about 34 nm, about 36 nm, about 38 nm, about 40 nm, about 42 nm, about 44 nm, about 46 nm, about 48 nm, or about 50 nm. In some cases, the diameter of the first and/or second pore is about 19 nm. In some cases, the first pore and the second pore have the same diameters. In some cases, the diameter of the first and/or second pore is about 21 nm. In some cases, the diameter of the first and/or second pore is about 22 nm. In some cases, the diameter of the first and/or second pore is about 23 nm. In some cases, the diameter of the first and/or second pore is about 24 nm. In some cases, the diameter of the first and/or second pore is about 25 nm. In some cases, the diameter of the first and/or second pore is about 27 nm. In some cases, the diameter of the first and/or second pore is about 29 nm. In some cases, the first pore and the second pore have different diameters. In some cases, the diameter of the pore is about 20 nm.

In some embodiments, the device comprises a geometrically constrained fluidic volume. In some cases, the geometrically constrained fluidic volume is a fluidic channel. In some cases, the device comprises a first fluidic channel. As used herein, the term "upper chamber" is used interchangeably with the term "fluidic channel" and "geometrically constrained fluidic volume", such as a first fluidic channel. In some embodiments, the device comprises a middle chamber. As used herein, the term "middle chamber" is used interchangeably with the term "the chamber". In some embodiments, the device comprises a first pore connecting the upper chamber and middle chamber. In some embodiments, the device comprises a second pore connecting the middle chamber and a lower chamber. As used herein, the term "lower chamber" is used interchangeably with the term "fluidic channel" and "geometrically constrained fluidic volume", such as a second fluidic channel. In some embodiments, the device comprises a lower chamber. In some embodiments, the device comprises a second fluidic channel. In some embodiments, the first fluidic volume, the second fluidic volume, the first fluidic channel, the second fluidic channel, and/or the chamber contain one or more electrodes for connecting to a power supply so that a separate voltage can be established across each of the pores between the chambers. In some embodiments, the device comprises an electrode connected to a power supply configured to provide a first voltage between the first fluidic channel and the chamber of the device, and provides a second voltage between the chamber and a second fluidic channel of the device. In some embodiments, the chamber is positioned above the first and second pores. In some embodiments, the chamber is positioned above the first and second fluidic channels. In some embodiments, the chamber is positioned below the first and second pores. In some embodiments, the chamber is positioned between the first and second pores. In some embodiments, the chamber is positioned between the first and second fluidic channels.

In some cases, the shape of the first and/or second fluidic channels can be circular, square, rectangular, hexagonal, triangular, oval, polygon, V-shape, U-shape, or any other suitable shape. In some cases, the first fluidic channel and the second fluidic channel each have a V-shape and each have openings on either end of the V-shape, the V-shapes of the first and second fluidic channels arranged on the chip opposite one another with points of the V-shapes being adjacent to each other, and wherein the first nanopore is positioned at the point of the V-shape of the first fluidic channel and the second nanopore is positioned at the point of the V-shape of the second fluidic channel. In some embodiments, each of the fluidic channels is a different shape. The fluidic channels are not limited to the shapes and/or sizes as described herein and can be any shape and/or size as required per conditions specified to its intended use.

In some cases, the fluidic channels of the nanopore device comprises one or more openings on a side opposite of the first and/or second pores. In some cases, the fluidic channels of the nanopore device comprises two openings on a side opposite of the first and/or second pores.

In some embodiments, the nanopore device has electrodes positioned in the fluidic channels, geometrically constrained volume, or chambers and coupled to one or more power supplies in order to apply voltages across the nanopore(s). In some aspects, the power supply includes a voltage-clamp or a patch-clamp, which can supply a voltage across each pore and measure the current through each pore independently. In this respect, the power supply and the electrode configuration can set the chamber to a common ground for both power supplies. As such each nanopore can have its own respective applied voltage.

In some aspects, a first voltage $V_1$ and a second voltage $V_2$ of different nanopores of a nanopore device are independently adjustable. In one aspect, where multiple nanopores are connected by a chamber, the chamber can be adjusted to be a ground relative to the two voltages. In one aspect, the chamber comprises a medium for providing conductance between each of the pores and the electrode in the chamber. In one aspect, the chamber includes a medium for providing a resistance between each of the nanopores and the electrode in the chamber. Keeping such a resistance sufficiently small relative to the nanopore resistances is useful for decoupling the two voltages and currents across the pores, which is helpful for the independent adjustment of the voltages.

Adjustment of the voltages can be used to control the movement of charged particles in the chambers. For instance, when both voltages are set in the same polarity, a properly charged particle can be moved from the first fluidic channel to the chamber and to the second fluidic channel, or the other way around, sequentially. In some aspects, when the two voltages are set to opposite polarity, a charged particle can be moved from either the first fluidic channel or the second fluidic channel to the chamber and kept there.

The adjustment of the voltages in the device can be particularly useful for controlling the movement of a large molecule, such as a charged polymer, that is long enough to cross both pores at the same time. In such an aspect, the direction and the speed of the movement of the molecule can be controlled by the relative magnitude and polarity of the voltages as described below.

In some cases, the first initial voltage ranges from 0 mV to 1000 mV. In some cases, the first initial voltage ranges from 100-200 mV, 200-300 mV, 300-400 mV, 400-500 mV, 500-600 mV, 600-700 mV, 700-800 mV, 800-900 mV, 900-1000 mV, or 1000 or more mV. In some cases, the first initial voltage is 100 mV, 200 mV, 300 mV, 400 mV, 500 mV, 600 mV, 700 mV, 800 mV, 900 mV, or 1000 mV. In some cases, the second initial voltage ranges from 0 mV to 1000 mV. In some cases, the second initial voltage ranges from 100-200 mV, 200-300 mV, 300-400 mV, 400-500 mV, 500-600 mV, 600-700 mV, 700-800 mV, 800-900 mV, 900-1000 mV, or 1000 or more mV. In some cases, the second initial voltage is 100 mV, 200 mV, 300 mV, 400 mV, 500 mV, 600 mV, 700 mV, 800 mV, 900 mV, or 1000 mV.

In some cases, the methods of the present disclosure comprise adjusting the first and/or second voltages to control the movement of the target polynucleotide in the first pore, the first fluidic channel, the second pore, the second fluidic channel, and/or the chamber of the device. In some cases, the first voltage is adjusted to 0 mV after the target polynucleotide moves from the chamber, through the first pore, and into the first fluidic channel. In some cases, the first voltage is adjusted to 0 mV before translocation through the first pore, wherein at least a portion of the target polynucleotide is positioned in the chamber and at least a portion of the target polynucleotide is positioned in the first fluidic channel. In some cases, the second voltage at the second pore is adjusted to 500 mV when at least a portion of the target polynucleotide is positioned in the chamber and at least a portion of the target polynucleotide is positioned in the chamber. In some cases, the first voltage is adjusted to 0 mV, 50 mV, 100 mV, 150 mV, 200 mV, 250 mV, 300 mV, 350 mV, 400 mV, 450 mV, 500 mV, 550 mV, or 600 mV in the first direction, the second direction, the third direction, and/or the fourth direction. In some cases, the second voltage is adjusted to 0 mV, 50 mV, 100 mV, 150 mV, 200 mV, 250 mV, 300 mV, 350 mV, 400 mV, 450 mV, 500 mV, 550 mV, or 600 mV in the first direction, the second direction, the third direction, and/or the fourth direction. In some cases, the first voltage is adjusted to an intermediate voltage of 0 mV, and the second voltage is adjusted to 500 mV in in the third direction (e.g. when at least a portion of the target polynucleotide is cocaptured in the first pore and the second pore). In some cases, the first voltage is adjusted to 400 mV, and the second voltage is adjusted to 500 mV in the third direction (e.g. when at least a portion of the target polynucleotide is cocaptured in the first pore and the second pore). In some cases, the first voltage is adjusted to a voltage of 200 mV, and the second voltage is adjusted to a voltage of 500 mV in the third direction (e.g. when at least a portion of the target polynucleotide is cocaptured in the first pore and the second pore).

In some embodiments, a charged polymer, such as a polynucleotide, has a length that is longer than the combined distance that includes the depth of both pores plus the distance between the two pores. For example, a 1000 bp dsDNA is ~340 nm in length, and would be substantially longer than the 40 nm spanned by two 10 nm-length pores separated by 20 nm. In a first step, the polynucleotide is loaded into either the first fluidic channel or the second fluidic channel. In a first step, the polynucleotide is loaded into the chamber (e.g. the middle chamber or common chamber) of the device. By virtue of its negative charge under a physiological condition (~pH 7.4), the polynucleotide can be moved across a pore on which a voltage is applied. Therefore, in a second step, two voltages, in the same direction and at the same or similar magnitudes, are applied to the pores to induce movement of the polynucleotide across both pores sequentially. At about time when the polynucleotide reaches the second pore, one or both of the voltages can be changed. Since the polynucleotide is longer than the distance covering both pores, when the polynucleotide reaches the second pore, it is also in the first pore. A prompt change of direction of the voltage at the first pore, therefore, will generate a force that pulls the polynucleotide away from the second pore.

In some embodiments, the dual-pore device of the present disclosure can be used to carry our analysis of molecules or particles that move or are kept within the device by virtue of the controlled voltages applied over the pores. In one aspect, the analysis is carried out at either or both of the pores. Each voltage-clamp or patch-clamp system measures the ionic current through each pore, and this measured current is used to detect the one or more features of the passing charged particle or molecules, or any features associated with a passing charged particle or molecule.

As provided above, a polynucleotide can be loaded into both pores by two voltages having the same direction. In this example, once the direction of the voltage applied at the first pore is inversed and the new voltage-induced force is slightly less, in magnitude, than the voltage-induced force applied at the second pore, the polynucleotide will continue moving in the same direction, but at a markedly lower speed. In this respect, the amplifier supplying voltage across the second pore also measures current passing through the second pore, and the ionic current then determines the identification of a nucleotide that is passing through the pore, as the passing of each different nucleotide would give rise to a different current signature (e.g., based on shifts in the ionic current amplitude). Identification of each nucleotide in the polynucleotide, accordingly, reveals the sequence of the polynucleotide.

In some embodiments, the adjusted first voltage and second voltage at step are about 10 times to about 10,000 times as high, in magnitude, as the difference between the two voltages. For instance, the two voltages are 90 mV and 100 mV, respectively. In some embodiments, the magnitude of the voltages (~100 mV) is about 10 times of the difference between them, 10 mV. In some embodiments, the magnitude of the voltages is at least about 15 times, 20 times, 25 times, 30 times, 35 times, 40 times, 50 times, 100 times, 150 times, 200 times, 250 times, 300 times, 400 times, 500 times, 1000 times, 2000 times, 3000 times, 4000 times, 5000 times, 6000 times, 7000 times, 8000 times or 9000 times as high as the difference between them. In some aspects, the magnitude of the voltages is no more than about 10000 times, 9000 times, 8000 times, 7000 times, 6000 times, 5000 times, 4000 times, 3000 times, 2000 times, 1000 times, 500 times, 400 times, 300 times, 200 times, or 100 times as high as the difference between them.

In some aspects, repeated controlled delivery for re-sequencing a polynucleotide further improves the quality of sequencing. Each voltage is alternated as being larger, for controlled delivery in each direction.

The device can contain materials suitable for holding liquid samples, in particular, biological samples, and/or materials suitable for nanofabrication. In one aspect, such materials include dielectric materials such as, but not limited to, silicon, silicon nitride, silicon dioxide, graphene, carbon nanotubes, $TiO_2$, $HfO_2$, $Al_2O_3$, or other metallic layers, or any combination of these materials. In some aspects, for example, a single sheet of graphene membrane of about 0.3 nm thick can be used as the pore-bearing membrane.

Nanopore devices that are microfluidic can be made by a variety of means and methods. A focused electron or ion beam can be used to drill pores through the membranes, naturally aligning them. The pores can also be sculpted (shrunk) to smaller sizes by applying a correct beam focusing to each layer. Any single nanopore drilling method can also be used to drill the pair of pores in the two membranes, with consideration to the drill depth possible for a given method and the thickness of the membranes. Predrilling a micro-pore to a prescribed depth and then a nanopore through the remainder of the membranes is also possible to further refine the membrane thickness. In one example, a single beam can be used to form one or more nanopores (e.g., concentric nanopores) in a membrane of the nanopore device. Alternatively, in another example, different beams can be applied to each side of a on each side of the membranes, in order to generate aligned or non-aligned nanopores.

More specifically, the nanopore-bearing membranes can be made with transmission electron microscopy (TEM) grids with a 5-100 nm thick silicon, silicon nitride, or silicon dioxide windows. Spacers can be used to separate the membranes, using an insulator, such as SU-8, photoresist, PECVD oxide, ALD oxide, ALD alumina, or an evaporated metal material, such as Ag, Au, or Pt, and occupying a small volume within the otherwise aqueous portion of a middle chamber (e.g. chamber).

By virtue of the voltages present at the pores of the device, charged molecules can be moved through the pores between chambers. Speed and direction of the movement can be controlled by the magnitude and polarity of the voltages. Further, because each of the two voltages can be independently adjusted, the direction and speed of the movement of a charged molecule can be finely controlled in each chamber. For example, when a first set of features are detected in a first cycle in a first direction, the first voltage, the second voltage, or both, can be adjusted to a first and second pore to change the direction of the target molecule moves from the second pore to the first pore in a second direction.

In some aspects, a nanopore device further includes means to move a polymer across the pore and/or means to identify objects that pass through the pore. In some embodiments, the polymer is a polynucleotide or a polypeptide. In some aspects, the polymer is a polynucleotide. Non-limiting examples of polynucleotides include double-stranded DNA, single-stranded DNA, double-stranded RNA, single-stranded RNA, and DNA-RNA hybrids.

In some aspects, the dual-pore device can be used to identify one or more features of a polymer. In some embodiments, the one or more features is one feature, two features, three features, four features, or five features. In some embodiments, the one or more features is two or more features, three or more features, four or more features, five or more features, six or more features, seven or more features, eight or more features, nine or more features, or ten or more features. In some embodiments, the one or more features ranges from 1-5 features, 5-10 features, 10-15 features, 15-20 features, 20-25 features, 25-30 features, 30-35 features, 35-40 features, 40-45 features, or 45-50 features. In some embodiments, the one or more features ranges from 50 features to 100 features, 100 features to 1,000 features, 1,000 features to 10,000 features, 10,000 features to 100,000, 100,000 features to 200,000 features. In some embodiments, the one or more features is 50 features or more, 100 features or more, 1,000 features or more, 10,000 features or more, 100,000 features or more, or 200,000 features or more.

Aspects of the present disclosure include one or more features, wherein each feature is about from one another by about 100 base pairs, 300 base pairs, 500 base pairs, 1 kilo-base pair, 5 kilo base-pair, 10 kilo base pair, 20 kilo-base pair, or a combination thereof. In some embodiments, each features is spaced about from one another by about 25 base pairs or more, about 50 base pairs or more, about 100 base pairs or more, about 300 base pairs or more, about 500 base pairs or more, about 1 kilo-base pair or more, about 5 kilo base-pairs or more, about 10 kilo base pairs or more, about 20 kilo-base pairs or more, or a combination thereof. In some embodiments, each features is spaced about from one another by about 25 base pairs or less, about 50 base pairs or less, about 100 base pairs or less, about 300 base pairs or less, about 500 base pairs or less, about 1 kilo-base pair or less, about 5 kilo base-pairs or less, about 10 kilo base pairs or less, about 20 kilo-base pairs or less, or a combination thereof.

In some aspects, the dual-pore device can be used to identify a first set of features, a second set of features, a third set of features, a fourth set of features, a fifth set of features, a sixth set of features, a seventh set of features, an eighth set of features, a ninth set of features, and/or a tenth set of features. In some cases, each set of features comprises one or more features ranges from 1-5 features, 5-10 features, 10-15 features, 15-20 features, 20-25 features, 25-30 features, 30-35 features, 35-40 features, 40-45 features, or 45-50 features. In some embodiments, the first set of features overlaps with the second set of features. In some embodiments, the third set of features overlaps with the fourth set of features. In some embodiments, the first set of features partially overlaps with the second set of features. In some embodiments, the third set of features partially overlaps with the fourth set of features. In some embodiments, the first set of features are the same as the second set of features. In some embodiments, the third set of features are the same as the fourth set of features. In some embodiments, the first set of features are different from the second set of features. In some embodiments, the third set of features are different from the fourth set of features.

In some embodiments, the sets of features (e.g. first set, second set, third set, fourth set, fifth set, sixth set, seventh set, eighth set, ninth set, and/or tenth set) are associated with a first cycle, a second cycle, a third cycle, a fourth cycle, a fifth cycle, a sixth cycle, a seventh cycle, an eighth cycle, a ninth cycle, and/or a tenth cycle, respectively. In some cases, a first cycle comprises one or more scans performed by a processor to detect the first set of features. In some cases, the first cycle comprises two or more scans, three or more scans, four or more scans, five or more scans, six or more scans, seven or more scans, eight or more scans, nine or more scans, or ten or more scans. In some cases, the first cycle comprises two or more scans, four or more scans, six or more scans, eight or more scans, ten or more scans, twelve or more scans, fourteen or more scans, sixteen or more scans, eighteen or more scans, or twenty or more scans. In some cases, the first cycle comprises five or more scans, ten or more scans, fifteen or more scans, twenty or more scans, twenty-five or more scans, thirty or more scans, thirty-five or more scans, forty or more scans, forty-five or more scans, or fifty or more scans.

In some cases, the second cycle comprises one or more scans performed by a processor to detect the third set of features. In some cases, the second cycle comprises two or more scans, three or more scans, four or more scans, five or more scans, six or more scans, seven or more scans, eight or more scans, nine or more scans, or ten or more scans. In some cases, the second cycle comprises two or more scans, four or more scans, six or more scans, eight or more scans, ten or more scans, twelve or more scans, fourteen or more scans, sixteen or more scans, eighteen or more scans, or twenty or more scans. In some cases, the second cycle comprises five or more scans, ten or more scans, fifteen or more scans, twenty or more scans, twenty-five or more scans, thirty or more scans, thirty-five or more scans, forty or more scans, forty-five or more scans, or fifty or more scans. In some cases, the first cycle and the second cycle, together, comprise 50 or more scans, 100 or more scans, 150 or more scans, 200 or more scans, 250 or more scans, 300 or more scans, 350 or more scans, 400 or more scans, or 500 or more scans. In some embodiments, the first cycle, second cycle, third cycle, fourth cycle, and fifth cycle, together, comprise 50 or more scans, 100 or more scans, 150 or more scans, 200 or more scans, 250 or more scans, 300 or more scans, 350 or more scans, 400 or more scans, or 500 or more scans.

Aspects of the present disclosure include a processor and a computer-readable medium, comprising instructions that cause the processor to repeat the determining the presence of the target polynucleotide in both pores, scanning for one or more features, and changing the voltage to control movement of the polynucleotide (e.g. in either direction) for a third cycle, a fourth cycle, and a fifth cycle; or when the polynucleotide exits the device.

In some aspects, the dual-pore device can be used to identify one or more features of a polymer. In some embodiments, the polymer is a polynucleotide. In some embodiments, the one or more features of the polynucleotide comprises one or more features associated with the polynucleotide. Non-limiting examples of one or more features associated with the polynucleotide, include, but are not limited to, transcription factors, nucleosomes, or modifications to the features, including modification to histone tails. In some embodiments, one or more features in the polynucleotide comprises one or more sequence or structural variations.

In some embodiments, the one or more features of the polynucleotide comprises one or more payload molecules bound to the polynucleotide. In some embodiments, the one or more features of the polynucleotide comprises one or more payload molecules hybridized to the polynucleotide. In some embodiments, the one or more features of the polynucleotide comprises one of more payload molecules incorporated into the genome of the polynucleotide. In some embodiments, the one or more features of the polynucleotide comprises a molecular motif on a polynucleotide sequence of the target polynucleotide. In some embodiments, the one or more features comprises the position of: one or more CpG's; or one or more methylation cites and CpG's, on the polynucleotide sequence of the target polynucleotide. In some embodiments, the one or more features comprises the position of one or more histones on the target polynucleotide. In some embodiments, the one or more features comprises a molecule selected from the group consisting of: a nucleic acid, a TALEN, a CRISPR, a peptide nucleic acid, and a chemical compound. In some embodiments, the one or more features comprises a DNA-binding protein, a polypeptide, an anti-DNA antibody, a streptavidin, a transcription factor, a histone, a peptide nucleic acid (PNA), a DNA-hairpin, a DNA molecule, an aptamer, or a combination thereof.

Non-limiting examples of payload molecules bound to the polynucleotide can be found in can be found in U.S. Patent Publication No. 2018/0023115, which is hereby incorporated by reference in its entirety. For example, a payload molecule can include a dendrimer, double stranded DNA, single stranded DNA, a DNA aptamer, a fluorophore, a protein, a polypeptide, a nanorod, a nanotube, fullerene, a PEG molecule, a liposome, or a cholesterol-DNA hybrid. In some embodiments, the polynucleotide and the payload are connected directly or indirectly via a covalent bond, a hydrogen bond, an ionic bond, a van der Waals force, a hydrophobic interaction, a cation-pi interaction, a planar stacking interaction, or a metallic bond. The payload adds size to the target polynucleotide or amplicon, and facilitates detection, with the amplicon bound to the payload having a markedly different current signature when passing through the nanopore than background molecules. In some embodiments, the payload molecule comprises an azide chemical handle for attachment to a primer. In some embodiments, the primer is bound to a biotin molecule. In some embodiments, the payload molecule can bind to another molecule to affect the bulkiness of the molecule, thereby enhancing the sensitivity of detection of the amplicon in a nanopore. In some embodiments, the primer is bound to or comprises a binding site for binding to a biotin molecule. In some embodiments, the biotin is further bound by streptavidin to increase the size of the payload molecule for enhanced detection in a nanopore over background molecules. The added bulk can produce a more distinct signature difference between amplicon comprising a target sequence and background molecules.

In this embodiment, attachment of a payload to a primer or amplicon can be achieved in a variety of ways. For example, the primer may be a dibenzocyclooctyne (DBCO) modified primer, effectively labeling all amplicons with a DBCO chemical group to be used for conjugation purposes via copper-free "click" chemistry to an azide-tagged amplicon or primer.

In some aspects, the primer comprises a chemical modification that causes or facilitates recognition and binding of a payload molecule. For example, methylated DNA sequences can be recognized by transcription factors, DNA methyltransferases or methylation repair enzymes. In other embodiments, biotin may be incorporated into, and recognized by, avidin family members. In such embodiments, biotin forms the fusion binding domain and avidin or an avidin family member is the polymer scaffold-binding domain on the fusion. Due to their binding complementarity, payload molecule binding domains on a primer/amplicon and primer binding domains on a payload molecule may be reversed so that the payload binding domain becomes the primer binding domain, and vice versa.

Molecules, in particular proteins, that are capable of specifically recognizing nucleotide binding motifs are known in the art. For instance, protein domains such as helix-turn-helix, a zinc finger, a leucine zipper, a winged helix, a winged helix turn helix, a helix-loop-helix and an HMG-box, are known to be able to bind to nucleotide sequences. Any of these molecules may act as a payload molecule binding to the amplicon or primer.

In some aspects, the payload binding domains can be locked nucleic acids (LNAs), bridged nucleic acids (BNA), Protein Nucleic Acids of all types (e.g. bisPNAs, gamma-PNAs), transcription activator-like effector nucleases (TALENs), clustered regularly interspaced short palindromic repeats (CRISPRs), or aptamers (e.g., DNA, RNA, protein, or combinations thereof).

In some aspects, the payload binding domains are one or more of DNA binding proteins (e.g., zinc finger proteins), antibody fragments (Fab), chemically synthesized binders (e.g., PNA, LNA, TALENS, or CRISPR), or a chemical modification (i.e., reactive moieties) in the synthetic polymer scaffold (e.g., thiolate, biotin, amines, carboxylates).

In some embodiments, the one or more features comprises one or more features in the polynucleotide. In some embodiments, the one or more features in the polynucleotide comprises one or more modifications to the polynucleotide. In some embodiments, the one or more modifications comprises DNA methylation (e.g. 5mC, 5hmC, e.g., at CpG dinucleotides, 5 mA, and the like). In some embodiments, the one or more features in the polynucleotide comprise sequence variations, mutations, or larger structural variations. In some embodiments, the one or more features in the polynucleotide comprises rearrangements, deletions, insertions, and/or translocations to the polynucleotide sequence.

In some embodiments, the one or more features comprises one or more features on the polynucleotide. In some embodiments, the one or more features on the polynucleotide comprises a modification to the polynucleotide. In some embodiments, the modification comprises a molecule bound to a monomer. In some embodiments, the one or more features on the polynucleotide comprises one or more molecules bound to the polynucleotide. In some embodiments, the modification comprises the binding of a molecule to the polynucleotide. For instance, for a DNA molecule, the bound molecule can be a DNA-binding protein, such as RecA, NF-κB and p53. In some embodiments, the modification is a particle that binds to a particular monomer or fragment. For instance, quantum dots or fluorescent labels bound to a particular DNA site for the purpose of genotyping or DNA mapping can be detected by the device.

In some embodiments, the polynucleotide sequence comprises one or more nick sites. As a non-limiting example, a nicking restriction endonuclease introduces a nick at the recognition sequence for bar coding. This sequence appears many times in a genome. A single azide azide $N_3$ labeled nucleotide is introduced at the nick site. The reaction is filtered to remove unincorporated nucleotide. A DNA molecule labeled with a DCBO either 5', 3', or body labeled is added to the reaction. The DNA molecule is covalently linked at the nick site via copperless click chemistry. 1000-10000 fold excess DNA molecule can be used. In another non-limiting example, a Cas9 D10A nickase can be used for site-specific labeling. Cas9-D10A is target to a specific site and a single strand nick is introduced. Cas9 D10A is removed. A single azide $N_3$ nucleotide is introduced at the nick site by nick translation. The reaction is filtered to remove unincorporated nucleotide. A DNA molecule labeled with a DCBO either 5', 3', or body labeled is added to the reaction. The DNA molecule is covalently linked at the nick site via copperless click chemistry. 1000-10000 fold excess DNA molecule can be used.

In one embodiment, a nanopore device includes a plurality of chambers, each chamber in communication with an adjacent chamber through at least one pore.

In some embodiments, a nanopore device can be a multipore device having more than one pore. In some embodiments, a nanopore device can include two nanopores, where a first nanopore is positioned relative to a second nanopore in a manner so as to allow at least a portion of a target polynucleotide to move out of the first nanopore and into the second nanopore. In some embodiments, the nanopore device includes one or more sensors at each nanopore, where a respective sensor is capable of identifying a target polynucleotide during the movement across at least one of the nanopores. In some embodiments, the identification entails identifying individual components of the target polynucleotide. In some embodiments, the identification entails identifying payload molecules bound to the target polynucleotide. When a single sensor is employed, the single sensor may include two electrodes placed at both ends of a pore to measure an ionic current across the pore. In another embodiment, the single sensor comprises a component other than electrodes.

In some embodiments, a nanopore device includes three chambers connected through two pores. Devices with more than three chambers can be readily designed to include one or more additional chambers on either side of a three-chamber device, or between any two of the three chambers. Likewise, more than two nanopores can be included in the device to connect the chambers. In some embodiments, the chamber is connected to a common ground relative to the two voltages.

In one aspect, there can be two or more pores between two adjacent chambers, to allow multiple polymer scaffolds to move from one chamber to the next simultaneously. Such a multi-pore design can enhance throughput of target polynucleotide analysis in the device. For multiplexing, one chamber could have a one type of target polynucleotide, and another chamber could have another target polynucleotide type.

In some aspects, the device further includes means to move a target polynucleotide from one chamber to another. In one aspect, the movement results in loading the target polynucleotide (e.g., the amplification product or amplicon comprising the target sequence) across both the first pore and the second pore at the same time. In another aspect, the means further enables the movement of the target polynucleotide, through both pores, in the same direction.

While some variations of nanopore devices are described above, the nanopore device(s) can be configured as described in U.S. Application Publication. No. 2013-0233709, U.S. Pat. No. 9,863,912, and PCT Application Publication No. WO2018/236673, which are hereby incorporated by reference in their entirety.

System and Devices—Sensors

As discussed above, in various aspects, the nanopore device further includes one or more sensors that generate electrical signals corresponding to materials passing through a nanopore.

The sensors used in a nanopore device can include any sensor suitable for identifying a target polynucleotide amplicon bound or unbound to a payload molecule. For instance, a sensor can be configured to identify the target polynucleotide by measuring a current, a voltage, a pH value, an optical feature, or residence time associated with the polymer. In other aspects, the sensor may be configured to identify one or more individual components of the target polynucleotide or one or more components bound or attached to the target polynucleotide. The sensor may be formed of any component configured to detect a change in a measurable parameter where the change is indicative of the target polynucleotide, a component of the target polynucleotide, or in some cases, a component bound or attached to the target polynucleotide. In one aspect, the sensor includes a pair of electrodes placed at two sides of a pore to measure an ionic current across the pore when a molecule or other entity, in particular a target polynucleotide, moves through the pore. In certain aspects, the ionic current across the pore changes measurably when a target polynucleotide segment passing through the pore is bound to a payload molecule. Such changes in current may vary in predictable, measurable ways corresponding with, for example, the presence, absence, and/or size of the target polynucleotide molecule present.

In one embodiment, the sensor comprises electrodes that apply voltage and are used to measure current across the nanopore. Translocations of molecules through the nanopore provides electrical impedance (Z) which affects current through the nanopore according to Ohm's Law, $V=IZ$, where V is voltage applied, I is current through the nanopore, and Z is impedance. Inversely, the conductance $G=1/Z$ are monitored to signal and quantitate nanopore events. The result when a molecule translocates through a nanopore in an electrical field (e.g., under an applied voltage) is a current signature that may be correlated to the molecule passing through the nanopore upon further analysis of the current signal.

When residence time measurements from the current signature are used, the size of the component can be correlated to the specific component based on the length of time it takes to pass through the sensing device.

In one embodiment, a sensor is provided in the nanopore device that measures an optical feature of the polymer, a component (or unit) of the polymer, or a component bound or attached to the polymer. One example of such measurement includes the identification of an absorption band unique to a particular unit by infrared (or ultraviolet) spectroscopy.

In some embodiments, the sensor is an electric sensor. In some embodiments, the sensor detects a fluorescent signature. A radiation source at the outlet of the pore can be used to detect that signature. Non-limiting examples of sensor circuitry in the nanopore device can be found in PCT Application Publication No. WO/2018/236673, which is hereby incorporated by reference in its entirety.

System and Devices—Processor, Controller, and Other Elements

As described above, embodiments system of the present disclosure are configured to interface with the set of one or more nanopore devices and include an electronics subsystem for receiving electrical signals from the sensors of the set of nanopore devices and for creating a local map, a global map, and/or a consensus map of one or more features of a molecule, for example, in real-time (e.g., by modulating voltage applied across a nanopore, and scanning and surveying various regions across the molecule). The electrical subsystem can include signal processing elements (e.g., amplifiers, filters, signal pre-conditioning elements, etc.) and/or elements for controlling voltage applied across different nanopores, in order to enable automated detection and mapping of one or more features across various regions of the molecule in the nanopore device.

Aspects of the present disclosure includes a device comprising a processor. In some embodiments, the device comprises a non-transitory computer-readable medium comprising instructions that cause the processor to determine, from the one or more sensors, the simultaneous presence of the target polynucleotide in both pores. In some embodiments, the instructions cause the processor to scan for one or more features of the target polynucleotide. In some embodiments, the instructions cause the processor to count the first set of features in the first cycle in the first direction, and, responsive to that count, adjust one or both of the first and second voltages, to produce a first force and an opposing second force acting on said target polynucleotide. In some embodiments, the first and second forces change the direction and the speed of the movement of the target polynucleotide so that at least a portion of the target polynucleotide moves from the second pore to the first pore in the second direction. In some embodiments, the process is repeated to detect a second set of features, in a second cycle. In some embodiments, the process to detect third and fourth sets of features, in a second cycle. In some embodiments, the steps are repeated until the polynucleotide exits the dual-pore device.

In some embodiments, the computer-readable medium further comprises instructions that cause the processor to build a local map of a region of the polynucleotide containing the one or more features based on the scans. In some embodiments, the computer-readable medium further comprises instructions that cause the processor to build a consensus map of a region of the polynucleotide containing the one or more features based on the scans. In some embodiments, building comprises a machine learning algorithm that is trained to detect one or more features based on training data and probabilistic models, that will be described in further detail below.

Aspects of the present disclosure include a device that comprises a controller. In some embodiments, the controller is a field programmable gate array (FPGA). In some embodiments, the controller is configured to control the number of features to scan for. In some embodiments, the controller is configured to control the number of features to re-scan. In some embodiments, the controller is configured to control the movement of the target polynucleotide. In some embodiments, the controller is configured to control the direction of the target polynucleotide. In some embodiments, the controller determines which of the one or more features to perform additional scans on. In some embodiments, the controller determines when to move away from one or more features already detected. In some embodiments, the controller determines when to scan for regions on the polynucleotide that have not yet been scanned. In some embodiments, the FPGA executes control logic to change the: a) number of features to scan for; b) number of features to re-scan; c) movement or direction of the target polynucleotide; d) direction of the target polynucleotide; or e) a combination thereof.

In some embodiments, the processor and computer-readable medium comprising instructions cause the processor to carry out the functions instructed by the controller (e.g. number of features to scan for; number of features to re-scan; movement of the target polynucleotide; direction of the target polynucleotide; and/or a combination thereof). In some embodiments, the processor is a field programmable gate array (FPGA) or an application-specific integrated circuit (ASIC).

In some embodiments, the controller, a processor, and a non-transitory computer-readable medium comprising instructions that cause the processor to: change the direction of the target polynucleotide when a first set of probes is detected. In some embodiments, the first voltage and the second voltage is adjusted in real-time, wherein said adjusting is performed by an active feedback controller using hardware and software. In some embodiments, the controller is configured to control the first or second voltage based on feedback of the first or second or both ionic current measurements.

Embodiments of the device and system can also include a processor including architecture with logic for implementing a set of operation modes including a first operation mode for measuring and evaluating a set of metrics derived from received electrical signals associated with one or more features of the molecule, a second operation mode for generating an assessment of the one or more features upon processing values of the set of metrics, and a third operation mode for executing one or more actions to continue scanning the same region of the molecule to search for additional features, continue scanning the same region of the molecule for re-scanning of the same probes already detected, vary the number of probes to scan in the same region, or move to a different region of the molecule for scanning, based upon the assessment. As such, the system can include structures for implementing embodiments of the method(s) described in more detail below.

The device and system can also generate notifications for provision to an operator of the system. The notifications can include content describing one or more of: a status of the system a status of one or more nanopore devices interfacing with control elements of the system, a status of one or more nanopores, instructions for adjusting operation of the system, instructions for proceeding with an experimental protocol in relation to nanopore/nanopore device status, and other content. The notifications can be rendered by the system in a visual format (e.g., using a display), an audible format (e.g., using a speaker), haptically (e.g., using a haptic device), and/or in another other suitable format.

The device and system can also generate computer-readable instructions for transitioning between different system operation modes (e.g., transitioning to an idle mode, transitioning to a "stop experiment" mode, transitioning to a "resume experiment" mode, transitioning to a calibration mode, transitioning to a mode involving use\ of a subset of nanopores still having suitable quality, etc.).\ in relation to nanopore/nanopore device status. The computer-readable instructions can be transmitted to a controller of the system, in order to transition the system between operation modes.

An embodiment of a machine learning architecture associated with embodiments of the systems and methods described "learns" when to move from one location to another on a target polynucleotide, when to continuously scan one or more features, when to vary the number of features to scan, and when to switch from continuously scanning one or more features to moving further away from the one or more features already scanned to a location that has not yet been surveyed/scanned, in a polynucleotide. The automation goal is to generate a sufficiently informative data set so as to build a consensus map for each molecule (i.e. polynucleotide). For example, a machine learning architecture with control logic can provide for scanning a region of a molecule for a period of time, build a local map of that region in real-time, and then move to a different location that has not yet been scanned to build a consensus map for the molecule. In an example, Bayesian Optimization, which is operable on hardware with limited processing power that needs to react at/near real time can be used. While Bayesian optimization is described, other statistical and/or machine learning approaches can be used to for automated searching and surveying for molecule map generation. In variations, such models can implement a learning style including unsupervised learning (e.g., using K-means clustering), supervised learning (e.g., using regression, using back propagation networks), semi-supervised learning, reinforcement learning, or any other suitable learning style.

The device and system can additionally or alternatively implement any one or more of: a regression algorithm (e.g., least squares, logistic, stepwise, multivariate adaptive, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method, a kernel method (e.g., a support vector machine, a radial basis function, a linear discriminate analysis, etc.), a clustering method (e.g., k-means clustering, expectation maximization, etc.), an associated rule learning algorithm (e.g., an Eclat algorithm, etc.), a neural network, a deep learning algorithm, a dimensionality reduction method (e.g., principal component analysis, partial least squares regression, etc.), an ensemble method (e.g., boosting, boostrapped aggregation, AdaBoost, stacked generalization, gradient boosting machine method, random forest method, etc.), and any suitable form of algorithm.

Applications of such algorithms for automated searching and surveying for map generation of a molecule, are described in more detail below.

In some aspects, the device and systems of the present disclosure include a non-transitory computer-readable medium, comprising instructions that cause a processor to: i) determine, from the sensor, the simultaneous presence of the target polynucleotide in both pores; ii) scan for one or more features of the target polynucleotide; iii) count the first set of features in the first cycle in the first direction, and, responsive to that count, adjust one or both of the first and second voltages, to produce a first force and an opposing second force acting on said target polynucleotide, wherein said first and second forces change the direction and the speed of the movement of the target polynucleotide so that at least a portion of the target polynucleotide moves from the second pore to the first pore in the second direction; and iv) repeat steps i) through iii) to detect a third and fourth set of features, in a second cycle.

In some aspects, the device and systems of the present disclosure comprise a controller. In some embodiments, the controller is a field programmable gate array (FPGA) or an application-specific integrated circuit (ASIC).

Aspects of the present disclosure include a device for carrying out the functions of the methods described herein. The present disclosure includes a device for mapping one or more features of a polynucleotide sequence of a target polynucleotide through a first and a second pore, the device comprising: (i) an electrode connected configured to provide a first voltage at the first pore of the device, and provide a second voltage at the second pore of the device; (ii) a first pore; (iii) a second pore; wherein the first pore and the second pore are configured such that the target polynucleotide is capable of simultaneously moving across both pores in a first direction or a second direction, and in a controlled manner; (iv) one or more sensors capable of identifying: a first set of features, in a first cycle, from the target polynucleotide, during movement of the target polynucleotide through the first pore and the second pore in the first direction and, a second set of features, in the first cycle, from the target polynucleotide, during movement of the target polynucleotide through the second pore and the first pore in the second direction; (v) a processor; and (vi) a non-transitory computer-readable medium comprising instructions that cause the processor to: a) determine, from the one or more sensors, the simultaneous presence of the target polynucleotide in both pores; b) scan for one or more features of the target polynucleotide; c) count the first set of features in the first cycle in the first direction, and, responsive to that count, adjust one or both of the first and second voltages, to produce a first force and an opposing second force acting on said target polynucleotide, wherein said first and second forces change the direction and the speed of the movement of the target polynucleotide so that at least a portion of the target polynucleotide moves from the second pore to the first pore in the second direction; and d) repeat steps a) through c) to detect a third and fourth set of features, in a second cycle.

In some cases, the instructions further cause the processor to repeat c) until the target polynucleotide exits the device. In some cases, the first pore and the second pore are about 10 nm to about 2 μm apart from each other.

In some cases, the diameter of the pores ranges from about 2 nm to about 50 nm. In some cases, the diameter of the pore is about 20 nm. In some cases, the diameter of the first and/or second pore ranges from about 2 nm to about 50 nm. In some cases, the diameter of the first and/or second pore ranges from about 2 nm to about 8 nm. In some cases, the diameter of the first and/or second pore ranges from about 10 nm to about 20 nm. In some cases, the diameter of the pore ranges from about 20 nm to about 30 nm. In some cases, the diameter of the first and/or second pore ranges from about 30 nm to about 40 nm. In some cases, the diameter of the first and/or second pore ranges from about 40 nm to about 50 nm. In some cases, the diameter of the first and/or second pore is about 2 nm, about 4 nm, about 6 nm, about 8 nm, about 10 nm, about 12 nm, about 14 nm, about 16 nm, about 18 nm, about 20 nm, about 22 nm, about 24 nm, about 26 nm, about 28 nm, about 30 nm, about 32 nm, about 34 nm, about 36 nm, about 38 nm, about 40 nm, about 42 nm, about 44 nm, about 46 nm, about 48 nm, or about 50 nm. In some cases, the diameter of the first and/or second pore is about 19 nm. In some cases, the first pore and the second pore have the same diameters. In some cases, the diameter of the first and/or second pore is about 21 nm. In some cases, the diameter of the first and/or second pore is about 22 nm. In some cases, the diameter of the first and/or second pore is about 23 nm. In some cases, the diameter of the first and/or second pore is about 24 nm. In some cases, the diameter of the first and/or second pore is about 25 nm. In some cases, the diameter of the first and/or second pore is about 27 nm. In some cases, the diameter of the first and/or second pore is about 29 nm. In some cases, the first pore and the second pore have different diameters. In some cases, the diameter of the pore is about 20 nm.

In some cases, the first pore and the second pore are about 500 nm apart from each other. In some cases, the first pore has a depth of at least about 0.3 nm separating the first channel and the chamber and the second pore has a depth of at least about 0.3 nm separating the chamber and the second channel. In some cases, the chamber is connected to a common ground relative to the two voltages.

In some cases, the device further comprises a controller. In some cases, the controller is configured to vary the number of features of the polynucleotide to scan. In some cases, the controller is configured to vary the number of scans. In some cases, the controller is configured to control the location of the polynucleotide that is scanned. In some cases, the controller is configured to change the region of the polynucleotide that is scanned. In some cases, the controller is configured to control the: a) number of features to scan for; b) number of features to re-scan; c) type of features to scan or re-scan for; d) number of cycles to scan or re-scan for; e) movement of the target polynucleotide; f) direction of the target polynucleotide; g) speed of the target polynucleotide; h) voltage of the first and second pore; or i) a combination thereof.

In some cases, the processor comprises a field programmable gate array (FPGA) or an application-specific integrated circuit (ASIC). In some cases, the controller comprises a field programmable gate array (FPGA) or an application-specific integrated circuit (ASIC). In some cases, the controller is a microcontroller.

In some cases, the FPGA or ASIC executes control logic to change the: a) number of features to scan for; b) number of features to re-scan; c) type of features to scan or re-scan for; d) number of cycles to scan or re-scan for; e) movement of the target polynucleotide; f) direction of the target polynucleotide; g) speed of the target polynucleotide; h) voltage of the first and second pore; or i) a combination thereof.

In some cases, the controller is configured to control the direction of movement of the polynucleotide. In some cases, the device further comprises instructions that cause the processor to build a local map of a region of the polynucleotide containing the one or more features based on the scans. In some cases, the device further comprises instructions that cause the processor to build a consensus map of a region of the polynucleotide containing the one or more features based on the scans. In some cases, building comprises a machine learning algorithm that is trained to detect one or more features based on training data and probabilistic models. In some cases, the device further comprises instructions that cause the processor to compute the speed of a feature of the target polynucleotide from the time difference between detection of the feature in the first pore and the second pore, and the known distance between pore one and pore two.

In some cases, the device further comprises instructions that cause the processor to compute the distances between features from the speed of a feature of the target polynucleotide, from the time between features detected in the current signal from the first pore, the second pore, or both. In some cases, the device further comprises instructions that cause the processor to compute the speed of a feature of the target polynucleotide for every scan, and to compute statistics on the speed of the feature by using the distribution of speeds. In some cases, the device further comprises instructions that cause the processor to combine the speed of all the features and compute the time history of the speed of the polynucleotide in a given scan and given direction of scanning.

In some cases, the device further comprises instructions that cause the processor to perform a frequency sweep of the polynucleotide in the first direction, second direction, or both. In some cases, the device further comprises instructions that cause the processor to perform an amplitude sweep of the polynucleotide in the first direction, second direction, or both. In some cases, the device further comprises instructions that cause the processor to adjust the speed of the polynucleotide. In some cases, wherein the speed ranges from 1 base pair per millisecond to 10 base pairs per millisecond.

In some cases, the device further comprises instructions cause the processor to adjust the first and second voltages in order to perform a plurality of scans of the polynucleotide at a plurality of speeds. In some cases, said performing the plurality of scans of the polynucleotide at the plurality of speeds improves the accuracy of the detection of one or more features. In some cases, the device further comprises instructions that cause the processor perform a plurality of scans of the polynucleotide at a plurality of speeds. In some cases, the device further comprises instructions that cause the processor to control the speed range of the polynucleotide in the first direction, second direction, or both. In some cases, the device further comprises instructions that cause the processor to control the voltage range of the first and second pores when the polynucleotide moves through the first and second pore in the first direction, second direction, or both. In some cases, the device further comprises instructions that cause the processor to determine an optimal speed range of the polynucleotide in the first direction, second direction, or both, wherein the optimal speed range of the polynucleotide reduces the effect of Brownian motion on the polynucleotide.

In some cases, controlling the speed range of the polynucleotide comprises determining the optimal speed range of the polynucleotide for sequencing.

In some cases, the target polynucleotide is substantially linearized. In some cases, the target polynucleotide is substantially linearized by the action of the adjustments to the first voltage, or the second voltage, or both.

Aspects of the present disclosure include systems for carrying out the methods disclosed herein. The system comprises a) a dual-pore, dual-amplifier device for mapping one or more features of a polynucleotide sequence of a target polynucleotide through a first and a second pore, the device comprising: (i) an electrode connected to a power supply configured to provide a first voltage at the first pore of the device, and provide a second voltage at the second pore of the device; (ii) a first pore; (iii) a second pore; wherein the first pore and the second pore are configured such that the target polynucleotide is capable of simultaneously moving across both pores in a first direction or a second direction, and in a controlled manner; (iv) one or more sensors capable of identifying: a first set of features, in a first cycle, from the target polynucleotide, during movement of the target polynucleotide through the first pore and the second pore in the first direction and, a second set of features, in the first cycle, from the target polynucleotide, during movement of the target polynucleotide through the second pore and the first pore in the second direction; c) a processor; and d) a non-transitory computer-readable medium, comprising instructions that cause the processor to: i) determine, from the sensor, the simultaneous presence of the target polynucleotide in both pores; ii) scan for one or more features of the target polynucleotide; iii) count the first set of features in the first cycle in the first direction, and, responsive to that count, adjust one or both of the first and second voltages, to produce a first force and an opposing second force acting on said target polynucleotide, wherein said first and second forces change the direction and the speed of the movement of the target polynucleotide so that at least a portion of the target polynucleotide moves from the second pore to the first pore in the second direction; and iv) repeat steps i) through iii) to detect a third and fourth set of features, in a second cycle.

In some cases, the device further comprises a controller. In some cases, the controller is configured to vary the number of features of the polynucleotide to scan. In some cases, the controller is configured to vary the number of scans. In some cases, the controller is configured to control the location of the molecule that is scanned. In some cases, the controller is configured to control the: a) number of features to scan for; b) number of features to re-scan; c) type of features to scan or re-scan for; d) number of cycles to scan or re-scan for; e) movement of the target polynucleotide; f) direction of the target polynucleotide; g) speed of the target polynucleotide; h) voltage of the first and second pore; or i) a combination thereof.

In some cases, the processor comprises a field programmable gate array (FPGA) or an application-specific integrated circuit (ASIC). In some cases, the controller comprises a field programmable gate array (FPGA) or an application-specific integrated circuit (ASIC). In some cases, the controller is a microcontroller. In some cases, the FPGA or ASIC executes control logic to change the: a) number of features to scan for; b) number of features to re-scan; c) type of features to scan or re-scan for; d) number of cycles to scan or re-scan for; e) movement of the target polynucleotide; f) direction of the target polynucleotide; g) speed of the target polynucleotide; h) voltage of the first and second pore; or i) a combination thereof.

In some cases, the controller is configured to change the direction of the molecule that is scanned.

In some cases, the system further comprises instructions that cause the processor to build a local map of a region of the polynucleotide containing the one or more features based on the scans. In some cases, the system further comprises instructions that cause the processor to build a consensus map of a region of the polynucleotide containing the one or more features based on the scans. In some cases, building comprises a machine learning algorithm that is trained to detect one or more features based on training data and probabilistic models.

In some cases, the system further comprises instructions that cause the processor to compute the speed of a feature of the target polynucleotide from the time difference between detection of the feature in the first pore and the second pore, and the known distance between pore one and pore two. In some cases, the system further comprises instructions that cause the processor to compute the distances between features from the speed of a feature of the target polynucleotide, from the time between features detected in the current signal from the first pore, the second pore, or both. In some cases, the system further comprises instructions that cause the processor to compute speed of a feature of the target polynucleotide for every scan, and to compute statistics on the speed of the feature by using the distribution of speeds. In some cases, the system further comprises instructions that cause the processor to perform a frequency sweep of the polynucleotide in the first direction, second direction, or both. In some cases, the system further comprises instructions that cause the processor to perform an amplitude sweep of the polynucleotide in the first direction, second direction, or both. In some cases, the system further comprises instructions that cause the processor to adjust the speed of the polynucleotide.

In some cases, the speed ranges from 1 base pair per millisecond to 10 base pairs per millisecond.

In some cases, the system further comprises instructions that cause the processor to adjust the first and second voltages in order to perform a plurality of scans of the polynucleotide at a plurality of speeds. In some cases, performing the plurality of scans of the polynucleotide at the plurality of speeds improves the accuracy of the detection of one or more features.

In some cases, the system further comprises instructions that cause the processor perform a plurality of scans of the polynucleotide at a plurality of speeds. In some cases, the system further comprises instructions that cause the processor to control the speed range of the polynucleotide in the first direction, second direction, or both. In some cases, the system further comprises instructions that cause the processor to control the voltage range of the first and second pores when the polynucleotide moves through the first and second pore in the first direction, second direction, or both.

In some cases, the system further comprises instructions that cause the processor to determine an optimal speed range of the polynucleotide in the first direction, second direction, or both, wherein the optimal speed range of the polynucleotide reduces the effect of Brownian motion on the polynucleotide. In some cases, adjusting voltages to create multiple scans at multiple different speeds improves the comprehensiveness of the data to which to map features. For example, at high speeds (i.e. when the voltage differential is larger), the molecules (e.g., polynucleotide, payload molecule, etc.) is more likely to be deterministic and the molecule is less affected by Brownian motion (e.g. Brownian motion will "pollute" the scanning data less). In some cases, the system determines the optimal speed at which one or more features can be detected before the molecule escapes the device or reverses direction. In some cases, the system further comprises instructions that cause the processor to determine the maximal speed at which Brownian motion least effects the molecule (e.g. maximal speed where Brownian motion is reduced). In some cases, the one or more features are charged so that they perturb the force and therefore the motion when the polynucleotide passes through the pores.

In some cases, controlling the speed range of the polynucleotide comprises determining the optimal speed range of the polynucleotide for sequencing.

In some cases, the system further comprises instructions that cause the processor to combine the speed of all the features and compute the time history of the speed of the polynucleotide in a given scan and given direction of scanning.

In some cases, the target polynucleotide is substantially linearized. In some cases, the target polynucleotide is substantially linearized by the action of the adjustments to the first voltage, or the second voltage, or both.

Aspects of the present disclosure include a dual-pore, dual-amplifier device for sequencing a polynucleotide sequence of a target polynucleotide through a first and a second pore, the device comprising: (i) an electrode connected configured to provide a first voltage at the first pore of the device, and provide a second voltage at the second pore of the device; (ii) the first pore; (iii) the second pore; wherein the first pore and the second pore are configured such that the target polynucleotide is capable of simultaneously moving across both pores in a first direction or a second direction, and in a controlled manner; (iv) one or more sensors capable of identifying: a first set of primers, in a first cycle, from the target polynucleotide, during movement of the target polynucleotide through the first pore and the second pore in the first direction and, a second set of primers, in the first cycle, from the target polynucleotide, during movement of the target polynucleotide through the second pore and the first pore in the second direction; (v) a processor; and (vi) a non-transitory computer-readable medium comprising instructions that cause the processor to: a) determine, from the one or more sensors, the simultaneous presence of the target polynucleotide in both pores; b) scan for one or more primers hybridized to the target polynucleotide; c) detect, in a first cycle, the first set of primers when the target polynucleotide is in both pores in the first direction; d) re-scan for the one or more primers hybridized to the target polynucleotide; e) when the first set of primers are detected in the first cycle in the first direction, adjust the first voltage, the second voltage, or both, to the first and second pore to change the direction of the target polynucleotide so that at least a portion of the target polynucleotide moves from the second pore to the first pore in the second direction, f) detect, in the first cycle, the presence of the second set of primers when the target polynucleotide is in both pores simultaneously in the second direction; g) identify each nucleotide of the polynucleotide that passes through one of the pores, by measuring an ionic current across the pore when the nucleotide passes that pore; and h) repeating steps a) through g) to detect a third and fourth set of primers, in a second cycle.

Aspects of the present disclosure include a system comprising: a) a dual-pore, dual-amplifier device for mapping one or more features of a polynucleotide sequence of a target polynucleotide through a first and a second pore, the device comprising: (i) an electrode connected configured to provide a first voltage at the first pore of the device, and provide a second voltage at the second pore of the device; (ii) a first pore; (iii) a second pore; wherein the first pore and the second pore are configured such that the target polynucleotide is capable of simultaneously moving across both pores in a first direction or a second direction, and in a controlled manner; (iv) one or more sensors capable of identifying: a first set of primers, in a first cycle, from the target polynucleotide, during movement of the target polynucleotide through the first pore and the second pore in the first direction and, a second set of primers, in the first cycle, from the target polynucleotide, during movement of the target polynucleotide through the second pore and the first pore in the second direction; c) a processor; and d) a non-transitory computer-readable medium, comprising instructions that cause the processor to: i) determine, from the one or more sensors, the simultaneous presence of the target polynucleotide in both pores; ii) scan for one or more primers hybridized to the target polynucleotide; iii) detect, in the first cycle, the first set of primers when the target polynucleotide is in both pores in the first direction; iv) re-scan for the one or more primers hybridized to the target polynucleotide; v) when the first set of primers are detected in the first cycle in the first direction, adjust the first voltage, the second voltage, or both, to the first and second pore to change the direction of the target polynucleotide so that at least a portion of the target polynucleotide moves from the second pore to the first pore in the second direction, vi) detect, in the first cycle, the presence of the second set of primers when the target polynucleotide is in both pores simultaneously in the second direction; vii) identify each nucleotide of the polynucleotide that passes through one of the pores, by measuring an ionic current across the pore when the nucleotide passes that pore; and viii) repeating steps i) through vii) to detect a third and fourth set of primers, in a second cycle.

Map Generation of One or More Features in a Molecule

In relation to adaptive logic, a goal is to identify one or more features of a target polynucleotide and create a local and/or global consensus map of the one or more features of a target polynucleotide. An adaptive controller could vary the number of features to look for, which features and locations on the molecule to re-scan (e.g. using bidirectional scanning), and/or when to move to a different location that has not yet been surveyed in near real time. The adaptive controller can create a real-time local map of the one or more features, and produce a data set for creating a consensus map of the entire molecule. In implementing machine learning algorithms, a model can be trained with training data associated with the following metrics (described above): IRMS, Baseline drift, Baseline up-down motion, LFNP, and other metrics. The model can then be used to determine combinations of metrics indicating a probability of when to change the molecule's translocation direction in response to detecting passage of molecular features and to automatically produce the best intervening actions for different types of characteristic deviations. Using active logic based on a Field-Programmable Gate Array (FPGA) or an application-specific integrated circuit (ASIC), the molecule's translocation direction can be changed in response to detecting passage of molecular features. This enables back-and-forth rescanning of a local DNA region that can be used to increase precision through averaging.

The system can use machine learning techniques to generate a prior distribution of "events" for a specific type of experiment/reagent, generate characterizations (e.g., in relation to values of metrics) for all the types of molecular detections, and generate characterizations for other deviations (e.g., such as deviations in properties of a reagent that change over time, etc.). Training data can be derived from, for example, real-time feedback of event signatures for each molecular motif, model accuracy, false-positive/false-negative of molecule calls, fraction of CpG's correctly called per molecule, CpG distance/mapping prediction performance, fractional predictions of 5hmC vs. 5mC, genomic distance predictions, distance between molecular motifs, and molecular motif density. The model can be developed with a supervised learning approach that uses algorithms to process tagged deviations or other aspects in the training data, and bin them into types of excursions. The system can also collect data on which intervening actions were appropriate for which characteristic deviation/event.

Once a molecular motif (e.g. one or more features on a polynucleotide and/or one or more features in a polynucleotide) event is detected using the trained model, the system can implement one or more correction actions, including one or more of: toggling polarity of voltage, applying electrical stimuli at specific voltage (and/or with a specific number or rate of instances of zapping), change the voltage to change the direction of the molecule for re-scan, changing the location of the molecule at which surveying/scanning is performed, changing the number of molecular motifs to survey/scan, or performing no action (e.g., with a notification to an operating entity).

Consensus Mapping with Deep Learning

Another approach is to use a signal processing convolutional neural network to identify electronically distinct molecular motifs, and the location of and spacing between the distinct molecular motifs, and feed that into a deep Q learning algorithm to develop a continuously improving adaptive logic and consensus mapping. This technique improves future decision making by the system of automated searching and surveying of molecules for map generation.

Additional Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

Methods—Extended Recapture of a Polynucleotide in a Nanopore Device

The present disclosure provides methods for recapturing a polynucleotide in a nanopore device. The system and devices of the present disclosure carry out the methods for recapturing the target polynucleotide.

Aspects of the present disclosure include methods for recapturing a polynucleotide in a nanopore device, the method comprising providing a nanopore device for controlling the movement of the polynucleotide through one or more pores. In some cases, the device comprises at least a first pore positioned between a chamber and a first fluidic volume, the first pore fluidically connected to the chamber and to the first fluidic volume, the first fluidic volume being a geometrically constrained enclosure with an opening on a side opposite of the first pore. In some cases, the device comprises at least one electrode positioned within the first fluidic volume, wherein the one electrode is configured to provide a first voltage at the first pore. In some cases, the device comprises one or more sensors (e.g. amplifiers) configured for voltage control and current measurement at the first pore. In some cases, the method comprises loading the polynucleotide into the chamber of the device. In some cases, the method comprises loading the polynucleotide into a geometrically constrained fluidic volume of the device. In some cases, the method comprises applying a first voltage across the first pore for moving the polynucleotide from the chamber in a first direction to capture the polynucleotide in the first pore and to allow the polynucleotide to pass through the first pore into the first fluidic volume. In some cases, the method comprises detecting a first ionic current in the first pore when the polynucleotide is passing through the first pore in the first direction. In some cases, the method comprises adjusting voltage to zero for a time period while the polynucleotide is contained within the first fluidic volume. In some cases, the method comprises applying a second voltage to reverse the direction of the polynucleotide positioned in the first fluidic volume, wherein said second voltage moves at least a portion of the polynucleotide in a second direction from the first fluidic volume to recapture the portion of the polynucleotide in the first pore such that the polynucleotide is maintained within the first pore. In some cases, the method comprises detecting a second ionic current in the first pore when the polynucleotide is recaptured in the first pore. In some cases, the device is configured to pass the polynucleotide through the first pore from the chamber and pass through the first pore from the first fluidic channel. In some cases, the method further comprises repeating steps the steps as described herein until the polynucleotide exits the device.

In some cases, the nanopore device further comprises a second pore, a third pore, a fourth pore, a fifth pore, a sixth pore, a seventh pore, an eighth pore, a ninth pore, or a tenth pore. In some cases, the nanopore device comprises two or more pores, three or more pores, four or more pores, five or more pores, six or more pores, seven or pore pores, eight or more pores, nine or more pores, or ten or more pores.

In some cases, the nanopore device comprises a geometrically constrained first fluidic volume and a geometrically constrained second fluidic volume. In some cases, the first and second geometrically constrained volumes are first and second fluidic channels. In some cases, the nanopore device comprises one or more, two or more, three or more, four or more, five or more, six or more, seven or more, eight or more, nine or more, or ten or more geometrically constrained volumes. In some embodiments, the geometrically constraint of the first fluidic channel increases the time period that the first voltage applied at the first pore is maintained. In some embodiments, the geometrically constraint of the first fluidic channel increases the time period that the first voltage applied at the first pore is maintained relative to the geometric constraint of a cavity. In some embodiments, the first voltage applied at the first pore that captures and translocates the polynucleotide through the first pore (e.g. from the chamber of the device through the first pore) is maintained for a time period ranging from 0-1000 milliseconds, 1-20 milliseconds, 20-60 milliseconds, 60-120 milliseconds, 120-150 milliseconds, 150-300 milliseconds, 300-500 milliseconds, 500-1000 milliseconds, 1-20 seconds, 20-60 seconds, 60-120 seconds, 120-150 seconds, 150-300 seconds, 300-500 seconds, or 500-1000 seconds. In some embodiments, the first voltage applied at the first pore for capturing and translocates the polynucleotide through the first pore (e.g. from the chamber of the device through the first pore) is maintained for 20 milliseconds or more, 60 milliseconds or more, 120 milliseconds or more, 150 milliseconds or more, 300 milliseconds or more, 500 milliseconds or more, 1000 milliseconds or more, 20 seconds or more, 60 seconds or more, 120 seconds or more, 150 seconds or more, 300 seconds or more, 500 seconds or more, or 1000 seconds or more. In some embodiments, the first voltage is maintained for the time period as described herein after detecting capture and translocation of the polynucleotide through the first pore. In some embodiments, the first voltage is maintained for the time period as described herein before setting the second voltage at the first pore to zero mV.

In some cases, the first fluidic volume is a first fluidic channel. In some cases, the second fluidic volume is a second fluidic channel. In some cases, the shape of a first and/or second fluidic channel can be circular, square, rectangular, hexagonal, triangular, oval, polygon, V-shape, U-shape, or any other suitable shape. In some cases, the first fluidic channel and/or the second fluidic channel each have a V-shape and each have openings on either end of the V-shape, the V-shapes of the first and second fluidic channels arranged on the chip opposite one another with points of the V-shapes being adjacent to each other, and wherein the first nanopore is positioned at the point of the V-shape of the first fluidic channel and the second nanopore is positioned at the point of the V-shape of the second fluidic channel. In some embodiments, each of the fluidic channels is a different shape. The fluidic channels are not limited to the shapes and/or sizes as described herein and can be any shape and/or size as required per conditions specified to its intended use. In some cases, the first fluidic volume comprises a V-shaped channel. In some cases, the first fluidic channel and/or second fluidic channel comprises a geometrically constrained volume.

In some cases, wherein the first fluidic channel and/or second fluidic channel has a length ranging from about 0.05 mm to about 5 mm. In some cases, wherein the first fluidic channel and/or second fluidic channel has a length ranging from about 0.05 mm to about 4 mm. In some cases, the first fluidic channel and/or second fluidic channel has a length ranging from about 0.5 mm, 1 mm, 1.5 mm, 2 mm, 2.5 mm, 3 mm, 3.5 mm, 4 mm, 4.5 mm or 5 mm.

In some cases, wherein the first fluidic channel and/or second fluidic channel has a width ranging from 50-500 µm. In some cases, wherein the first fluidic channel and/or second fluidic channel has a width ranging from 50-100 µm, 100-150 µm, 150-200 µm, 200-250 µm, 250-300 µm, 300-350 µm, 350-400 µm, 400-450 µm, or 450-500 µm. In some cases, the first fluidic channel and/or second fluidic channel has a width of about 50 µm or more, 100 µm or more, 150 µm or more, 200 µm or more, 250 µm or more, 300 µm or more, 350 µm or more, 400 µm or more, 450 µm or more, or 500 µm or more.

In some cases, wherein the first fluidic channel and/or the second fluidic channel has a depth ranging from 0.5 µm to about 2 µm. In some cases, the first fluidic channel and/or the second fluidic channel has a depth ranging from 0.5-1 µm, 1-1.5 µm, or 1.5-2 µm. In some cases, the first fluidic channel and/or second fluidic channel has a depth ranging from about 0.5 µm or more, 1 µm or more, 1.5 µm or more, 2 µm or more, 2.5 µm or more, or 3 µm or more.

In some cases, the first fluidic volume and second fluidic volume each comprise an opening on a side opposite of the first pore and/or second pore, respectively. In some cases, the second pore is fluidically connected to a second fluidic volume, wherein the second fluidic volume being a geometrically constrained enclosure with an opening on a side opposite of the second pore. In some cases, the first fluidic volume and/or second fluidic volume comprises two openings on a side opposite of the first pore and/or second pore. In some cases, two opening in the first fluidic channel is on the same plane and are parallel to each other. In some cases, two opening in the second fluidic channel is on the same plane and are parallel to each other. In some cases, the one or more openings of the first fluidic volume and/or second fluidic volume is configured to allow the polynucleotide to exit the device through the one or more openings. In some cases, the first fluidic volume is configured to allow the polynucleotide to exit the device through the opening. In some cases, the second fluidic volume is configured to allow the polynucleotide to exit the device through the opening.

In some cases, the polynucleotide moves from the chamber through the at least first pore and into the first fluidic volume for a time period ranging from 30 ms to 500 ms or longer. In some cases, the polynucleotide moves from the first fluidic volume through the at least first pore and into the chamber for a time period ranging from 30 ms to 500 ms or longer. In some cases, the first end of the polynucleotide is positioned away from the at least first pore at a distance ranging from 5 microns to 5 millimeters or more. In some cases, the second end of the polynucleotide is positioned away from the at least first pore at a distance ranging from 5 microns to 5 millimeters or more.

In some cases, the polynucleotide is maintained in the first fluidic volume when the first voltage is adjusted to zero for a time period ranging from 0 to 1000 milliseconds, or 0 1000 seconds. In some cases, adjusting the first voltage to the intermediate voltage of 0 mV provides for relaxation of the polynucleotide to its equilibrium conformation.

In some cases, the method prevents exiting of the polynucleotide from the device for a time period ranging from 5 ms to 5 minutes. In some cases, the method prevents exiting of the polynucleotide from the chamber of the device for a time period ranging from 5 ms to 5 minutes. In some cases, the method prevents exiting of the polynucleotide from the first fluidic volume and/or second fluidic volume of the device for a time period ranging from 5 ms to 5 minutes.

In some cases, the chamber is positioned above the first pore. In some cases, the first pore is positioned between the chamber and the first fluidic volume. In some cases, the second pore is positioned between the chamber and the second fluidic volume. In some cases, the second pore is connected to the chamber and the second fluidic volume. In some cases, the chamber is positioned above the first and second pore. In some cases, the chamber is connected to a common ground relative to the first voltage.

In some cases, wherein the first pore has a diameter ranging from about 2 nm to about 50 nm. In some cases, wherein the first pore has a diameter ranging from about 15 nm to about 30 nm. In some cases, the second pore has a diameter ranging from about 2 nm to about 50 nm. In some cases, wherein the second pore has a diameter ranging from about 15 nm to about 30 nm.

In some cases, the first voltage is applied between the first fluidic volume and the chamber. In some cases, the nanopore device comprises at least one electrode positioned within the second fluidic volume, wherein the at least one electrode is configured to provide a third voltage at the at second pore.

In some cases, the nanopore device comprises dual-amplifier electronics configured for voltage control and current measurement at the first pore and the second pore.

In some cases, method further comprises, after detecting a second ionic current, adjusting the first voltage at the first pore and setting a third voltage at the second pore so that at least a portion of the polynucleotide moves through the first pore and the second pore in a third direction, the third direction being from the first pore to the second pore. In some cases, the third voltage is higher than the first voltage.

In some cases, wherein the first voltage is 0 mV. In some cases, the first voltage ranges from 0-1000 mV. In some cases, the first voltage, the second voltage, the third voltage range, and/or fourth voltage, each independently range from 0 mV to 1000 mV. In some cases, adjusting the first voltage, the second voltage, the third voltage and/or fourth voltage each independently range from 0-1000 mV.

In some cases, the polynucleotide is substantially linearized. In some cases, the polynucleotide is substantially linearized by the action of the adjustments to the first voltage, the second voltage, the third voltage, or a combination thereof. In some cases, the polynucleotide is substantially linearized.

In some cases, the method further comprises adjusting the first voltage to the first pore, the third voltage to the second pore, or both, to change the direction of the polynucleotide so that at least a portion of the polynucleotide moves from the second pore through the first pore in a fourth direction, the fourth direction being from the second pore to the first pore. In some cases, said adjusting the first voltage to the first pore, the third voltage to the second pore, or both, so that at least a portion of the polynucleotide moves in the third direction and/or fourth direction is repeated for a time period until the polynucleotide exits the device. In some cases, the third voltage is applied between the chamber and the second fluidic volume of the device. In some cases, the third voltage is applied during a time period ranging from 5 ms to 5 minutes. In some cases, the method further comprises detecting a first set of features on the polynucleotide when the polynucleotide is in both pores in the third direction. In some cases, the method further comprises detecting a second set of features on the polynucleotide when the polynucleotide is in both pores simultaneously in the fourth direction.

In some cases, the method comprises adjusting the first voltage so that the polynucleotide moves through the first pore for a time period ranging from 5 ms to 5 minutes. In some cases, wherein the polynucleotide passes through the first pore, the chamber, and the second pore. In some cases, wherein the polynucleotide passes partially through the first pore, the chamber, and the second pore.

In some cases, the method further comprises detecting a third ionic current at the first pore and a fourth ionic current at the second pore when the polynucleotide is in both pores in the third direction. In some cases, the method further comprises detecting a fifth ionic current at the first pore and a sixth ionic current at the second pore when the polynucleotide is in both pores in the fourth direction.

In some cases, the first voltage creates voltage gradient across the first pore and along the length of the first fluidic volume. In some cases, the third voltage creates voltage gradient across the at second pore and along the length of the second fluidic volume.

In some cases, the resistance of the first fluidic channel is inversely proportional to the first fluidic channel width. In some cases, the resistance of the second fluidic channel is inversely proportional to the second fluidic channel width. In some cases, the resistance of the first fluidic channel and/or the second fluidic channel is proportional to the volume of the first fluidic channel and/or second fluidic channel. In some cases, the resistance of the first fluidic channel and/or second fluidic channel is proportional to the volume of the first fluidic channel and/or second fluidic channel. In some cases, the resistance of the first fluidic channel and/or second fluidic channel is proportional to the radius of the first fluidic channel and/or second fluidic channel. In some cases, the resistance of the first fluidic channel and/or second fluidic channel is proportional to the cross-sectional radius of the first fluidic channel and/or second fluidic channel.

In some cases, polynucleotide is not entropically trapped within the first fluidic volume and/or second fluidic volume. In some cases, polynucleotide is entropically trapped within the first fluidic volume and/or second fluidic volume.

In some cases, the method further comprises controlling, with a controller, when the polynucleotide requires rescanning of the one or more features of the polynucleotide for a second or third time. In some cases, the controller determines which of the one or more features of the polynucleotide to perform additional recapturing of the one or more features in the first direction and/or the second direction, In some cases, the method further comprises moving away from one or more features of the polynucleotide already recaptured.

In some cases, the first voltage, the second voltage, and the third voltage range from 0 mV to 1000 mV. In some cases, the first voltage, the second voltage, and the third voltage range from 0 mV to 100 mV. In some cases, the first voltage, the second voltage, and the third voltage range from 100 mV to 200 mV. In some cases, the first voltage, the second voltage, and the third voltage range from 200 mV to 300 mV. In some cases, the first voltage, the second voltage, and the third voltage range from 300 mV to 400 mV. In some cases, the first voltage, the second voltage, and the third voltage range from 400 mV to 500 mV. In some cases, the first voltage to the first pore is lower than the second voltage. In some cases, the first voltage to the first pore is higher than the second voltage. In some cases, the first voltage to the first pore and the second voltage to the second pore are the same. In some cases, the first voltage to the first pore and the second voltage to the first pore are the same in the first direction. In some cases, the first voltage to the first pore is lower than the second voltage to the first pore in the second direction. In some cases, the first voltage to the first pore is lower than the third voltage to the second pore in the third direction. In some cases, the first voltage to the first pore is higher than the third voltage to the second pore in the fourth direction.

In some cases, the method further comprises controlling the direction of the polynucleotide through the first and/or second pore via a controller, a processor, and a non-transitory computer-readable medium comprising instructions that cause the processor to: change the direction of the polynucleotide. In some cases, wherein the processor comprises a field programmable gate array (FPGA) or an application-specific integrated circuit (ASIC). In some cases, wherein the controller comprises a field programmable gate array (FPGA) or an application-specific integrated circuit (ASIC). In some cases, wherein the controller is a microcontroller.

In some cases, wherein said recapturing provides for detection of the polynucleotide comprising a polynucleotide sequence with a length ranging from 5 base pairs to about 3,000,000 base pairs.

Methods—Flossing and Rescanning for One or More Features

The present disclosure provides methods for mapping one or more features of a polynucleotide sequence of a target polynucleotide bound to a plurality of probes through a pore. The present disclosure further provides methods for differential detection of 5mC and 5hmC regions in a mixed sample containing in one or more polynucleotide sequences that separately moves through a first and a second pore of a nanopore device.

The present disclosure provides an automated method of mapping one or more features of a target polynucleotide. Also provided in the present disclosure are automated methods for sequencing a polynucleotide sequence. Also provided in the present disclosure are methods for differential detection of methylated and non-methylated regions in a polynucleotide sequence. Also provided in the present disclosure are devices and systems for carrying out the methods of the present disclosure.

Aspects of the present disclosure include a method for mapping one or more features of a target polynucleotide, the method comprising the steps of: a) providing a dual-pore, dual-amplifier device for controlling the movement of the target polynucleotide through a first and second pore simultaneously, the device comprising: (i) a first pore, (ii) a second pore, (iii) a power supply configured to provide a first voltage at the first pore, and to provide a second voltage at the second pore, each voltage being independently adjustable, and (v) dual-amplifier electronics configured for independent voltage control and current measurement at each pore, wherein the first and second pores are configured so that the target polynucleotide is capable of simultaneously moving across both pores in a first direction or a second direction, and in a controlled manner, b) loading the target polynucleotide into the device; c) setting an initial first voltage at the first pore and an initial second voltage at the second pore so that at least a portion of the target polynucleotide moves through the first pore and the second pore in the first direction, the first direction being from the first pore to the second pore; d) scanning for one or more features of the target polynucleotide; e) detecting, in a first cycle, a first set of features when the target polynucleotide is in both pores in the first direction; 0 when the first set of features are detected in the first cycle in the first direction, adjusting the first voltage, the second voltage, or both, to the first and second pore to change the direction of the target polynucleotide so that at least a portion of the target polynucleotide moves from the second pore to the first pore in the second direction, the second direction being from the second pore to the first pore, g) detecting, in the first cycle, the presence of a second set of features when the target polynucleotide is in both pores simultaneously in the second direction; and h) repeating steps c) through g) to detect a third and fourth set of features, in a second cycle.

In some cases, the first pore is connected to a first channel and a chamber of the device.

In some cases, the second pore is connected to a chamber and a second channel of the device.

In some cases, the first voltage is applied between a first channel and a chamber, and the second voltage is applied between a chamber and a second channel of the device.

In some cases, detecting a feature of the target polynucleotide is accomplished with the current measurement from the first pore, or the second pore, or both.

In some cases, the method further comprises computing, with a processor, the speed of the one or more features of the target polynucleotide from the time difference between detection of the feature in the first pore and the second pore, and the known distance between the first pore and the second pore.

In some cases, the method further comprises computing, with a processor, the distances between the one or more features by using the computed speed of a feature of the target polynucleotide, from the time between one or more features detected in the current signal from the first pore, the second pore, or both.

In some cases, the method further comprises computing, with a processor, the speed of a feature of the target polynucleotide for every scan.

In some cases, the method further comprises computing, with a processor, the statistics on the speed of the feature using the distribution of speeds for every scan In some cases, the method further comprises computing, with a processor, computing the time history of the speed of the polynucleotide using the speed of all the features in a given scan and given direction of scanning.

In some cases, the target polynucleotide is substantially linearized.

In some cases, the target polynucleotide is substantially linearized by the action of the adjustments to the first voltage, or the second voltage, or both.

In some cases, the method further comprises controlling, with a controller, the: a) number of features to scan for; b) number of features to re-scan; c) type of features to scan or re-scan for; d) number of cycles to scan or re-scan for; e) movement of the target polynucleotide; f) direction of the target polynucleotide; g) speed of the target polynucleotide; or h) a combination thereof.

In some cases, the method further comprises controlling the number of features to scan. In some cases, the controller determines which of the one or more features to perform additional scans on. In some cases, method further comprises moving away from one or more features already scanned. In some cases, the method further comprises scanning for regions on the polynucleotide that have not yet been scanned.

In some cases, method further comprises building, with a processor, a consensus map for each polynucleotide. In some cases, said building occurs in real-time. In some cases, said building comprises a machine learning algorithm that is trained to detect one or more features based on training data and probabilistic models. In some cases, the method further comprises building, with a processor, a local map for each polynucleotide in real-time. In some cases, the method further comprises repeating steps c) through g) until the target polynucleotide exits the pore device.

In some cases, the one or more features comprises: a) one or more payload molecules bound to the polynucleotide; b) one or more payload molecules hybridized to the polynucleotide; c) one of more payload molecules incorporated into the genome of the polynucleotide; d) a molecular motif on a polynucleotide sequence of the target polynucleotide; or e) a combination thereof.

In some cases, the one or more payload molecules is incorporated enzymatically into the genome of the polynucleotide. In some cases, the one or more payload molecules is chemically incorporated into the genome of the polynucleotide. In some cases, the one or more payload molecules is chemically incorporated into the genome of the polynucleotide using click chemistry. In some cases, the method further comprises determining the position of the of the one or more features of the target polynucleotide. In some cases, the method further comprises determining the distance between each of the one or more features of the target polynucleotide. In some cases, the method further comprises determining the distance between each feature in the first set of features of the target polynucleotide. In some cases, the method further comprises determining the distance between each feature in the second set of features of the target polynucleotide.

In some cases, the one or more features comprises the position of: one or more methylation sites; one or more CpG's; or one or more methylation cites and CpG's, on the polynucleotide sequence of the target polynucleotide. In some cases, the one or more features comprises the position of one or more the nucleosomes on the target polynucleotide. In some cases, the one or more features comprises the position of one or more the nucleosomes bound to the target polynucleotide from its native chromatin state, either without or with chemical fixation. In some cases, the one or more features comprises the position of one or more histones comprised within one or more nucleosomes on the target polynucleotide; or modification state and position of one or more histones comprised within one or more nucleosomes on the target polynucleotide.

In some cases, modification state of a histone are comprised within the tails of the histones, comprising: lysine residues that may be acetylated, methylated or coupled to ubiquitin (a large polypeptide chain); arginine residues that may be methylated; serine residues that are phosphorylated; or other modification to the tails comprised within histones comprised within nucleosomes.

In some cases, the method further comprising identifying the one or more features of the target polynucleotide by measuring an ionic current across one of the pores when the plurality of probes pass through the pore.

In some cases, the first cycle comprises one or more scans performed by a processor to detect the first set of features. In some cases, the first cycle comprises two or more scans, three or more scans, four or more scans, five or more scans, six or more scans, seven or more scans, eight or more scans, nine or more scans, or ten or more scans.

In some cases, the first cycle comprises two or more scans, four or more scans, six or more scans, eight or more scans, ten or more scans, twelve or more scans, fourteen or more scans, sixteen or more scans, eighteen or more scans, or twenty or more scans. In some cases, the first cycle comprises five or more scans, ten or more scans, fifteen or more scans, twenty or more scans, twenty-five or more scans, thirty or more scans, thirty-five or more scans, forty or more scans, forty-five or more scans, or fifty or more scans. In some cases, the second cycle comprises one or more scans performed by a processor to detect the third set of features. In some cases, the second cycle comprises two or more scans, three or more scans, four or more scans, five or more scans, six or more scans, seven or more scans, eight or more scans, nine or more scans, or ten or more scans. In some cases, the second cycle comprises two or more scans, four or more scans, six or more scans, eight or more scans, ten or more scans, twelve or more scans, fourteen or more scans, sixteen or more scans, eighteen or more scans, or twenty or more scans. In some cases, the second cycle comprises five or more scans, ten or more scans, fifteen or more scans, twenty or more scans, twenty-five or more scans, thirty or more scans, thirty-five or more scans, forty or more scans, forty-five or more scans, or fifty or more scans. In some cases, first cycle and the second cycle, together, comprise 50 or more scans, 100 or more scans, 150 or more scans, 200 or more scans, 250 or more scans, 300 or more scans, 350 or more scans, 400 or more scans, or 500 or more scans.

In some cases, the method further comprises repeating steps c) through 0 for a third cycle, a fourth cycle, and a fifth cycle; or when the polynucleotide exits the device. In some cases, the first cycle, second cycle, third cycle, fourth cycle, and fifth cycle, together, comprise 50 or more scans, 100 or more scans, 150 or more scans, 200 or more scans, 250 or more scans, 300 or more scans, 350 or more scans, 400 or more scans, or 500 or more scans.

In some cases, the first set of features is one feature or more, two features or more, three features or more, four features or more, five features or more, six features or more, seven features or more, eight features or more, nine features or more, or ten features or more. In some cases, the second set of features is two features, three features, four features, or five features. In some cases, the second set of features are greater than the first set of features. In some cases, the set of features across sets of scans are combined to generate maps of locations and distances between features, for each target polynucleotide.

In some cases, the one or more features comprises a DNA-binding protein.

In some cases, the method further comprises labeling the polynucleotide with a payload molecule at one or more 5-methylcytosines (5mC) regions, one or more 5-hydroxymethylcytosines (5hmC) regions, or one or more 5mC and 5hmC regions on the target polynucleotide. In some cases, the one or more features comprises: a DNA-binding protein; a polypeptide; an anti-DNA antibody; streptavidin; a transcription factor; a histone; a peptide nucleic acid (PNA); a DNA-hairpin; a DNA molecule; an aptamer; a 5-methylcytosines (5mC) region; a 5-hydroxymethylcytosines (5hmC) region; a nucleotide base; two or more nucleotide bases; or a combination thereof.

In some cases, the method further comprises determining the positions of one or more 5-methylcytosines (5mC) on the target polynucleotide. In some cases, the method further comprises determining the positions of one or more 5-hydroxymethylcytosines (5hmC) on the target polynucleotide. In some cases, the method further comprises determining the positions of one or more 5-methylcytosines and one or more 5-hydroxymethylcytosines on the target polynucleotide. In some cases, the method further comprises determining one or more CpG's on a target polynucleotide. In some cases, the polynucleotide sequence has a length ranging from 5 base pairs to about 2,000,000 base pairs. In some cases, the polynucleotide sequence has a length ranging from 100 base pairs to 500 base pairs. In some cases, the polynucleotide sequence has a length ranging from 1 megabases (Mb) to about 2 Mb. In some cases, the DNA molecule is labeled with DCBO. In some cases, the DNA molecule is covalently linked at a nick site on the target polynucleotide. In some cases, the polypeptide is mono-streptavidin (MS) incorporated into a nick site on the polynucleotide sequence.

In some cases, the method further comprises distinguishing between 5mC and 5hmC regions on the polynucleotide. In some cases, the one or more features comprises a molecule selected from the group consisting of: a nucleic acid, a TALEN, a CRISPR, a peptide nucleic acid, and a chemical compound. In some cases, the one or more features comprises a molecule selected from the group consisting of: a deoxyribonucleic acid (DNA), a ribonucleic acid (RNA), a peptide nucleic acid (PNA), a DNA/RNA hybrid, a polypeptide, or any chemically derived polymer.

In some cases, the target polynucleotide is selected from the group consisting of: a double-stranded DNA, a single-stranded DNA, double-stranded RNA, single-stranded RNA, and DNA-RNA hybrid.

In some cases, the method further comprises controlling the direction of the target polynucleotide through the first and second pore via a controller, a processor, and a non-transitory computer-readable medium comprising instructions that cause the processor to: change the direction of the target polynucleotide when a first set of probes is detected. In some cases, adjusting the first voltage and the second voltage occurs in real-time, wherein said adjusting is performed by an active feedback controller using hardware and software.

In some cases, the method further comprises controlling, with a feedback controller, the first or second voltage based on feedback of the first or second or both ionic current measurements. In some cases, the processor comprises a field programmable gate array (FPGA) or an application-specific integrated circuit (ASIC). In some cases, the controller comprises a field programmable gate array (FPGA) or an application-specific integrated circuit (ASIC). In some cases, the controller is a microcontroller. In some cases, the FPGA or ASIC executes control logic to change the: a) number of features to scan for; b) number of features to re-scan; c) type of features to scan or re-scan for; d) number of cycles to scan or re-scan for; e) movement of the target polynucleotide; f) direction of the target polynucleotide; g) speed of the target polynucleotide; h) voltage of the first and second pore; or i) a combination thereof.

In some cases, wherein the first set of features and the second set of features are the same. In some cases, the first set of features and the second set of features are different. A non-limiting example of when the first set of features and the second set of features are different include when the one or more additional features are found in the second set of features that are not in the first set of features. In some cases, the third set of features and the fourth set of features are the same. In some cases, the third set of features and the fourth set of features are different. In some cases, the second set of features is greater than the second set of features.

In some cases, each feature is spaced about from one another by about 100 base pairs, 300 base pairs, 500 base pairs, 1 kilo-base pair, 5 kilo base-pair, 10 kilo base pair, 20 kilo-base pair, or a combination thereof. In some cases, the polynucleotide sequence comprises one or more nick sites. In some cases, each features is spaced about from one another by about 1 base pair or more, about 2 base pairs or more, about 3 base pairs or more, about 4 base pairs or more, about 5 base pairs or more, about 6 base pairs or more, about 7 base pairs or more, about 8 base pairs or more, about 9 base pairs or more, about 10 base pairs or more, about 25 base pairs or more, about 50 base pairs or more, about 100 base pairs or more, about 300 base pairs or more, about 500 base pairs or more, about 1 kilo-base pair or more, about 5 kilo base-pairs or more, about 10 kilo base pairs or more, about 20 kilo-base pairs or more, or a combination thereof.

In some cases, each features is spaced about from one another by about 25 base pairs or less, about 50 base pairs or less, about 100 base pairs or less, about 300 base pairs or less, about 500 base pairs or less, about 1 kilo-base pair or less, about 5 kilo base-pairs or less, about 10 kilo base pairs or less, about 20 kilo-base pairs or less, or a combination thereof.

In some cases, the method further comprises identifying each nucleotide of the polynucleotide that passes through one of the pores, by measuring an ionic current across the pore when the nucleotide passes that pore.

In some cases, the method further comprises sequencing the polynucleotide.

In some cases, the controller is configured to perform a control voltage frequency sweep of the polynucleotide in the first direction, second direction, or both. In some cases, the controller is configured to perform a control voltage amplitude sweep of the polynucleotide in the first direction, second direction, or both. In some cases, the controller is configured to adjust the speed of the polynucleotide. In some cases, the speed ranges from 0.1 base pair per millisecond to 10 base pairs per millisecond. In some cases, the controller is configured to adjust the first and second voltages in order to perform a plurality of scans of the polynucleotide at a plurality of speeds. In some cases, said performing the plurality of scans of the polynucleotide at the plurality of speeds improves the accuracy of the detection of one or more features. In some cases, the method comprises performing a plurality of scans of the polynucleotide at a plurality of speeds. In some cases, the controller is configured to control the speed range of the polynucleotide in the first direction, second direction, or both. In some cases, the controller is configured to control the voltage range of the first and second pores when the polynucleotide moves through the first and second pore in the first direction, second direction, or both. In some cases, the controller is configured to determine an optimal speed range of the polynucleotide in the first direction, second direction, or both, wherein the optimal speed range of the polynucleotide reduces the effect of Brownian motion on the polynucleotide. In some cases, the speed range of the polynucleotide comprises determining the optimal speed of the polynucleotide for sequencing.

Aspects of the present disclosure includes a method for differential detection of 5mC and 5hmC in a mixed sample containing in one or more polynucleotide sequences that separately moves through a first and a second pore, the method comprising: a) labeling 5mC and 5hmC regions on one or more target polynucleotide sequences of one or more target polynucleotides with a binding moiety; b) contacting the one or more target polynucleotides with a payload molecule, wherein the payload molecule is configured to bind to the binding moiety of the one or more target polynucleotides; c) providing a dual-pore, dual-amplifier device for controlling the movement of the target polynucleotide bound to the payload molecule through a first and second pore simultaneously, the device comprising: (i) a first channel, a chamber and a second channel, (ii) a first pore, (iii) a second pore; (iv) a power supply configured to provide a first voltage at the first pore, and to provide a second voltage at the second pore, each voltage being independently adjustable, and (v) dual-amplifier electronics configured for independent voltage control and current measurement at each pore, wherein the first and second pores are configured so that the target polynucleotide is capable of simultaneously moving across both pores in a either direction, and in a controlled manner, d) loading the sample containing one or more target polynucleotides into the device; e) applying an initial first voltage and an initial second voltage so that at least a portion of the one or more target polynucleotides moves through the first pore and the second pore, wherein said first and second voltage induces translocation of the one or more target polynucleotides through the first and second pore separately for each of:
labeled 5mC regions on one or more polynucleotide sequences; labeled 5hmC regions on one or more polynucleotide sequences; f) generating a plurality of event signatures generated by translocation of one or more target polynucleotides through the first and second pore, g) identifying a quantity of first event signatures associated with labeled 5mC regions on one or more polynucleotide sequences and a quantity of second event signatures associated with labeled 5hMC regions on one or more polynucleotide sequences to distinguish between 5mC regions and 5hmC regions on one or more polynucleotide sequences.

In some embodiments, the method of the present disclosure comprises detecting (e.g. capturing) an ionic current of the one of more features of at least a portion of the target polynucleotide in a first direction, the first direction being from the chamber through the first pore and into the first fluidic channel. In some cases, the method comprises re-detecting (e.g. re-capturing) a second ionic current of the one of more features of at least a portion of the target polynucleotide in a second direction, the second direction being from the first fluidic channel through the first pore and into the chamber. In some cases, the method comprises co-detecting (e.g. co-capturing) a third ionic current and fourth ionic current (e.g. third ionic current when one or more features pass through the first pore, and a fourth ionic current when one or more features pass through the second pore, simultaneously) of one or more features of at least a portion of the target polynucleotide in a third direction, the third direction being from the first pore to the second pore (e.g. at least a portion of the target polynucleotide moving from the first pore through the chamber and into the second pore). In some cases, the method comprises re-detecting (e.g. re-capturing) a fourth ionic current of the one of more features of at least a portion of the target polynucleotide in a fourth direction, the fourth direction being from the second fluidic channel through the second pore and into the chamber.

In some cases, at least a portion of the target polynucleotide moves through the second pore in a time period ranging from 0.01 ms to 200 ms. In some cases, at least a portion of the target polynucleotide moves across the second pore in about 165 ms. In some embodiments, the first voltage is then adjusted to about 400 mV in order to pull the other end of the target polynucleotide in the opposite direction (e.g. a second direction, third direction, or fourth direction), reaching a tug-of-war state between the first and second pore. In some cases, the target polynucleotide comprises an increased force towards the second pore relative to the force of the first pore. In some cases, the target polynucleotide comprises an increased force towards the first pore relative to the force of the second pore. In some cases, the target polynucleotide comprises a tug-of-war state between the first pore and the second pore for a period of time ranging from 0.01 ms to 1000 ms. In some cases, the molecule exits the device during a time period ranging from 200 ms to 1000 ms.

In some embodiments, the target polynucleotide comprises a diffusion coefficient. In some cases, the diffusion coefficient of the target polynucleotide ranges from 0.01 mkm$^2$/s to 3 mkm$^2$/s. In some cases, the diffusion coefficient of the target polynucleotide is about 0.10, about 0.15, about 0.20, about 0.25, about 0.5, about 0.55. about 0.60, about 0.65, about 0.70, about 0.75, about 0.8, about 0.85, about 0.9, about 0.95, about 1.0, about 1.5, or about 2.0 mkm$^2$/s. In some cases, diffusion coefficient of the target polynucleotide is about 0.47 mkm$^2$/s. In some cases, the diffusion coefficient can be derived by A. Einstein formula, $D=\kappa \cdot T/6\pi\eta r$, where $\kappa$ is Boltzmann constant, T is thermodynamic temperature, $\eta$ is dynamic viscosity, and r is particle radius.

In some cases, the target polynucleotide is loaded onto the nanopore device. In some cases, the target polynucleotide is loaded in the chamber of the device. In some cases, the target polynucleotide is loaded in the first fluidic channel of the device. In some cases, the target polynucleotide is loaded in the second fluidic channel of the device. In some cases, loading the sample containing the target polynucleotide in the chamber provides for exchange of different reagents. In some cases, scanning and/or detecting the one or more features of the polynucleotide in the first direction (e.g. from the chamber through the first pore and into the first fluidic channel) and/or second direction (from the first fluidic channel through the first pore and into the chamber) screens out the short fragments of polynucleotide sequences. In some cases, movement of the target polynucleotide in the first direction for a longer duration provides for increased efficiency of detecting the one or more features of the target polynucleotide in the first direction.

In some embodiments, the tug-of-war state comprises the target molecule moving back and force between the first and second pore. In some cases, the target polynucleotide is co-captured in the first and second pore. In some cases, once cocapture occurs, control logic turns on constant competing voltages at the first and second pores, leading to a "tug-of-war". In some cases, the opposing forces are applied to regions of the target molecules threading through the pores. In some cases, the forces exert both conformational and speed control over the co-captured target polynucleotide. In some cases, the forces remove folds and reduce the translocation rate of the target polynucleotide. In some cases, when the first and second voltages are adjusted so that the electrophoretic force applied to the first and second pores comes into balance, the life time of the tug-of-war state is limited by diffusive sliding of the target polynucleotide between the first and second pore. In some cases, the ionic current of each of the first and second pores provides an independent sensor that synchronously measures a different region of the same polynucleotide, enabling sequential detection of one or more features. In some cases, the control logic is a controller. In some cases, the controller comprises a FPGA or an ASIC circuit to implement active feed-back control. In some cases, the control logic is configured to promote co-capture of a target polynucleotide in both the first and second pores. In some cases, the control logic is configured to engage competing voltage tug-of-war on the cocaptured target polynucleotide until the target polynucleotide exits the first and second pores. In some cases, the detection of the one or more features and exit of the target polynucleotide into the first pore only affects the first ionic current detected at the first pore. In some cases, the detection of the one or more features and exit of the target polynucleotide into the second pore only affects the second ionic current detected at the second pore.

Aspects of the present disclosure include A method for mapping one or more features of a target polynucleotide, the method comprising the steps of: a) providing a dual-pore, dual-amplifier device for controlling the movement of the target polynucleotide through a first and second pore simultaneously, the device comprising: (i) a first pore positioned between a chamber and a first fluidic channel, (ii) a second pore positioned between the chamber and a second fluidic channel, (iii) one or more electrodes positioned within the first and second fluidic channels, wherein the one or more electrodes are configured to provide a first voltage at the first pore, and to provide a second voltage at the second pore, each voltage being independently adjustable, and (iv) one or more sensors configured for independent voltage control and current measurement at each pore, wherein the first and second pores are configured so that the target polynucleotide is capable of moving across the first pore, across the second pore, and simultaneously moving across both pores in either direction, and in a controlled manner, b) loading the target polynucleotide into the chamber of the device; c) applying a first voltage at the first pore and a second voltage at the second pore so that at least a portion of the target polynucleotide moves from the chamber in a first direction to capture the target polynucleotide in the first pore and to allow the target polynucleotide to pass through the at least first pore into the first fluidic channel; d) scanning for one or more features of the target polynucleotide; e) detecting, in a first cycle, a first set of features when the target polynucleotide passes through the first pore; f) when the first set of features are detected in the first cycle in the first direction, adjusting the first voltage, the second voltage, or both, to the first and second pore to change the direction of the target polynucleotide so that at least a portion of the target polynucleotide moves in a second direction from the first fluidic channel to recapture the target polynucleotide in the first pore such that the target polynucleotide is maintained within the at least first pore, g) repeating step d); h) detecting, in the first cycle, the first set of features when at least a portion of the target polynucleotide is recaptured in the first pore; i) when the first set of features are recaptured in the first cycle in the second direction, adjusting the first voltage, the second voltage, or both, to the first and second pore to so that at least a portion of the target polynucleotide simultaneously moves in a third direction across the first pore and the second pore, the third direction being from the first pore to the second pore; j) repeating step d); k) detecting, in the first cycle, the first set of features when at least a portion of the target polynucleotide is in both pores; l) when the first set of features are detected in the third direction, adjusting the first voltage, the second voltage, or both, to the first and second pore to change the direction of the target polynucleotide so that at least a portion of the target polynucleotide simultaneously moves in a fourth direction across the second pore and the first pore, the fourth direction being from the second pore to the first pore, m) detecting, in the first cycle, the presence of a second set of features when at least a portion of the target polynucleotide is in both pores simultaneously in the fourth direction; and n) repeating steps c) through m) to detect a third and fourth set of features, in a second cycle.

Aspects of the present disclosure include methods A method for capturing a target polynucleotide in a nanopore device, the method comprising: a) providing a nanopore device for controlling the movement of the target polynucleotide through one or more pores, the device comprising: (i) at least a first pore positioned between a chamber and a first fluidic volume, the first pore fluidically connected to the chamber and to the first fluidic volume, the first fluidic volume being a geometrically constrained enclosure with an opening on a side opposite of the first pore, (ii) at least one electrode positioned within the first fluidic volume, wherein the one electrode is configured to provide a first voltage at the first pore, and (iii) an amplifier configured for voltage control and current measurement at the first pore; b) loading the target polynucleotide into the chamber of the device; and c) applying a first voltage across the first pore for moving the target polynucleotide from the chamber in a first direction to capture the target polynucleotide in the first pore and to allow the target polynucleotide to pass through the first pore into the first fluidic volume; d) detecting a first ionic current in the first pore when the target polynucleotide is passing through the first pore in the first direction; e) adjusting voltage to zero for a time period while the target polynucleotide is contained within the first fluidic volume; f) applying a second voltage to reverse the direction of the target polynucleotide positioned in the first fluidic volume, wherein said second voltage moves at least a portion of the target polynucleotide in a second direction from the first fluidic volume to recapture the portion of the target polynucleotide in the first pore such that the target polynucleotide is maintained within the first pore; and g) detecting a second ionic current in the first pore when the target polynucleotide is recaptured in the first pore.

Aspects of the present disclosure include devices and systems for mapping one or more features of a polynucleotide sequence of a target polynucleotide through a first and a second pore, the device comprising: (i) a first pore fluidically positioned between a chamber and a first fluidic channel; (ii) a second pore positioned between the chamber and a second fluidic channel, wherein the first pore and the second pore are configured such that the target polynucleotide is capable of moving across the first pore, across the second pore, and simultaneously moving across both pores, in either direction, and in a controlled manner; (iii) one or more electrodes configured to provide a first voltage at the first pore of the device, and provide a second voltage at the second pore of the device; (iv) one or more sensors configured for independent voltage control and current measurement at each pore, wherein the one or more sensors is capable of identifying: a first set of features, in a first cycle, from the target polynucleotide, during movement of at least a portion of the target polynucleotide from: the chamber through the first pore in a first direction, the first fluidic channel through the first pore in a second direction, the first pore through the second pore in a third direction; and the second pore through the first pore in a fourth direction; (v) a processor; and (vi) a non-transitory computer-readable medium comprising instructions that cause the processor to: a) apply the first voltage at the first pore and the second voltage at the second pore so that at least a portion of the target polynucleotide moves from the chamber in the first direction to capture the target polynucleotide in the first pore and to allow the target to pass through the at least first pore into the first fluidic channel; b) scan one or more features of the target polynucleotide; d) determine, from the one or more sensors, the presence of the one or more features of the target polynucleotide in the first pore in the first direction; d) count the first set of features in the first cycle in the first direction, and, responsive to that count, adjust one or both of the first and second voltages so that at least a portion of the target polynucleotide moves in the second direction from the first fluidic channel to recapture the portion of the target polynucleotide in the first pore such that the target polynucleotide is maintained within the first pore; e) repeat step b); f) determine, from the one or more sensors, the presence of the one or more features of the target polynucleotide in the first pore in the second direction; g) count the first set of features in the first cycle in the second direction, and, responsive to that count, adjust one or both of the first and second voltages so that at least a portion of the target polynucleotide simultaneously moves in the third direction across the first pore and the second pore; h) repeat step b); i) determine, from the one or more sensors, the simultaneous presence of the one or more features of the target polynucleotide in the first pore and the second pore in the third direction; j) count the first set of features in the first cycle in the third direction, and, responsive to that count, adjust one or both of the first and second voltages so that at least a portion of the target polynucleotide simultaneously moves in the fourth direction across the second pore and the first pore; k) repeat step b); l) determine, from the one or more sensors, the simultaneous presence of the one or more features of the target polynucleotide in the first pore and the second pore in the fourth direction; and m) repeat steps a) through l) to detect a third and fourth set of features, in a second cycle.

Aspects of the present disclosure include a method for determining the sequence of a target polynucleotide, the method comprising the steps of: a) providing a dual-pore, dual-amplifier device for controlling the movement of the target polynucleotide through a first and second pore simultaneously, the device comprising: (i) a first pore, (ii) a second pore; (iii) a power supply configured to provide a first voltage in the first pore, and to provide a second voltage in the second pore, each voltage being independently adjustable, and (v) dual-amplifier electronics configured for independent voltage control and current measurement at each pore, wherein the first and second pores are configured so that the target polynucleotide is capable of simultaneously moving across both pores in a first direction or a second direction, and in a controlled manner, b) loading the target polynucleotide into the device; c) setting an initial first voltage in the first pore and an initial second voltage in the second pore so that at least a portion of the target polynucleotide moves through the first pore and the second pore in the first direction, wherein the first direction being from the first pore to the second pore; d) scanning for one or more primers hybridized to the target polynucleotide; e) detecting, in a first cycle, a first set of primers when the target polynucleotide is in both pores in the first direction; f) re-scanning for the one or more primers hybridized to the target polynucleotide; g) when the first set of primers are detected in the first cycle in the first direction, adjusting the first voltage, the second voltage, or both, to the first and second pore to change the direction of the target polynucleotide so that at least a portion of the target polynucleotide moves from the second pore to the first pore in the second direction, h) detecting, in the first cycle, the presence of the second set of primers when the target polynucleotide is in both pores simultaneously in the second direction; i) identifying each nucleotide of the polynucleotide that passes through one of the pores, by measuring an ionic current across the pore when the nucleotide passes that pore; and j) repeating steps c) through i) to detect a third and fourth set of primers, in a second cycle.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

Examples of Non-Limiting Aspects of the Present Disclosure

Aspects, including embodiments, of the present subject matter described above may be beneficial alone or in combination, with one or more other aspects or embodiments. Without limiting the foregoing description, certain non-limiting aspects of the disclosure numbered 1-171 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Nanopore Flossing DNA in a Dual Nanopore Device

Here an active control technique was presented termed "flossing" that uses a dual nanopore device to trap a protein-tagged DNA molecule and perform up to 100's of back-and-forth electrical scans of the molecule in a few seconds. The protein motifs bound to 48 kb) λDNA were used as detectable features for active triggering of the bidirectional control. Molecular noise was suppressed by averaging the multi-scan data to produce averaged inter-tag distance estimates that were comparable to their known values. Since nanopore feature-mapping applications required DNA linearization when passing through the pore, a key advantage of flossing was that trans-pore linearization was increased to >98% by the second scan, compared to 35% for single nanopore passage of the same set of molecules. In concert with barcoding methods, the dual-pore flossing technique enabled genome mapping and structural variation applications, or mapping loci of epigenetic relevance.

It was shown that highly accurate spatial information that is correlative with motif binding can be obtained from a single labeled carrier dsDNA strand via repeated back-and-forth scanning of the molecule trapped in a nanopore device. Using a new active control technique termed "flossing," the present inventors were able to perform up to 100's of scans of a given trapped molecule within a few seconds. Flossing was showcased here using a model system consisting of a 48.5 kbp double-stranded λ-DNA with a set of chemically incorporated sequence-specific protein tags. The approach of this study complements existing carrier-strand DNA nanopore technology by enhancing the quality of information that was extracted from a single trapped molecule. By taking a large number of statistically equivalent scans, stochastic fluctuations were reduced through scan averaging, and show mean tag spacing estimates that were comparable to known inter-tag distances, even while tolerating missed tag(s) within a subset of scans.

The device of the present disclosure employed a dual-pore architecture. By having the dual pores sufficiently close, DNA was captured simultaneously by both pores and exist in a 'tug-of-war' state where competing electrophoretic voltage forces were applied at the pores. During tug-of-war, the molecule's orientation and identity were maintained, the molecule speed was regulated to facilitate tag sensing, and the likelihood of the molecule finding a linearized conformation through the pore was increased to 70% compared to 30% with single pore data. An advantage of flossing was that linearization through the pore was further increased to >98% by the second scan, which in turn increased the throughput of nanopore feature-mapping applications.

Another distinct feature of the presented approach was that the active controller cyclically modulated the voltage at one pore by a real-time feedback on the sensing current of the other pore. Specifically, during control, the cyclical application of unbalanced competing voltage forces were used to drive the molecule's motion in one direction and then, after real-time detection of a set number of tags, in the reverse direction, thereby embodying the concept of DNA "flossing." Coupling the DNA to a stage produced both speed control and mineable data generation during the molecule's motion through a solid-state pore, but at the price of complex instrumentation, higher sensing noise and lower throughput. In the presented flossing control method, an interrogated DNA molecule was ejected from the pores and a new DNA captured with the same throughput and ease of any single-nanopore based assay, with no tethering of the molecule required.

Results and Discussion
The DNA Flossing Concept

Figure 9:
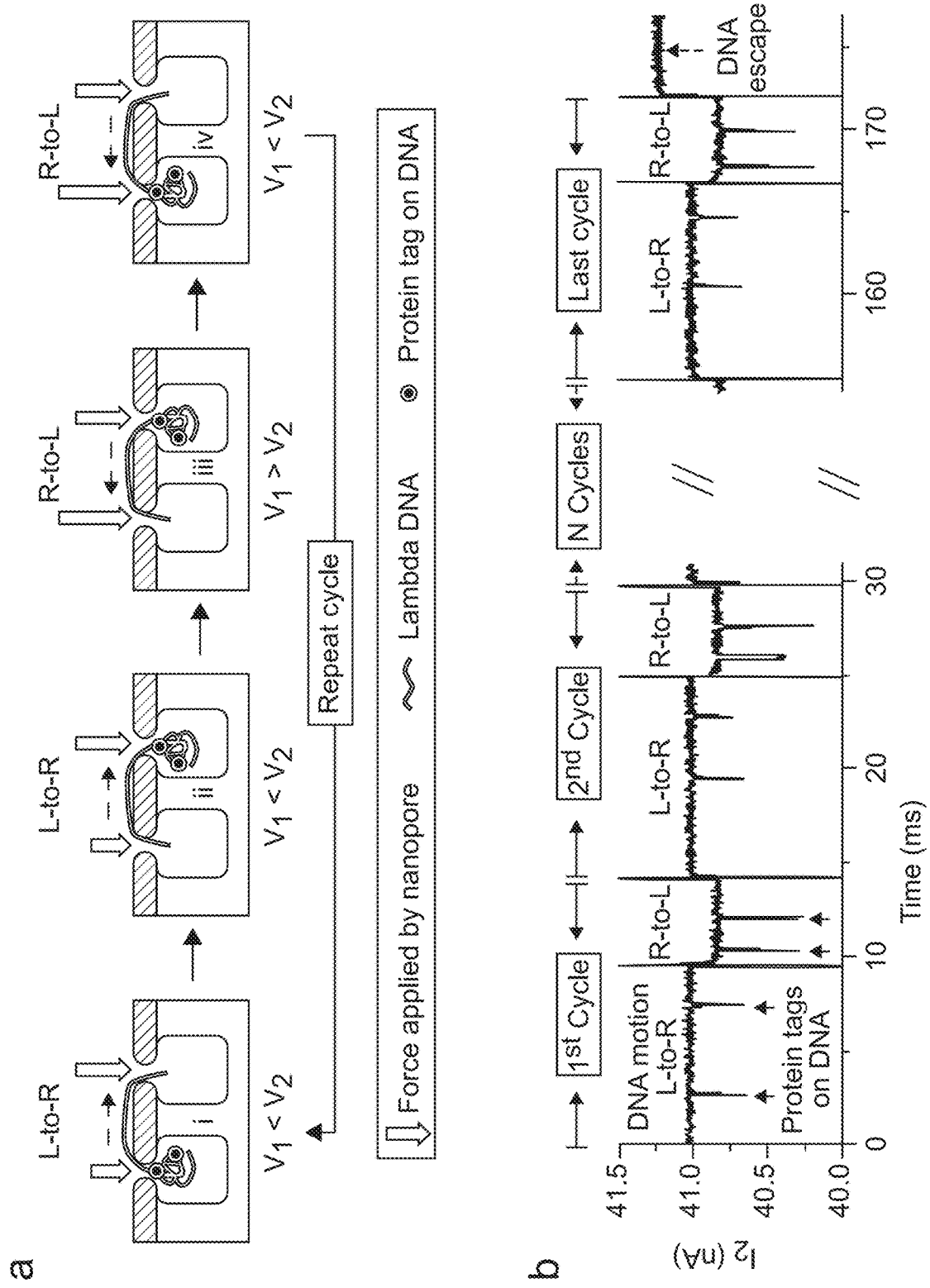
FIG. 9 depicts flossing DNA with competing voltage forces in a dual pore device. (a) After DNA co-capture, the DNA molecule will be threaded from left-to-right (L-to-R) using a voltage $V_1<V_2$, with $V_1$ and $V_2$ the voltages across pore 1 (left) and pore 2 (right), respectively. A single transit of DNA motion during this fixed polarity period is called a "scan." After automated detection of a predefined number of tags, the direction of DNA motion is reversed with a voltage $V_1>V_2$ triggered to move the molecule from right-to-left (R-to-L), giving rise to a second scan. The process is repeated in cyclical fashion until the molecule randomly exits the co-capture state. (b) A recorded multi-scan current trace 12 from pore 2, using logic for which the predefined tag detection number is 2, after which the controller triggers the change in direction. The signal from 30-150 ms is truncated for visualization. The example showed raw data from a multi-scanning event showing two detected mono-streptavidin (MS) tags on each scan moving from pore 1→2 and pore 2→1, until the DNA escaped after 50+ scans.

FIG. 9 introduced the general flossing concept, showing pictorially and with actual recorded data the cyclical bidirectional scans of a co-captured molecule in a dual nanopore device. The dual nanopore device was fabricated using known methods, with voltages $V_1$ and $V_2$ that were independently applied at pore 1 and 2, respectively. Two currents ($I_1$ and $I_2$) were also independently measured at the pores. The tagged reagent featured monovalent streptavidin (MS) proteins bound along the DNA.

FIG. 9a illustrated each step in a multi-scan cycle. Since the motion control was bidirectional, a single transit was defined with fixed direction as a "scan" and two sequential scans of reversed polarity as a "cycle." By convention, the left pore was defined as pore 1 and the right pore as pore 2. During the multi-scan control logic sequence, $V_2$ across pore 2 was kept constant while $V_1$ was modulated in step-wise fashion. The signal $I_2$ was monitored in real-time for tag-related events as a logic trigger for $V_1$ changes, as described next.

Figure 18:
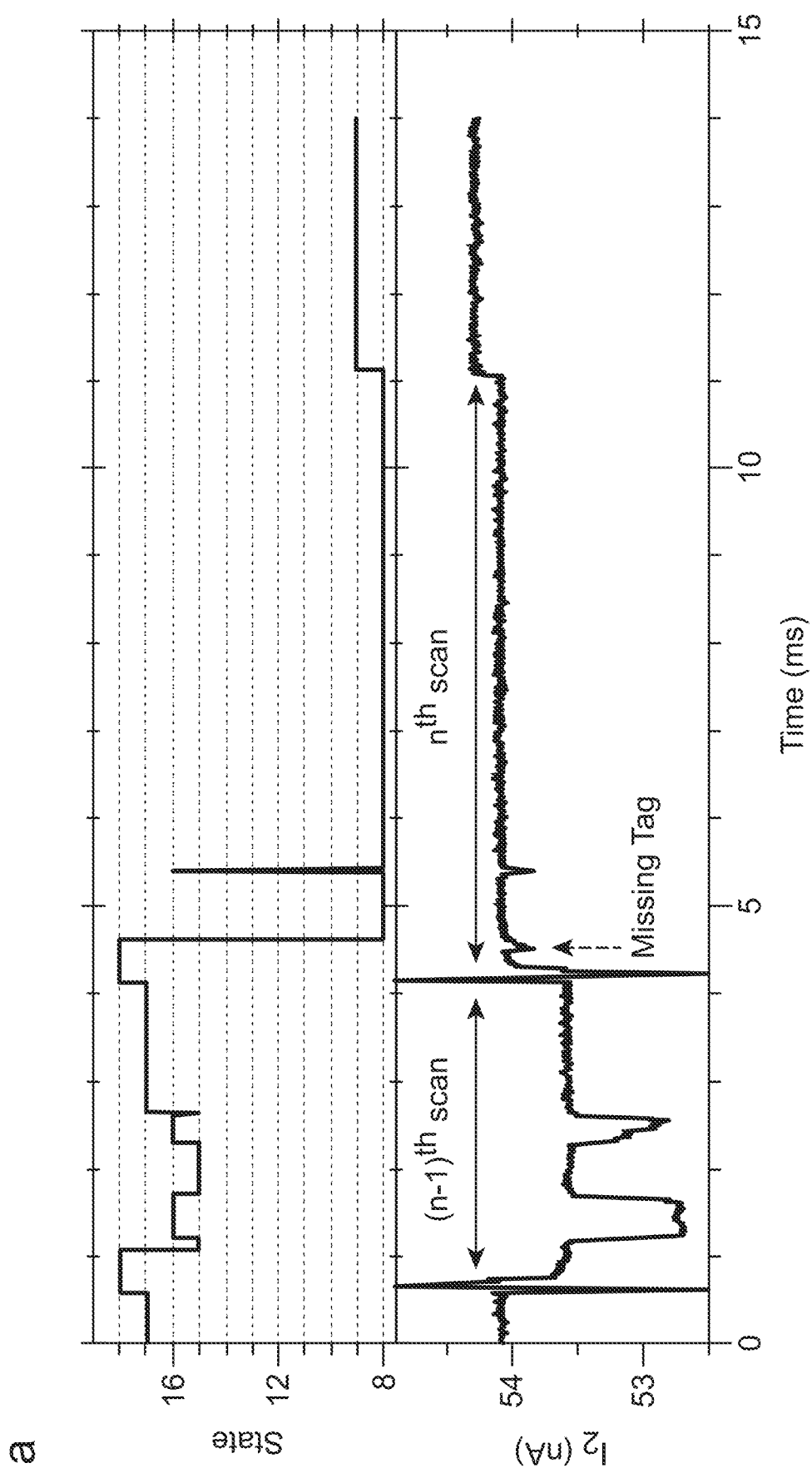
FIG. 18 depicts Four major cases that the FPGA failed to catch more scans. The plots are the signal of State from FPGA and 12 in the last cycle. The definition of the state is in FIG. 17b. (a) The tag shows up in the hold (18) state of the n th scan. The line with arrows mark the (n−1) th and n th scan. (b) A false positive spike in the (n−1) th scan. (c) A false negative spike in then th scan. (d) The molecule left pore 2 in the delay (17) state of the n th scan.
Figure 18:
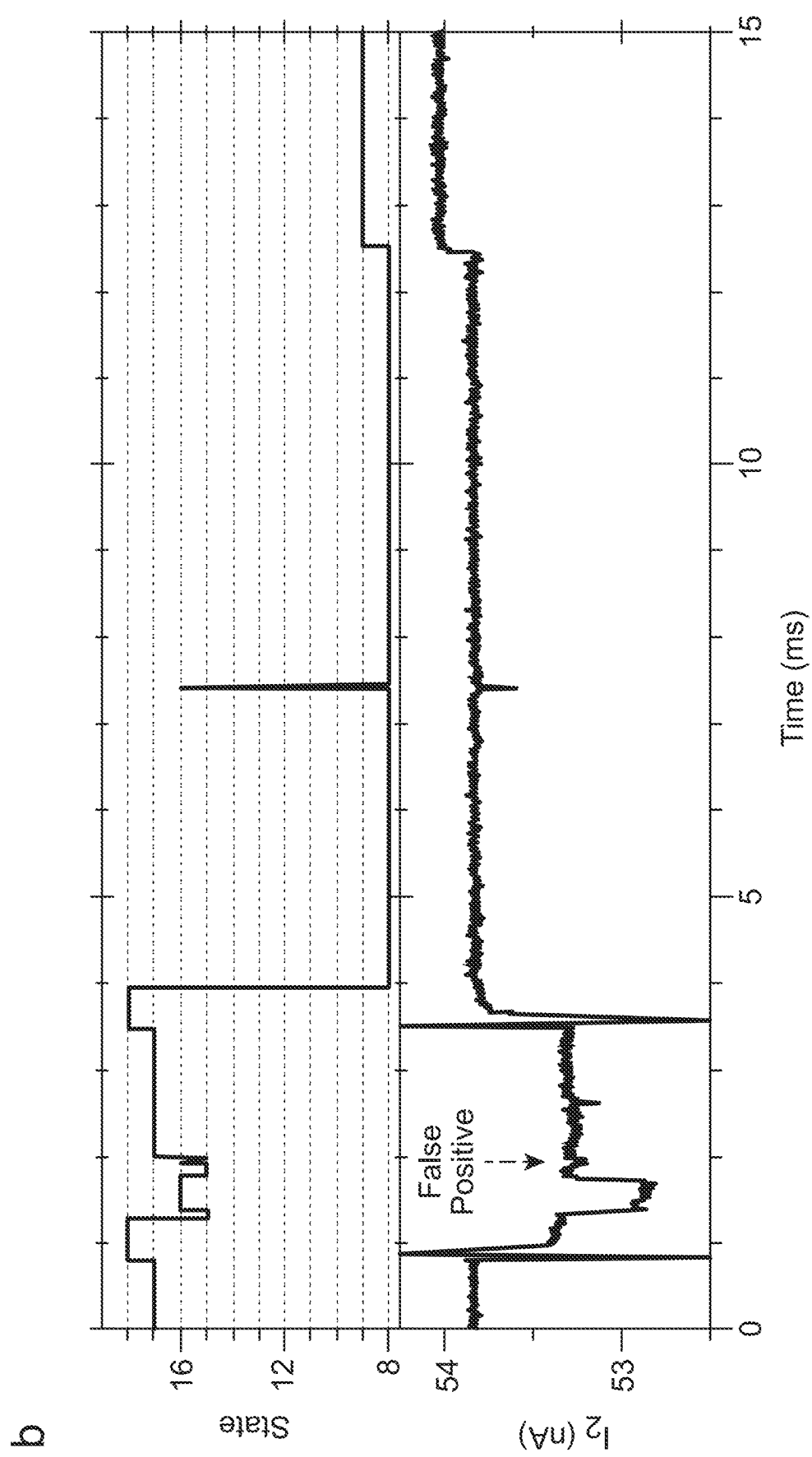
Figure 18:
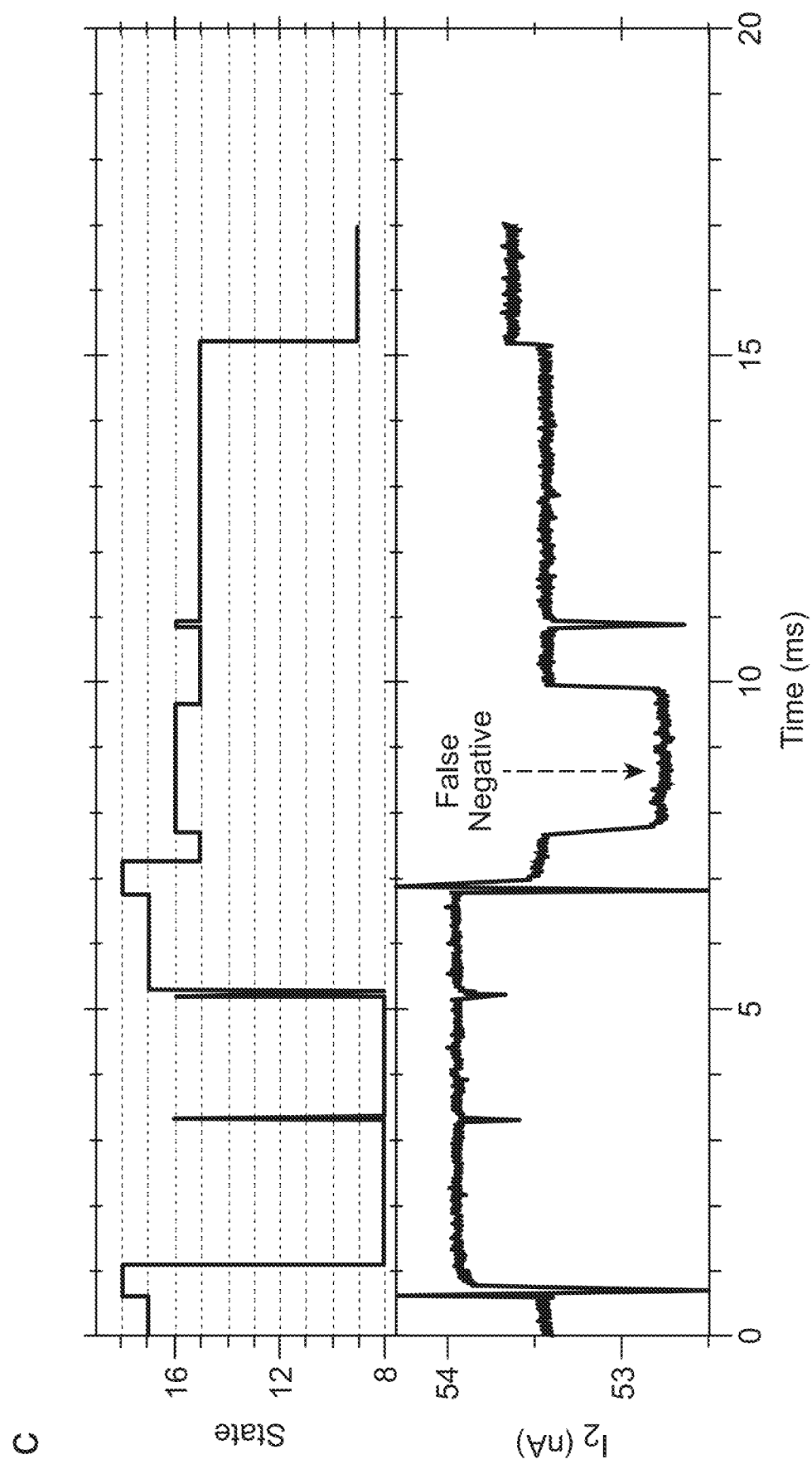
Figure 18:
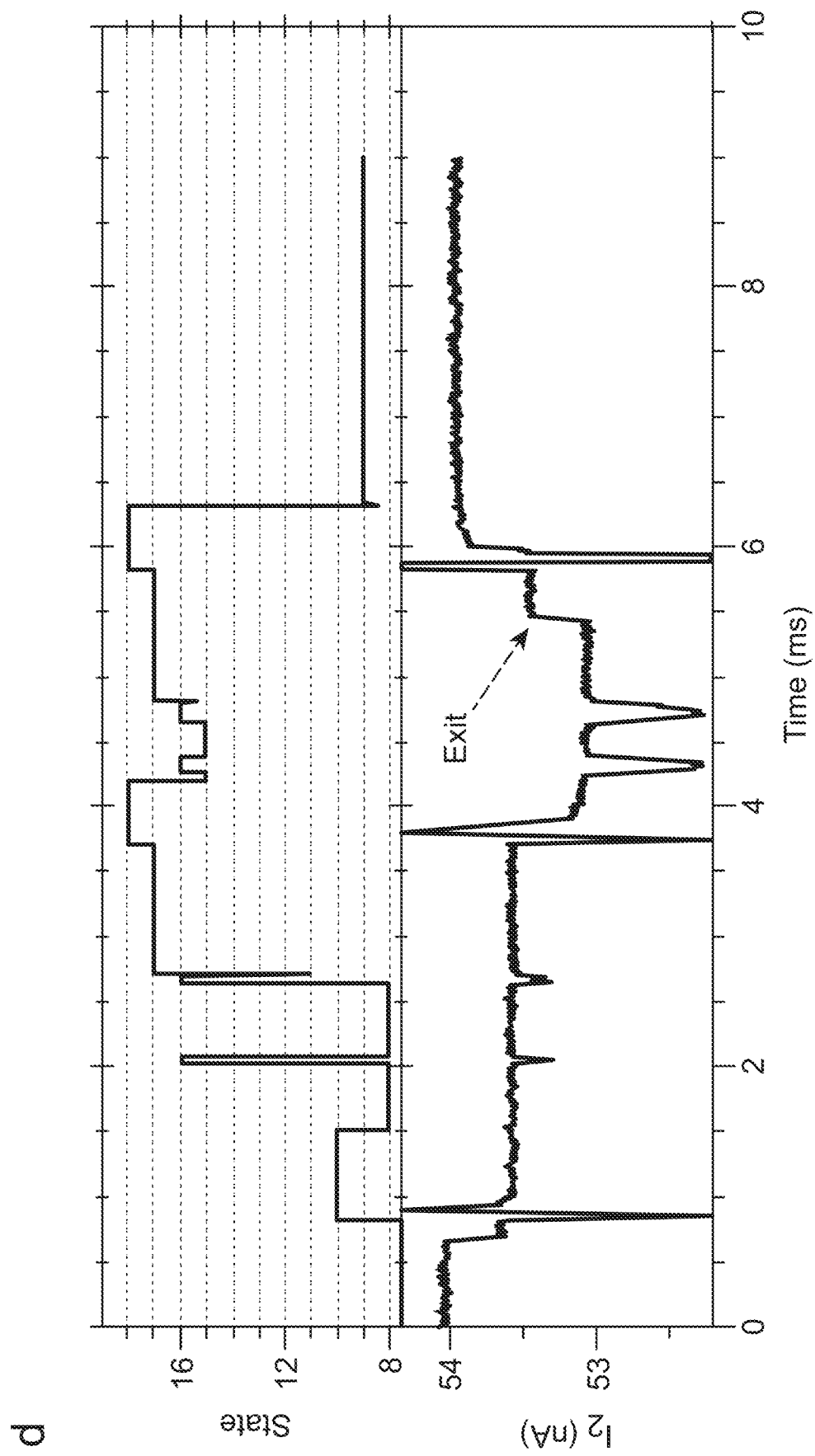
Figure 19:
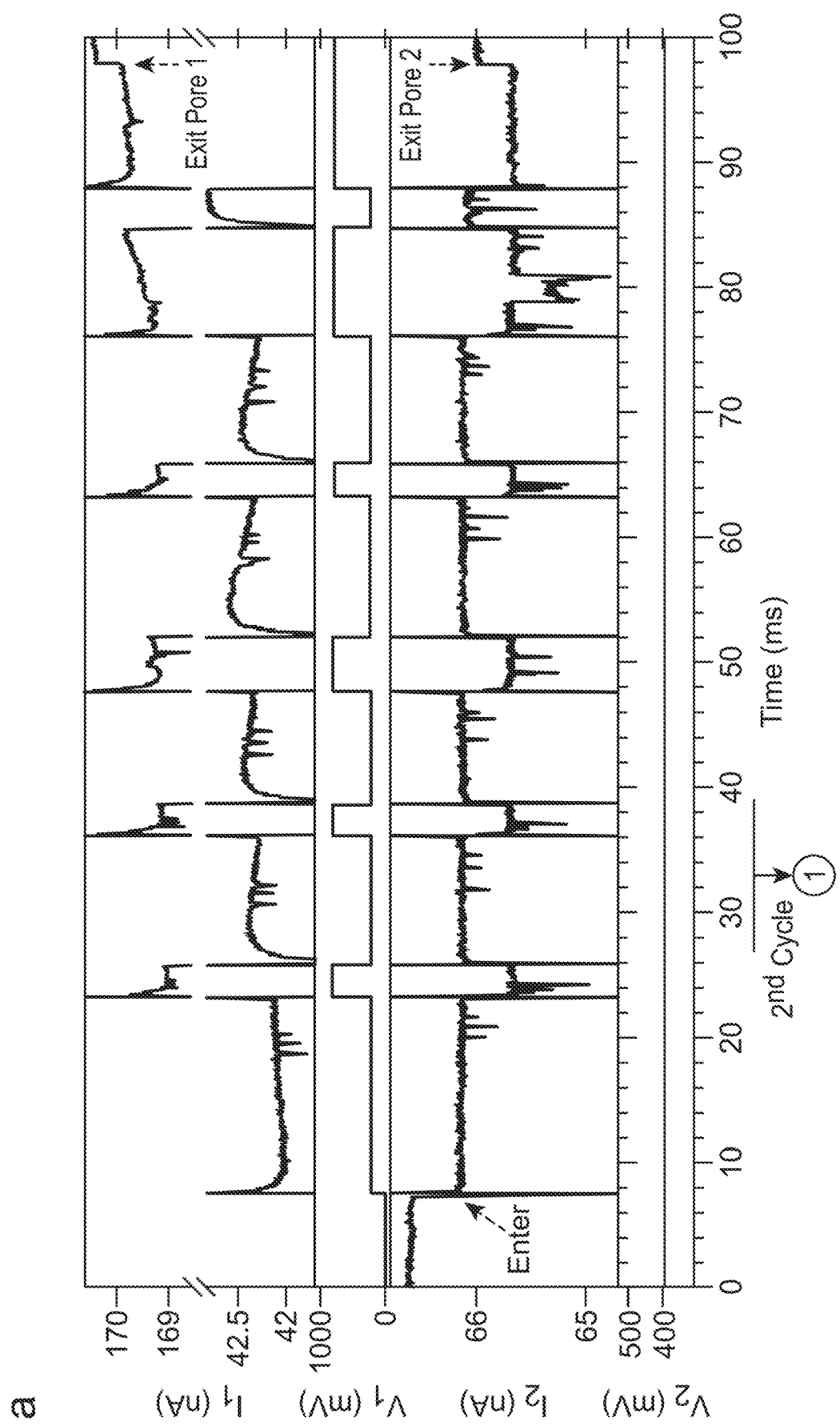
FIG. 19 depicts Multi-scan experiment with three-tags trigger. (a) Full signal trace of I1, $V_1$, I2, and $V_2$. $V_2$ was set to $V_2$=400 mV during the event $V_1$=200 mV for L-to-R scan and $V_1$=800 mV for R-to-L scan. $V_1$ was set (b) Zoom-in plot of the 2 nd cycle. (c) Distribution of the scans count per event with theoretical fitting.
Figure 19:
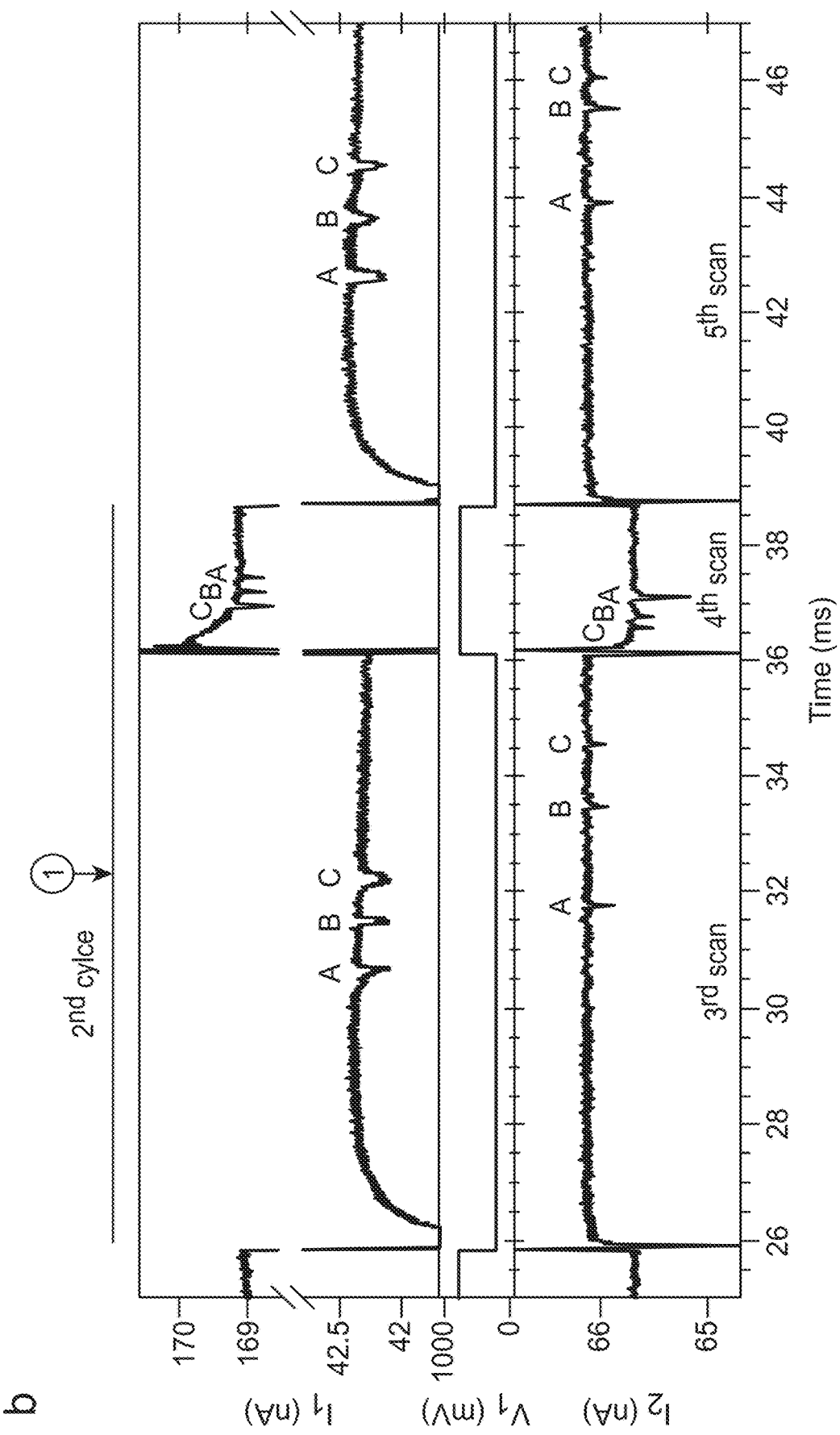
Figure 19:
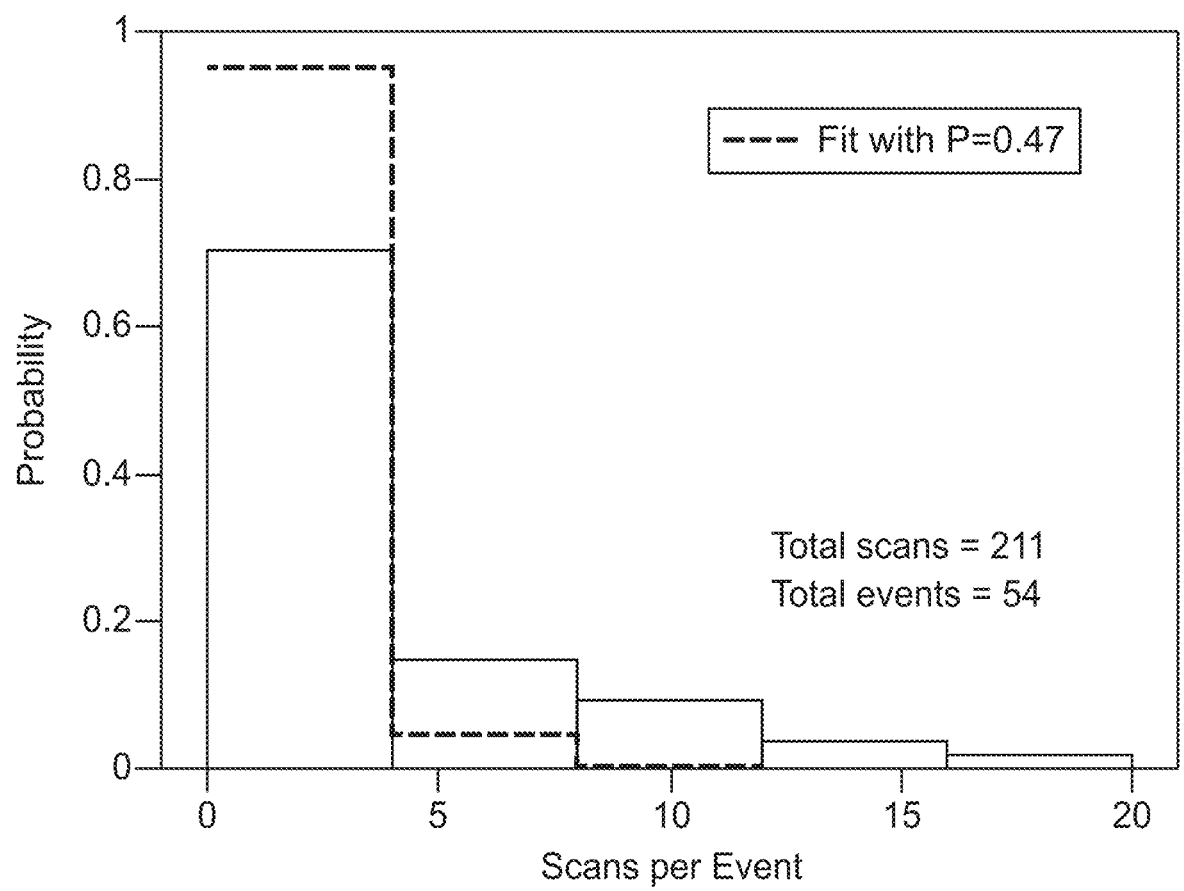

The flossing control logic begins by initially co-capturing a tagged DNA in both pores to reach the tug-of-war state. Once co-capture occurred, a lower voltage was applied across pore 1 than pore 2 ($V_1<V_2$) to direct the molecule motion towards pore 2 (left-to-right, or "L-to-R"). While monitoring I2, the control logic readjusted the voltage at pore 1 so that $V_1>V_2$ after a set number N of tags were detected translocating through pore 2. The readjustment directed the molecule motion back towards pore 1 (R-to-L). After detecting the same set number N of tags translocating through pore 2, the logic reset $V_1<V_2$ to initiate another L-to-R scan, and thus a new cycle begins. FIG. 9b showed a recorded example of the first two cycles and the final cycle of the 12 signal for which the tag number setting was N=2. In this example, the multi-scan cycle begins with the molecule moving L-to-R for the first 9 ms and continued until 172 ms when the DNA escaped just after a $V_1$ modulation (escape modes are discussed below and in detail in the SI). Details on the set of dual-pore chips and voltage settings used in this study are provided in Tables S1-S2 (FIGS. 18-19). Having described the general flossing concept, the method was next presented in greater detail and results obtained using the method.

Initializing Tug-of-War and Identifying Scanning Voltages

Figure 16:
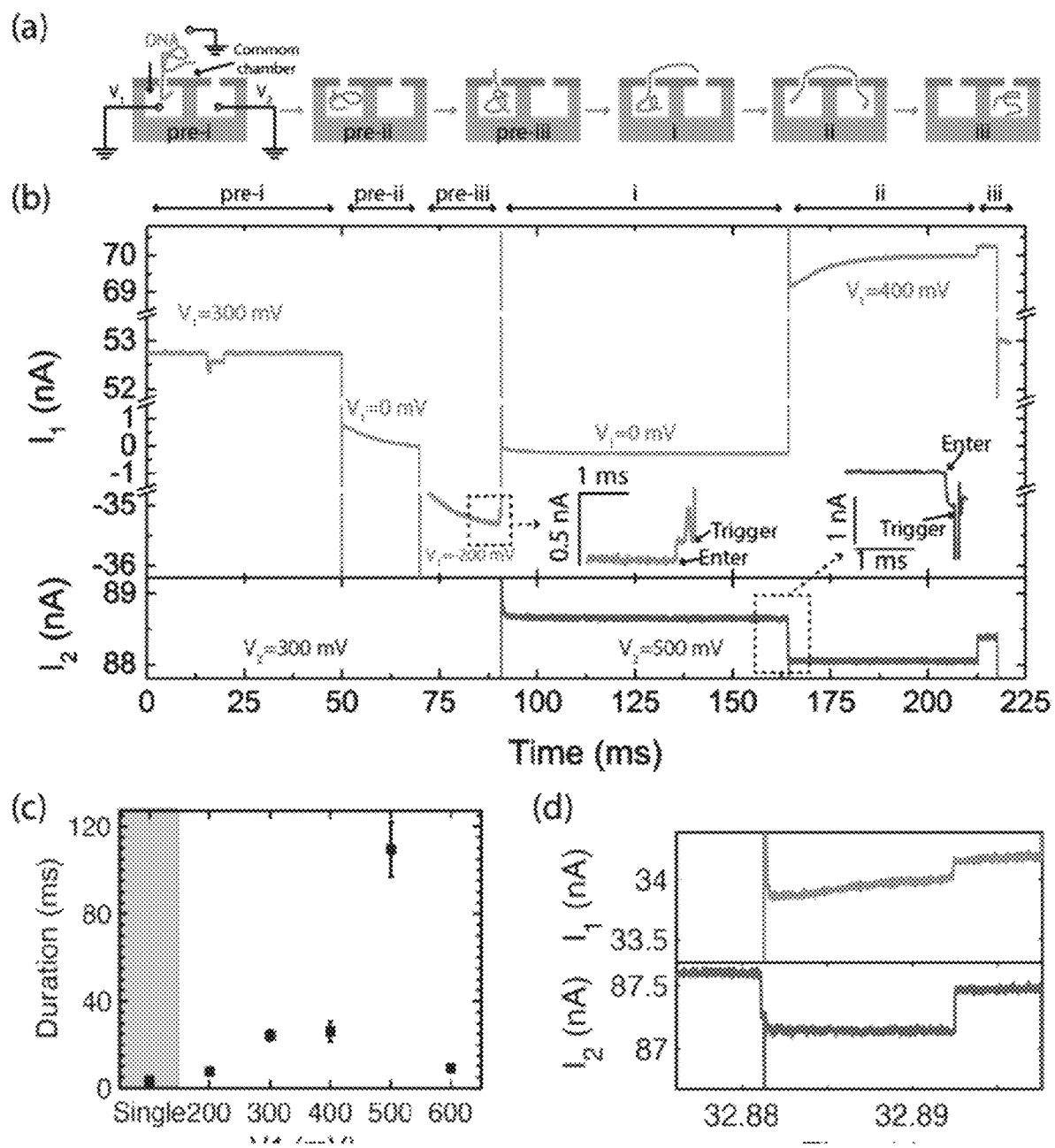
FIG. 16 depicts full process of one tug-of-war event. (a) Illustration of each step. (b) Current trace from both pore 1 and pore 2. $I_1$ is in red while $I_2$ is in blue. The y-axis of pore 1 was broken three times to fit the different value in one figure. The insect shows the zoom-in when trigger happens. (c) The mean duration at different $V_1$ with single pore events duration. (d) Current trace pair of one tug-of-war event with λDNA at $V_1$=200 mV.

The control logic that automated the flossing process shown in FIG. 9 is described here in detail. The flossing method first used active control to automate initializing co-capture and tug-of-war on a single molecule. The control logic was run in real-time (MHz clock rate) on a Field Programmable Gate Array (FPGA). The designed tug-of-war control process was modified to permit loading reagent in the common fluidic chamber above the two nanopores and to screen out short-fragments (SI Section 2, FIG. 16). Once co-capture was achieved the competing voltage forces at $V_1$ and $V_2$ lead to a tug-of-war and reduced the DNA speed during sensing. The mean durations of all co-captured events were computed at each of a set of different $V_1$ values while keeping $V_2$ constant, showing a bell curve with the peak revealing the force-balancing voltages that maximize co-capture duration. FIG. 16c showed an example device with peak mean duration of 110 ms with $V_1$ and $V_2$ both set to 500 mV. This data was generated with bare DNA that has no tags.

While capturing a molecule in dual pore tug-of-war introduced speed and conformational control, bare double-stranded DNA offered no detectable features with which to monitor the molecule's motion. To enable in-situ feature monitoring, MS-tagged DNA was developed as a model reagent, with up to 7 sites tagged on the DNA (SI Section 3, FIG. 21). The tag features were used to make inferences on the speed and direction of each scan, which enabled identifying the scanning voltages as described next.

The scanning voltages were found after the force-balancing voltages that maximize co-capture duration have been identified for a given chip. Specifically, the scanning voltage values for $V_1$ were chosen above and below it's force balancing value in order to promote unperturbed DNA motion toward pore 1 and pore 2, respectively, while keeping $V_2$ at it's force balancing value. The $V_1$ scanning values were chosen heuristically, using the following guidance. A working scan speed should enable robust sensing of tag blockades at the recording bandwidth (i.e., not too fast), while ensuring sufficiently high Peclet numbers so that translocation time distributions were well-defined (i.e., not too slow). That is, broad translocation time distributions increase the probability of fluctuations, which can undermine the intertag time-to-distance mapping objectives described in a later section. In practice, achieving a not-too-fast and not-too-slow scan speed was achievable for a broad range of scanning $V_1$ voltages. For the data in this paper, that range was as low as 150 and as high as 500 mV away from the force-balancing voltage.

Representative Flossing Event with Protein-Tagged DNA

Figure 10:
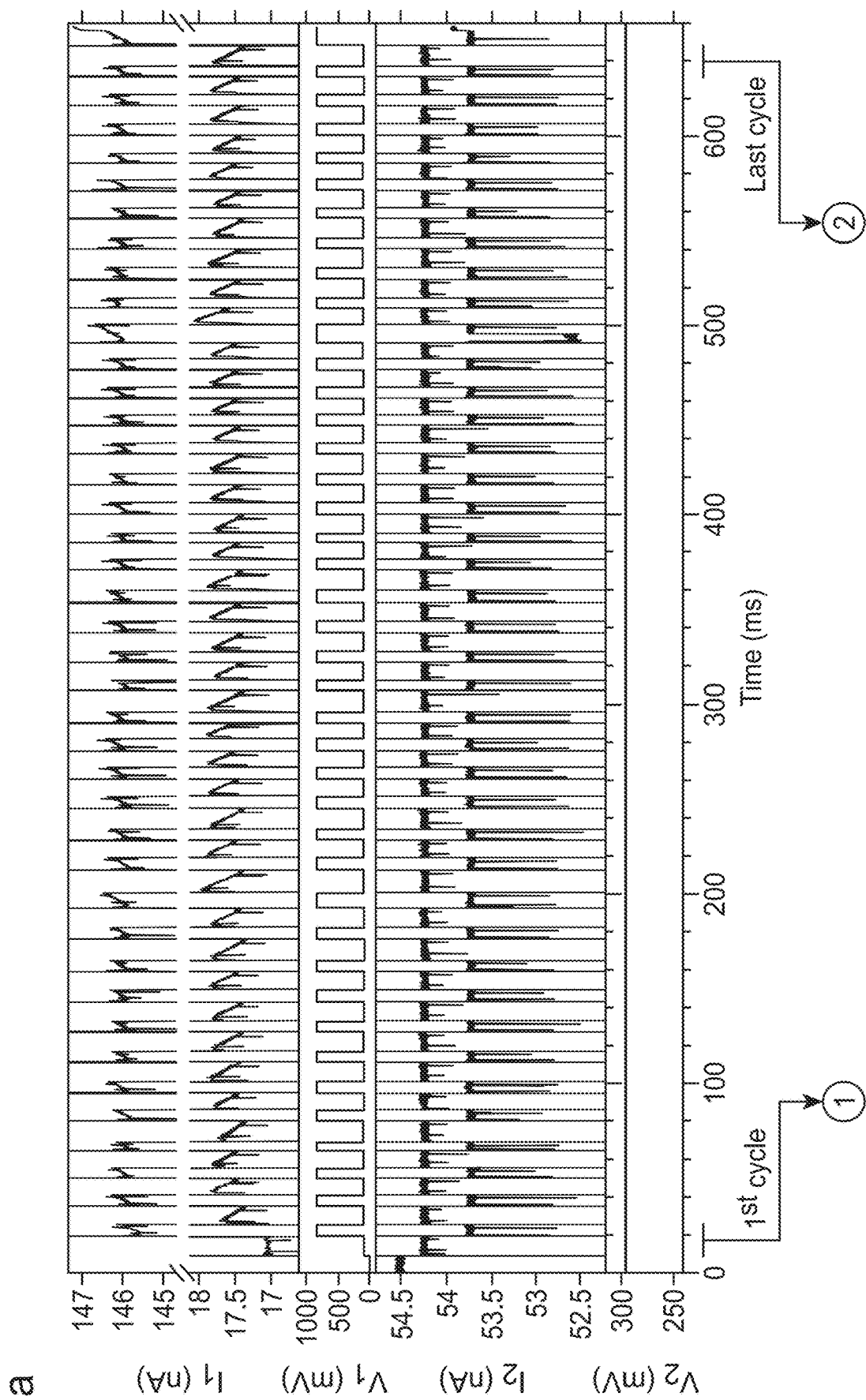
FIG. 10 showed representative dual current signals and scan count statistics generated during a flossing experiment with MS-tagged DNA. a Full signal traces for $I_1$, $V_1$, $I_2$ and $V_2$ are shown for a representative multi-scan flossing event. The vertical-axis break in the $I_1$ signal permits vertical-scale zooming on the low and high ranges during the lower and higher $V_1$ values. B Zoom in of the 1st cycle where two-tag logic showed resolvable tags A and B in both signals. C Zoom-in of the 41st and last cycle, showing the end of co-capture due to an undetected tag. d The total flossing time (mean±standard deviation) and probability distribution versus scan counts across all co-captured events for the device used (bin width=4). The red line on the probability data is the fitted model equation (1), with p=0.89 the probability of correctly detecting two tags in each scan. The chip used had a pore-to-pore distance of 0.61 μm, 27 nm pore 1 diameter, and 25 nm pore 2 diameter.
Figure 10:
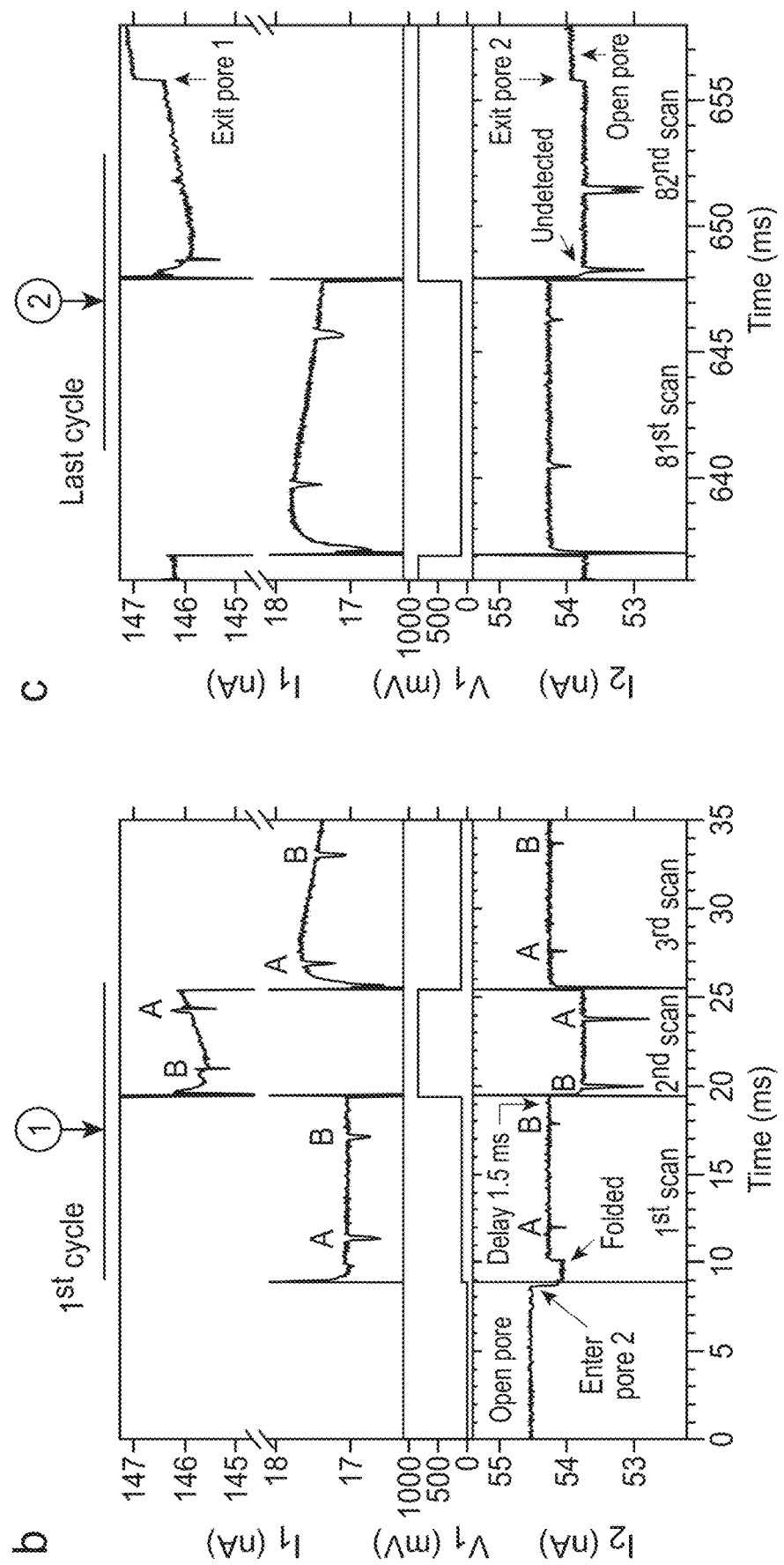
Figure 10:
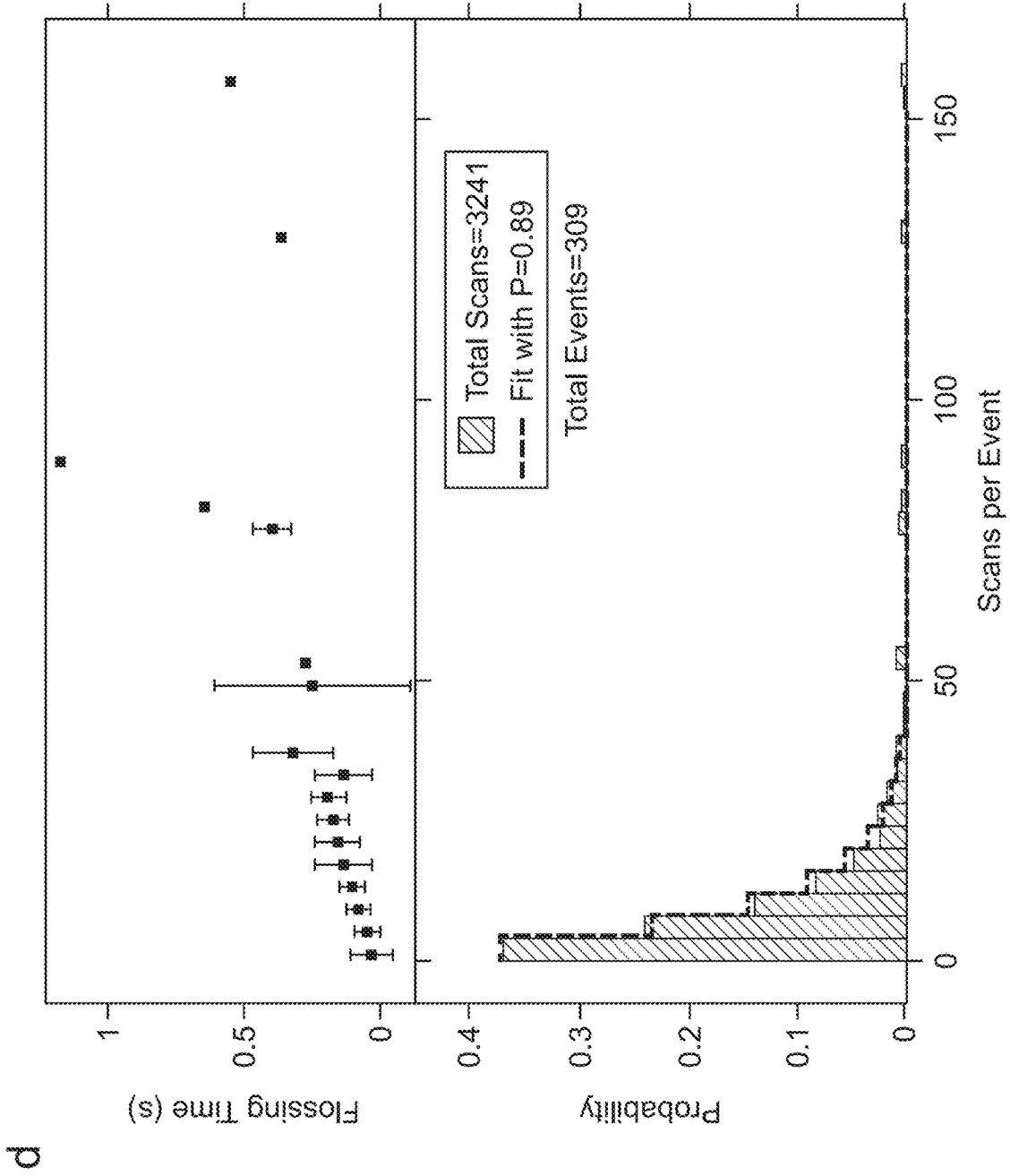

Once the scanning voltage values were identified, the full flossing multi-scan logic can be applied. The full details of the FPGA-implemented logic were provided in supplementary materials (SI Section 4, FIG. 17). The output of the logic was conveyed here by representative flossing data [10]. FIG. 10a showed the full signal trace of $I_1$, $V_1$, $I_2$ and $V_2$ from a typical flossing event. tV2 was kept at $V_2$=300 mV unchanged within the event. $V_1$ was set at $V_1$=100 mV for L-to-R movement and $V_1$=850 mV for R-to-L movement. Note that the $I_2$ baseline varies when $V_1$ was adjusted even though $V_2$ was constant. This effect was caused by cross talk between pore 1 and pore 2 that was previously characterized. The detectability of tags relative to the DNA baseline in $I_2$ was still robust, despite the baseline change. As detailed in the previous section, sufficiently large voltage differentials were chosen between $V_1$ and $V_2$ to promote controlled motion in each direction during sensing.

Figure 2:
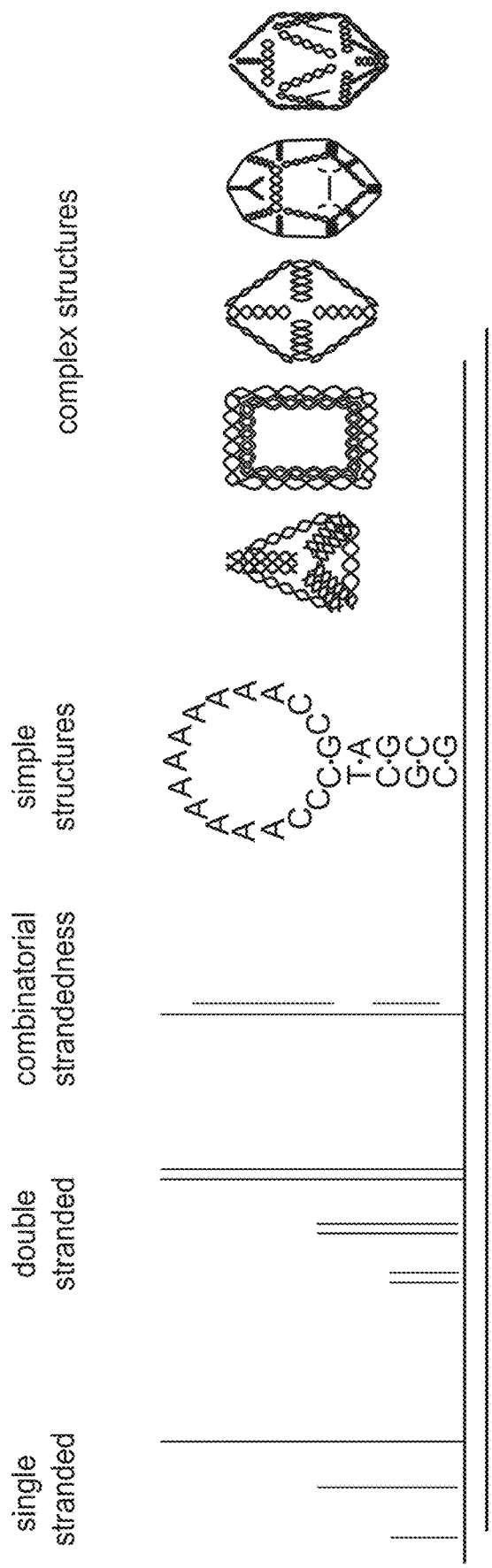
FIG. 2 depicts modulation of a nanopore impedance by variation in the size and shape of DNA attachments.

FIG. 10*b,c* give a magnified view of the signal for the first cycle that comprises the 1st and 2nd scans, and the last cycle comprising the 81st and 82nd scans. By convention, since the multi-scan logic starts in the L-to-R direction, the odd scans correspond to L-to-R movement and the even scans R-to-L movement. The event in FIG. 10*a* includes 41 cycles and 82 scans total, all in less than 0.66 sec. As depicted in FIG. 1, the FPGA logic was designed to switch $V_1$ once two tags were detected within $I_2$. The FPGA detects a tag when $I_2$ falls at least 70 pA below the untagged DNA baseline for at least 0.012 ms. The data in FIG. 2 showed two tags, A and B, in both $I_1$ and $I_2$ when the molecule moved L-to-R from 9 to 19 ms. Following a 1.5 ms-delay after tag B was detected, the FPGA set $V_1$=850 mV, driving the molecule to move R-to-L from 19 to 25 ms. The same tags, B and A, were detected in both $I_1$ and $I_2$ in reverse order. The same logic continued until the FPGA failed to detect tag B in the last cycle (FIG. 10*c*), which was caused by the tag appearing too close to the voltage change for the FPGA to detect it.

The total flossing time and distribution of the number of scans per event were shown in FIG. 10*d* for a total of 309 flossing events in an experiment, including the 82 scan event in FIG. 10*a*. Total flossing time increases with more scans, while all events terminated in less than a few seconds, even for the largest scan count of 157 for this data. While individual scans last 5-10 ms (FIGS. 9*b* and 10*b-c*), the total time data showed a significant increase (up to 100× more) in time spent interrogating each molecule by using the flossing method.

From the probability plot in FIG. 10*d*, 37% of the events had less than 5 scans, and events with higher scan count were less likely. The probability P (n) of seeing a specific total number of scans n was examined, where the probability of any intermediate scan has correct detection probability p and missed detection probability (1−p). An event with n total scans indicates the system successfully catches the initial (n−1) scans but fails to catch the nth scan. Thus its probability P(n) is:

$$P(n)=p^{n-1}(1-p). \quad (1)$$

Fitting the data to equation (1) results in p=0.89 for this specific data set (FIG. 10*d*). To determine why the molecule exits co-capture, the last cycles were studied and found four common cases: missing a tag in the nth scan (FIG. 18*a*); a false positive spike detected in the (n−1)st scan (FIG. 18*b*); a false negative spike in the nth scan (FIG. 18*c*); and the molecule exits the pore during the FPGA delay state (FIG. 18*d*). A discussion on how to increase the total number of scans per event can be found in SI section 5. Naturally, changing the voltage settings will affect event duration between tags, which in turn will affect tag detection probabilities.

A dependence of tag amplitude on scan direction was observed in FIG. 10*a-c*, with MS tags showing relatively shallower and faster spikes when passing through the pore with the higher voltage of the two. Seeing a faster and shallower tag event at higher voltage was consistent with single pore results, and was in part an artifact of the low-pass filter (10 kHz bandwidth) preventing the tag events from hitting full depth (i.e., the faster the event, the shallower).

A multi-scan experiment using a three tag triggering setting was also performed (FIG. 19). It was harder to get a higher scan count using three tag triggering than with two. In part, this arises because fewer molecules (<20%) show three or more tags. Also, even when the system co-captures one molecule with three tags in both pores, the probability of correct detection of all three tags was lower (FIG. 19*c*), and failing to detect any one of the tags moves the molecule to a new region, thereby lowering the scan count for the originally scanned three tag region. To generate more data with higher scan counts, therefore the experiments were focused on two-tag triggering in this initial presentation.

Flossing Increases the Fraction of DNA with Mappable Data

Nanopore feature-mapping applications require DNA linearization when passing through the sensing pore. As such, the fraction of DNA was explored that can be linearized by the flossing technique, where linearization refers to the removal of DNA folds that were initially in the pore when co-capture was initialized. By example, the molecule in FIG. 10*a-c* was partially folded at around 10 ms in the 1st cycle (FIG. 10*b*), which was eliminated in the 2nd cycle and thereafter, demonstrating the tendency of tug-of-war control to induce and maintain DNA linearization. The probability of complete linearization over the scanning cycle through pore 2 was examined as a function of scan number to see if the trend in FIG. 10*a-c* was representative of the population. Indeed, FIG. 11 showed that the probability of linearization was increased to 98% by the second scan. In the data, a folded event was identified if the current blockage was larger than 1.5 times the unfolded blockage amount, and lasts more than 180 µs. FIG. 11*a,b* show representative single pore and multi-scan events with observable folding examples.

A qualitative mechanism of the progression of unfolding during flossing in FIG. 11*c* was proposed. Going L-to-R, motion and the field force at pore 2 were aligned, which promotes folds eventually moving through pore 2 and into channel 2. Subsequently, R-to-L motion pulls only the region of DNA that was under tension via Tug-of-War back through pore 2, despite the counter field force at pore 2, while folds not under Tug-of-War tension experience only the field force and thus remain in channel 2 and away from pore 2. FIG. 11*d* showed the ratio of unfolded events for the progression of translocation types that each of the 309 events went through. Thus the statistics in each column were from exactly the same group of molecules, and were the same data as FIG. 10. The 35% unfolded probability through the initial single pore capture (pore 1 in the device) was consistent with other single pore studies. Following co-capture, 66% of 1st scans were unfolded, which was consistent with tug-of-war data without flossing [28]. By the 2nd scan, only 6 molecules out of 309 (2%) remain folded, and only 5 remain folded by their last scan. Thus the flossing process effectively linearizes the DNA molecules through the nanopore sensors at high probability.

Tag Data Analysis: A Single Scan View

The multi-scan data set (constituting L-to-R and R-to-L scans for each pore) contains rich information regarding the underlying tag binding profile and translocation physics. Each individual scan taken from the two pores provides a snapshot of the translocation process for the portion of DNA being scanned. There were two ways to assess the translocation velocity from the tag. The first approach was to quantify the speed of a tag as moves through a single-pore ('dwell time estimation'), which was based on dividing the tag blockade duration (width-at-half-maximum) into the membrane thickness (35 nm). The second approach was unique to dual nanopore technology, and was to assess tag speed as it moves from the first pore (Entry) to the second pore (Exit). This entry-to-exit time was in reference to the time the tag resides in the common chamber above both pores, and was also referred to as the pore-to-pore time. In pore-to-pore speed estimation, the pore-to-pore time was divided into the measured distance between the pores for each chip. By definition, the pore-to-pore approach utilizes correlation between the two current signals $I_1$ and $I_2$, since the time starts when the tag leaves the Entry pore and ends with the tag enters the Exit pore. At the voltages applied, DNA in the common reservoir was expected to be fully stretched between the pores (0.34 nm/bp).

Figure 12:
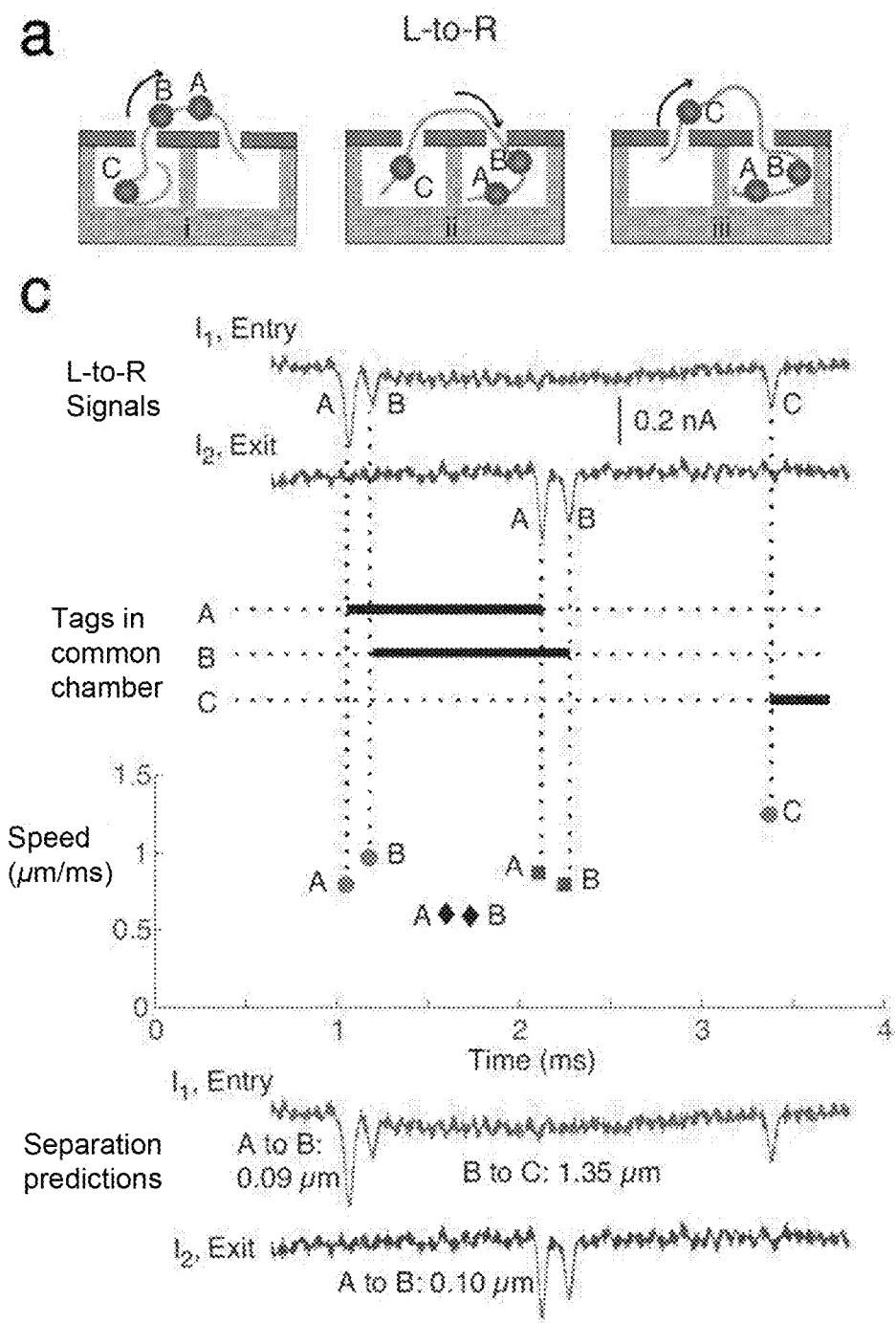
FIG. 12 depicts estimating inter-tag separation distances from dual current signals generated during a multi-scan experiment. The (a) L-to-R and (b) R-to-L illustrations help visualize the relative tag locations that are revealed by the scan signals. The (c) L-to-R and d R-to-L signals were from adjacent scans of a co-captured molecule that was scanned for 48 cycles. In L-to-R, pore 1 is the Entry pore for a tag while pore 2 is the Exit pore. In R-to-L, pore 2 is the Entry pore for a tag while pore 1 is the Exit pore. Entry and Exit are thus relative to the direction of motion of a tag as it passes from pore to pore. The signals and inferred number of tags in the common chamber between the pores versus time are plotted. Illustration (ai) visualizes the period when A and B are in the common chamber, while (aii) visualizes the period after B exits but before C enters the common chamber, etc. The Speed plots shows the computed tag speeds at the Entry and Exit pores, based on tag duration divided into membrane thickness, and tag pore-to-pore speeds computed as the known distance between the pores divided by the pore-to-pore time. Inter-tag separation distance predictions are computed by multiplying the mean pore-to-pore speed within a scan by the time between detected tag pairs, and adding the membrane thickness as a correction (main text). The voltages were set to $V_1$=250 mV for L-to-R and 600 mV for R-to-L, with $V_2$=400 mV held constant. The FPGA monitored $I_2$ for N=2 tags (exit signal L-to-R, entry signal R-to-L), though 3 tags were visible in $I_1$ in both directions.
Figure 12:
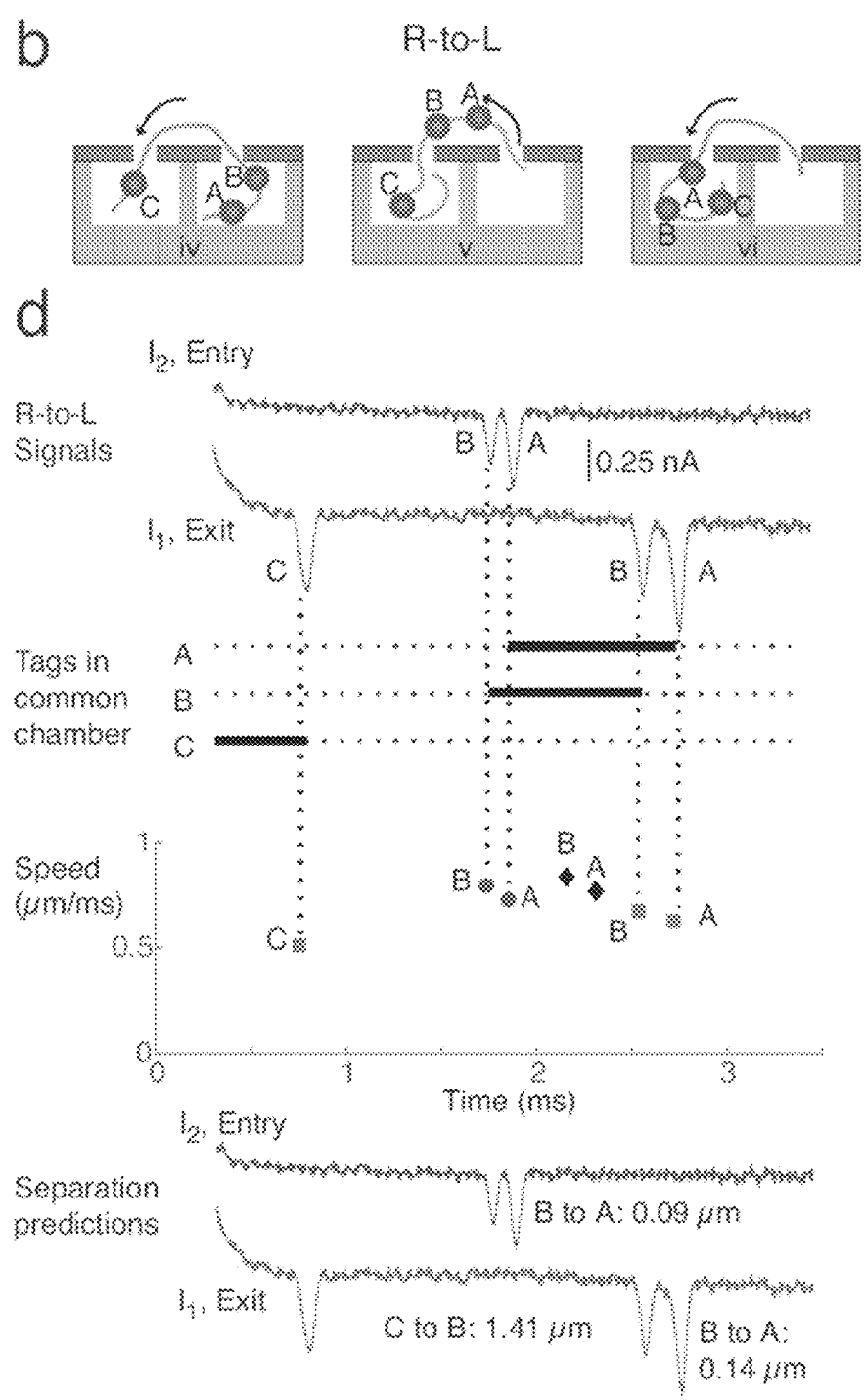

FIG. 12 showed an example of an adjacent pair of scans in a multi-scan event, and demonstrated how inter-tag separation distances can be estimated from each scan. For the L-to-R scan (FIG. 12a,c), tag A then tag B move through pore 1, and about 1 ms later they move through pore 2. The signal pattern reveals that tags A and B were spatially closer than the distance between the pores (0.64 μm). The FPGA was monitoring 12 for two tags during the control logic. During the waiting period after detecting A and B in 12, a third tag C passes through pore 1. Visually, it was also clear from the pore-to-pore transit times of A and B that tags B and C were roughly two times farther apart than the distance between the pores. Upon changing $V_1$ to promote motion in the reverse direction R-to-L (FIG. 12b,d), the first observable tag in $I_1$ was C passing back through pore 1. Again, the logic detects A and B in $I_2$, and this time both tags pass through pore 1 before the logic triggers the Vito promote L-to-R motion. Seeing three tags within $I_1$ was a result of three physical tag separations that were close enough to accommodate 3-tag pore 1 transit within the 2-tag pore 2 detection time window of $I_2$, as implemented on the FPGA. More common was to see two tags reliably in both pores, as detailed in the next section.

For an L-to-R scan, a tag blockade in 12 corresponds to a tag exiting the common reservoir, making pore 2 the Exit in L-to-R, whereas moving R-to-L means a tag in $I_2$ was entering the common reservoir. While 12 showed two tags, the third tag present in $I_1$ for both scan directions yields an opportunity to quantify two tag-pair separation distances. For the signals shown, the number of tags between the pores were plotted, and the tag speeds based on dwell-time and pore-to-pore speeds were also plotted. These speed values versus time provides a glimpse into how the molecule was moving during co-capture tug-of-war, along with the illustrations added for visualization (FIG. 12a, 12b). The pore-to-pore speed was modestly faster for an R-to-L direction (0.8 vs. 0.6 μm/ms), which was consistent with a larger voltage differential for R-to-L motion ($V_1$=600 mV, $V_2$=400 mV) than for L-to-R motion ($V_1$=250 mV, $V_2$=400 mV).

Tag-to-tag separation distances (FIG. 12c,d bottom) were estimated by multiplying the mean pore-to-pore speed within a scan by the tag-to-tag times recorded within that scan, and adding the membrane thickness. Membrane thickness was added to account for the added spatial separation that was equivalent to either tag passing the length of a pore, since tag-to-tag times were computed from the rising edge of a detected tag blockade to the falling edge of the next detected tag blockade. The tag-to-tag distance estimates were shown for both the L-to-R scan and the R-to-L scan. The results suggest that each separation prediction will vary across the two different scan directions. Tag-pair separation distance predictions will also vary due to differences between the tag pore-to-pore speed and the true speed profile during the tag-to-tag time for a given pore. That is, the assumption that the speed between the tags was constant and equal to the pore-to-pore speed was not exactly correct. It likely that this assumption was better when the tag-to-tag times were shorter than the pore-to-pore times, which was the case for tags A and B but not tags B and C in FIG. 12. In any case, if the assumption that the DNA was traveling at the constant pore-to-pore speed was true on average, the average of many re-scans was expected to predict accurate separation distances between any two sequential tags. The average of multiple scan predictions was next computed and tested to see how well the predictions line up with the known separations from the model tagged-DNA reagent.

Combining Scans to Improve Tag-to-Tag Distance Predictions

The error-reduction performance of averaging the distances obtained from individual scans within a multi-scan event was examined. Five different multi-scan events with at least 30 cycles were reported in Table 1. For each event, the averaged distance estimates were shown for each scan direction, and using pore 2 estimates alone as well as merging the pore 1 and pore 2 estimates. The table reports the number of cycles, which was equal to the number of scans in each direction, and the number of tag-pairs that contributed to each separation distance estimate. In all cases, there were fewer distance estimates than scans. For example, for event (v) that had 65 scans in each direction, and for the R-to-L direction, 57 scans produced detectable tag pairs in $I_2$ while 62 tag pairs were detected in $I_1$ for a total of 119 separation estimates. The attrition was because the probability of a missing a tag within any one scan increases with cycle count, as described by equation (1).

The correspondence between the averaged separation distances in Table 1 and the known inter-tag separations that were possible from a position map was assessed. Known distances were computed using the conversion 0.34 nm/bp, which assumes the DNA in the common reservoir was fully stretched between the pores. For event (i), only the R-to-L scan directions were combined and reported for event (i), since the L-to-R data showed significant variation in the pore-to-pore speed (described in SI Section 11). Note that the two scans shown in FIG. 4 were from event (i), which pathologically generated two tag-pair estimates in pore 1 current for the reason described in that figure. If the assumption was tag 6 was absent for the molecule and that tags 4, 5 and 7 were present, the adjacent tag-pair separations for event (i) have their closest match among all possible adjacent tag-pair permutations that were possible according to the position map. Specifically, the map showed 0.1 and 1.5 μm adjacent distance between tags 4-5 and 5-7. It was reasonable to assume that a tag (i.e., tag 6) was absent.

Events (ii-v) in Table 1 show very consistent results across both scan directions, and between both pores when comparing Pore 2 results with Combined results. For these events, only a single separation distance estimate was produced, which was most common for control logic that uses N=2 tag detection in 12 to trigger direction switching. In terms of comparing averaged separation distances and the known inter-tag separations, events (ii) and (iii) correspond most closely to 1.5 μm and 1.3 μm distances between 5-7 and 6-7, respectively, with the 1.5 μm value possible if the tag 6 position was assumed vacant for the molecule of event (ii). And events (iv) and (v) correspond most closely to 0.3 μm and 0.2 μm distances between 4-6 and 5-6, respectively, with the 0.3 μm value possible if the tag 5 position was assumed vacant for the molecule of event (iv).

The correspondence between distance estimates and map-possible permutations was generally not as clean for the individual scans (e.g., FIG. 12) as it was for the averaged scans, and was impossible for scans where tags were missed (representative examples were shown in FIGS. 30, 32 and 33). This demonstrated the value of error reduction by averaging across a multi-scan data set generated for each molecule. Additional data on the velocity profiles for events (i-v) in Table 1 and data for four additional multi-scan events were reported in Table S3 (FIG. 21). The error on each separation estimate was obtained as the error on the mean over the group of estimates, with significant reduction of error achieved through averaging.

The data in Table 1 (FIG. 13) show the power of the flossing approach when the events have tag-to-tag times in $I_2$ that were unambiguously attributable to the same physical set of tags (representative scans with both $I_1$ and $I_2$ signals were provided in FIGS. 26-33). In other data, however, when a tag was missed in $I_2$ within a scan, the two-tag scanning logic will eject the molecule or subsequently shift to a new physical tag pairing on the same molecule, which creates a register-shift in the tag-to-tag time data. An example of this was event (vi) in Table S3 (FIG. 21) with the register-shift scan signals. While this complexity can be visually observed in the data and accommodated manually, it was next sought to develop an alternative approach that could detect and automate analysis for such register shifts.

The alternative method presented next was based on aligning the signal in the time domain based on tag blockade proximity, with the aim of automating the binning of tag-pair times, particularly where there was greater ambiguity in assigning such times across scans.

In the time-bases signal alignment method, the temporal position of each tag relative to the starting time of each scan was first computed. To facilitate alignment, the method must tolerate potentially large differences in tag event shape, and so the tag analysis procedure was modified and based on fitting a model function to each peak based on the convolution of a box with a Gaussian function (SI Section 10). This model can characterize tag blockades that were both broad/rectangular in character or narrow/Gaussian-like.

Figure 14:
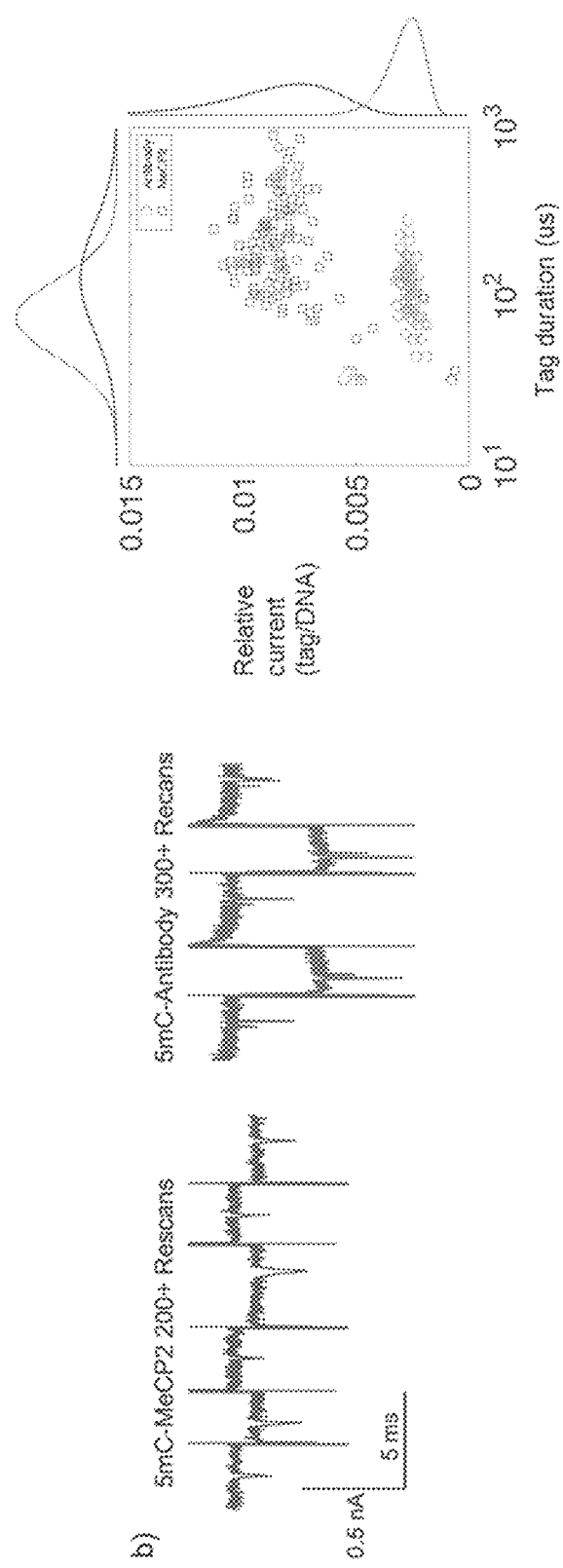
FIG. 14 depicts DNA methylation can be tagged and differentially detected with protein vs. antibody motifs. Multi-read consensus means high confidence in tag cell specificity.

In order to align scans in a systematic way, the algorithm automatically groups tags and removes the translational offset across the scans. FIGS. 14c,f show examples of aligned events and SI section titled "Tag Alignment Procedure" provides a detailed description of the approach. Essentially, the algorithm works by assuming that at least two tags were shwered between two successive scans. In order to identify one of the shared or "common" tags, the algorithm brings each potential tag pair in the two scans into alignment by shifting one scan relative to the other. Note that only translational offsets were applied, i.e., there was no overall dilation of the time-scale. For each one of these possible test alignments, the algorithm computes a measure of alignment error based on the summed squared difference between distinct tag pairs in the test alignment. The algorithm identifies the pairing that yields minimum error as true common tags and implements the translational shift that brings this pair into alignment. Note that this approach yields both the translational offset between the scans and a correspondence table of shared tags between the scans. Working iteratively across all scans in a set the tags observed across the scan can be grouped together and translational offsets removed. The tag group with the largest set of scans was defined to be the origin tag and each scan was shifted so this origin was set to zero. This algorithm outputs a final barcode, or set of averaged relative tag positions, for each set of single molecule scans.

The outputted barcodes were in units of time. In order to calibrate the scans to units of distance, an aggregate translocation velocity corresponding to the scan set was first used. The aggregate translocation velocity was computed as the mean of a subset of the pore-to-pore speeds measured within a multi-scan event, using only those speeds for which the scan displayed a conserved number of tags in both pores. The barcodes were then calibrated in units of distance by multiplying by the mean pore-to-pore velocity. The reported error on the final calibrated tag positions incorporates the error on the velocity and the error in separation via standard propagation. Note that the sharpness of the plateaus indicate the precision achieved through averaging of multiple scans. In particular, when the extracted tag separations was sorted by size, it was found that the data showed distinct plateaus that correspond to the expected separations in the map. Separations that fall off the expected spacings could arise from non-specific binding (e.g., tags attached at random nicks present non-specifically in λ-DNA), or offsets caused by imperfections in the tag blockage analysis algorithm.

In single-pore work, sub-4 nm diameter membrane-based pores that hug PNA-based motifs (15 bp footprint) have demonstrated 100 bp inter-tag distance resolution, while pipette-based pores have resolved at low as 200 bp. It was observed that since the peaks were well resolved for the 300 bp separation (e.g., visible space between tags in FIG. 11 traces), and since slower passage and higher bandwidth were knobs that can be turned in this setup, a lower limit below 300 bp should be achievable. It should be possible to resolve tags that were spaced modestly farther apart than the membrane thickness, in principle (— 105 bp for the current chips).

CONCLUSION

The present inventors have developed an approach that first traps and linearizes an individual, long DNA molecule in a dual nanopore device, and then provides multi-read coverage data using automated "flossing" control logic that moves the molecule back-and-forth during dual nanopore current sensing. From the point-of-view of dual pore technology development, the rescanning approach of the present study overcomes a key challenge: while maximally long trapping-times can be achieved by balancing the competing forces at each pore, sub-diffusive dynamics will persist as speed was reduced, undermining mapping-based approaches that rely on a correspondence between the time at which tags were detected and their physical position along a DNA. In the present study approach, sub-diffusive dynamics were avoided during bidirectional scanning of the molecule by using speeds that permit reliable tag detection while being high enough to avoid broad translocation time distributions. Genome scaling was the potential to move beyond experiments with short DNA constructs and tackle complex, heterogeneous samples containing fragments in the megabase size drawn from Gbp scale genomes. For genome scaling, single-molecule reads must have sufficient quality (e.g. contain sufficiently low systematic and random errors) to enable alignment to reference genomes and construct contigs from overlapping reads drawn from a shared genomic region. This was the only way to identify long range structural variations that were masked by short read methods (i.e., via NGS), and in some cases masked even by long-read sequencing. The approach can be applied to longer molecules with more complex tagging patterns, possibly using repetitive scanning at targeted regions to gradually explore the barcode structure. In the applied context of epigenetics, the technique of the present study combined sequence-specific label mapping, using the same chemistry here or other nanopore-compatible schemes that have a low spatial footprint per label, with methylation-specific label detection.

Materials and Methods

Preparation of Mono-Streptavidin Tagged λDNA Reagent

5 μg of commercially prepared λDNA (New England Biolabs) was incubated with 0.025 U of Nt.BbvC1 in a final volume of 100 μl of 1× CutSmart buffer (New England Biolabs) to introduce sequence specific nicks in λDNA. The nicking reaction was incubated at 37° C. for 30 minutes. The nicking endonuclease Nt.BbvC1 has the recognition sequence, 5'-CC↓TCAGC-3' and there are 7 Nt.BbvC1 sites in λDNA. Nick translation was initiated by the addition of 5 μl of 250 μM biotin-11-dUTP (ThermoFisher Scientific) and 1.5 U of *E. coli* DNA polymerase (New England Biolabs) and incubated for a further 20 minutes at 37° C. The reaction was quenched by the addition of 3 μl of 0.5M EDTA. Unincorporated biotin-11-dUTP was removed by Sephadex G-75 spin column filtration. To create mono-streptavidin tagged λDNA complex, mono-streptavidin was added to the G-75 purified biotin labeled DNA to a final concentration of 50 nM and incubated at room temperature for 5 minutes to allow the biotin-mono-streptavidin interaction to saturate. The mono-streptavidin tagged λDNA complex was then used directly in nanopore experiments.

Fabrication Process of the Two-Pore Chip

The fabrication protocol has been described previously. Briefly, the microchannel was prepared on glass substrate and SiN membrane on Si substrate separately. The all-insulate architecture minimized the system capacitance. Thus the noise performance was optimized. Initially, the shapes were dry-etched into two "V" shape, 1.5 μm-deep micro-channel on the glass in a 8 mm×8 mm die, with the tip of the "V" 0.4 μm away from each other. Next 400 nm-thick LPCVD SiN, 100 nm-thick PECVD SiO2, and 30 nm-thick LPCVD SiN was deposited on Si substrate. To transfer the 3-layers film stack to glass substrate from the Si substrate, d the two substrates were anodic-bonded, with the micro-channel on glass facing the 3-layers film stack on Si. To remove the Si substrate, the 430 nm SiN was first dry-etched away on the backside of Si. Then the Si substrate was etched away using hot KOH, revealing the 3-layers films stack on the glass. The 3-layers films stack provides mechanical support to cover the micro-channel on glass, while it was too thick for nanopore sensing. So a window was opened in the center for nanopore. To achieve that, a 10 μm×10 μm window was dry-etched in the center through the 400 nm-thick SiN mask into the 100 nm-thick SiO2 buffer layer. Then the leftover 100 nm-thick SiO2 layer was etched away using hydrofluoric acid, revealing the single 35 nm-thick SiN membrane layer. At last, two nanopores were drilled through the membrane using Focused Ion Beam at the tip of the two "V" shaped channels.

Nanopore Experiments

All the nanopore experiments were performed at 2 M LiCl, 10 mM Tris, 1 mM EDTA, pH=8.8 buffer. The two pore chip was assembled in home-made micro-fluidic chunk, which guide the buffer to channel 1, channel 2, and the center common chamber. Ag/AgCl electrodes were inserted to the buffer to apply voltage and measure current. The current and voltage signal was collected by Molecular Device Multi-Clamp 700B, and was digitized by Axon Digidata 1550. The signal was sampled at 250 kHz and filtered at 10 kHz. The tag-sensing and voltage control module was built on National Instruments Field Programmable Gate Array (FPGA) PCIe-7851R and control logic was developed and run on the FPGA through LabView.

Data Analysis

All data processing was performed using custom code written in Matlab (2018, MathWorks). The start and end of each scan and event were extracted from the FPGA state signal (SI) for offline analysis. During real-time tag detection on the FPGA, the presence of tag was detected in the control logic if any sample falls 70 pA below the baseline and lasted at least 12 μs. During off-line analysis, for the analysis reported in FIG. 4 and Table 1, tag blockade quantification during each scan was performed as follows: the open pore baseline standard deviation was calculated using 500 μs of event-free samples (a); the DNA co-capture baseline/DNA was determined using the mean of 100 tag blockade-free samples; a tag blockade candidate was detected where at least one sample falls below $I_{DNA}$ —6σ, i.e., sufficiently below the DNA co-capture baseline; a tag blockade was quantitated where the blockade candidate has samples that return within 1σ below IDNA, and the tag duration was computed as the full width at half minimum (FWHM), where the half minimum was halfway between the lowest sample below the DNA baseline and the DNA baseline. The alternative tag profile characterization via least-squares fitting that was utilized for the alignment strategy data in FIG. 5 was described in SI section 12. Tag-to-tag times were computed from rising edge to falling edges using the FWHM time transition (edge) points, and pore-to-pore times use the rising edge of the tag blockade at the entry pore, to the falling edge of the corresponding tag blockade at the exit pore. Pore-to-pore times were computed by assigning entry tags to have one matching exit tag, utilizing the first exit tag not previously assigned and within a time limit of 10 ms. Cases where missed tags in analysis produced incorrectly assigned pore-to-pore times occurred ~9% of the time (see tag-pair and pore-to-pore time counts in Table S3; FIG. 21), and were manually trimmed. Pore-to-pore times were utilized to compute pore-to-pore speed on a per scan basis (FIG. 4, Table 1, Table S3; FIG. 21). Compensation of transient decay in $I_1$ following step changes in $V_1$ is.

Supplementary Materials

1. Tug-of-War Experiment with λDNA

FIG. 16 showed the details of tug-of-war experiment with λDNA. The tug-of-war experiment was run with λNA molecules in advance to calibrate the 2-pore device. FIG. 16a showed the full steps of the tug-of-war experiment with corresponding current trace I1 and I2 in FIG. 16b. Initially the common chamber was filled with 20 pM λDNA. The idle state (state pre-i, 0-50 ms) of the system was set to be V1=300 mV, V2=300 mV. Once a downward spike showed up in I1 at 15 ms, the FPGA measured the spike. If the spike jumps at least 70 pA below the baseline and lasts at least 0.5 ms, the system treats it as an intact molecule and get ready to progress to state pre-ii. Otherwise the system stays in state pre-i to be ready for the next trigger. That false positive spike may cause by some DNA fragments or free leftover protein when the tagged λDNA was prepared. Then voltage 1 was set $V_1$=0 mV in state pre-ii (50-70 ms) to let the λDNA molecule relax to its equilibrium conformation. After that, voltage 1 was set $V_1$=−200 mV to drive the molecule back to pore 1 in state pre-iii. Notice V1 was kept $V_1$=300 mV unchanged after the spike for 30 ms at state pre-i. The purpose was to push the molecule a distance away from the nanopore. Thus the molecule wouldn't run back that fast to show up in the exponentially decay baseline, which was hidden in the axis break around 70 ms. Because it was hard to trigger a translocation in a drifting baseline. When the molecule did come back to pore 1, it generated an upward spike around 80 ms (see the insert). Before the translocation completed, V1 was turned off within 0.3 ms in state i to let the head of λDNA dangling at the common chamber, waiting to be caught by pore 1, while keeping the rest of the λDNA anchored in pore 1. V2 was also increased to be 500 mV in state i to generate a stronger force to catch that head of the λDNA. At around 165 ms, the head of the λDNA molecule reached pore 2, generating another downward spike (see the insert). $V_1$ was then set to be 400 mV to pull the other end of the molecule in the opposite direction, reaching the tug-of-war state ii. Because the pulling force in pore 1 was still weaker than that in pore 2, the molecule still slid towards pore 2. The molecule finally exit pore 1 and pore 2 sequentially at around 215 ms at state iii. Then the system went back to the idle state i for another cycle. The I2 baseline did not come back to the original value in state i, which was caused by the cross-talk between the two pores. I1 showed a huge spike and exponentially decay baseline each time after changing its value each time, which was caused by the capacitance of the chip. Adding the three states, pre-i, pre-ii, and pre-ii, provides two advantages. First, compared to filling the reagent in channel 1, filling the reagent in common chamber saves one step of pumping the reagent through the channel, which enables us to exchange different reagents more efficiently. Second, the single pore translocation in state pre-i screens out the short fragments. The tug-of-war experiment was run in state i, ii, and ii with the molecule which showed long enough duration in state pre-i, which increases the efficiency of grabbing the intact molecules.

As stated in the main text, the tug-of-war duration was defined as the time spent at state ii. V2 was kept at V2=500 mV in state ii unchanged and adjust Vito measure the duration. FIG. 16c showed the mean duration with error bar. The Duration (ms) Vs $V_1$ (mV) showed a bell curve. The duration reached its maximum of 110 ms at the balanced voltage $V_1$=500 mV, while the duration showed one magnitude smaller value at unbalanced voltage.

Because the molecule moved faster when the net force from either pore 1 and pore 2 was larger. The single pore duration was also measured in state pre-i and plot its mean duration, 3.4 ms, in the grey area, illustrating the same molecule showed more than one magnitude shorter duration in single pore translocation compared to that in tug-of-war. Considering the state ii was the most critical state in the process, the current trace pair normally only shown in that state. FIG. 16d showed event example with λDNA at the voltage setting of $V_1$=200 mV, $V_2$=500 mV.

2. FPGA Logic of Multi-Scan Experiments

Figure 17:
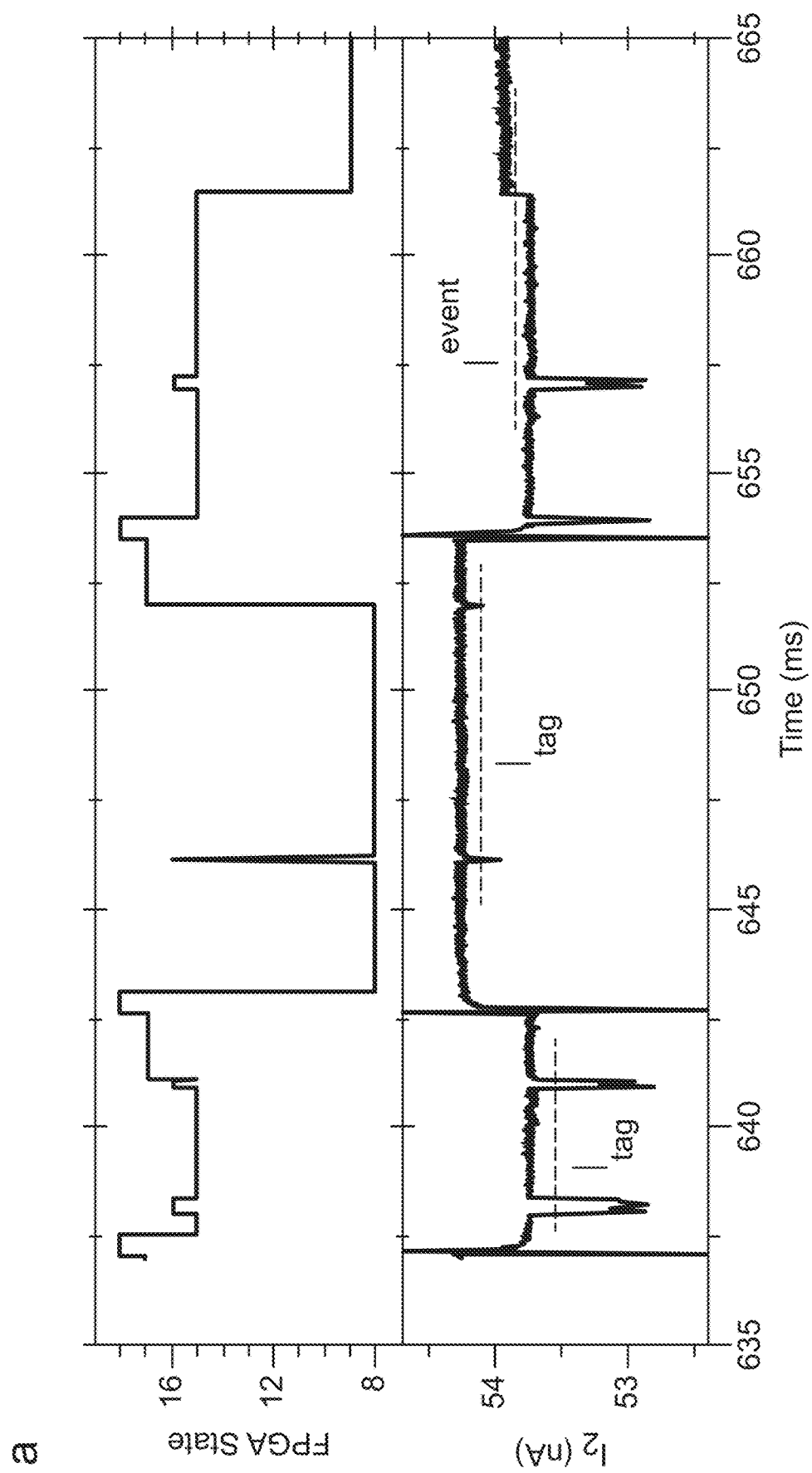
FIG. 17 depicts FPGA logic of the multi-scan experiment. (a) Signal of 12 and FPGA state from the end of the event shown in FIG. 10. The red and black dashed line shows the triggering threshold of tag and event respectively. (b) FPGA logic flowchart. The blue boxes indicate the system state with magenta numbers refers to the FPGA state in (a). The black boxes indicate decisions. The green boxes indicate actions. The arrows between the boxes indicate how the system flows between different steps.
Figure 17:
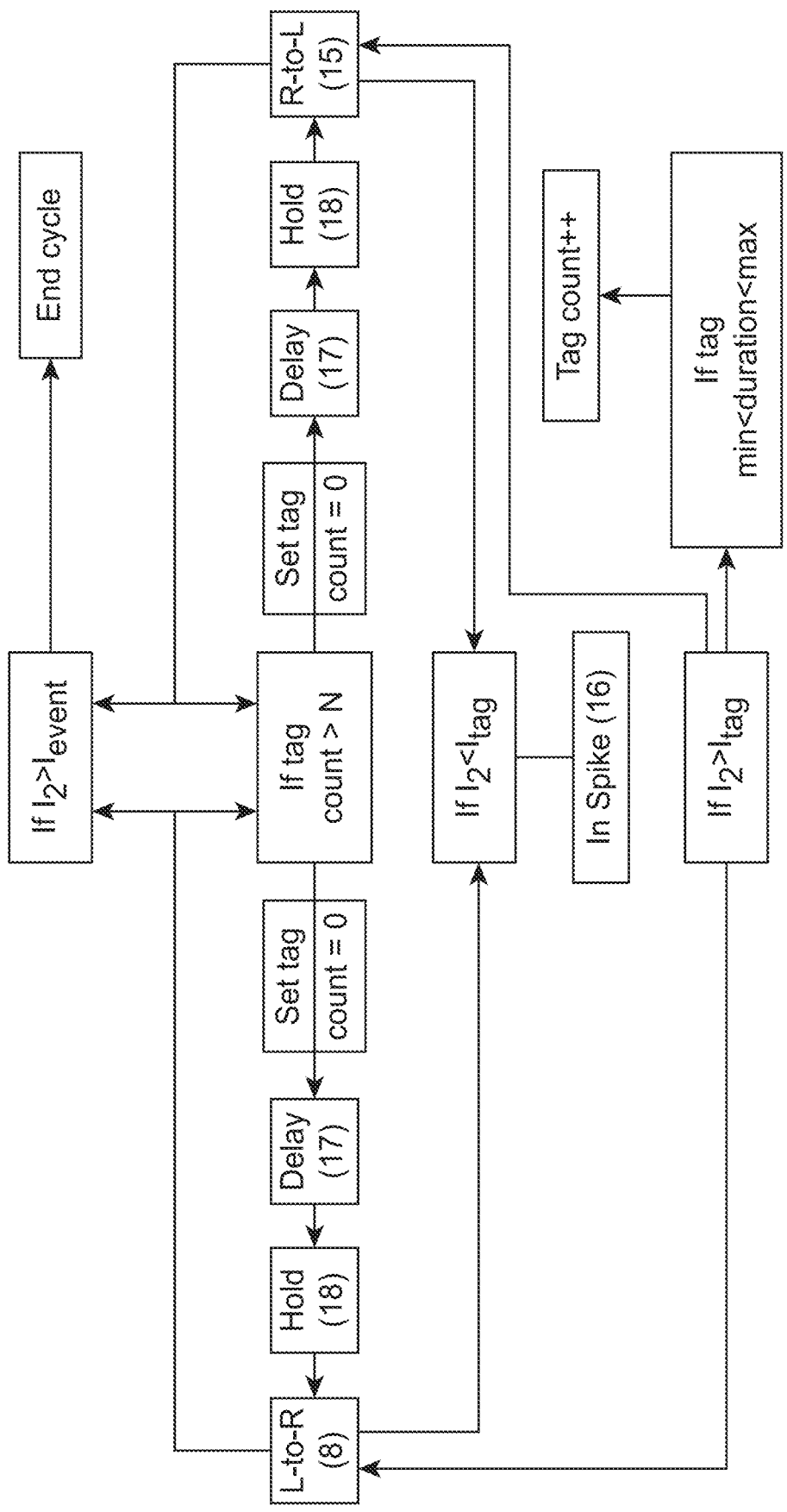

FIG. 17 illustrates the FPGA logic of the multi-scan experiments. FIG. 17 a showed the signal of I2 and FPGA state from the last cycle of the event in FIG. 2a in the main text. I1 was hided here since the FPGA only triggers the spikes in I2. Pore 2 performs as the sensor while pore 1 performed as the controller in the study design. The FPGA State was the integer numbers reported by the FPGA to reveal its internal state. FIG. 17 b showed the FPGA logic flow. The flow was designed to control the system switch between two major states: L-to-R (8) when the molecule moves from left to right, and R-to-L (15) when the molecule moves from right to left. The In Spike (16), Delay (16), and Hold (18) were the transitional states. The FPGA calculate the baseline as the mean of 12 up to 10 ms, while the 12 samples during the In Spike (16) was excluded. And the FPGA refreshes the baseline value once the major state (8 or 15) changes. I tag and I event were relative values comparing to the baseline to trigger the spike and the end of the event. The system was in state 15 during 637 ms to 642 ms. 12 jumped below I tag in 638 ms, triggering the system to enter state 16 when the system started to count the duration. Once 12 jumped back above I tag, the system switched back to state 15. If the tag duration was between the minimum (7 μs) and maximum (2 ms) of the user settings, the internal tag count increased by 1. Similar process happened in 641 ms, when the tag count increased by another 1. Once the tag count increased beyond a user input N, which was set N=2 in this experiment, the system entered the process of switching to the other major state (8). To avoid the spike showing up too soon after state switching, a delay state 17 was designed for delaying 1.5 ms to push the last tag move further away the nanopore, which was shown in 642 ms and 652 ms. As soon as the system switch the major states, the tag counter was reset to 0, ready for the new triggers. Note there was another 0.5 ms-long hold state (18) when triggering was disabled right after switching the voltage, which was around 643 ms and 654 ms in the signal. Because the system needs time to calculate the baseline value. As a result, the system missed the spike in 654 ms. Thus the tag counter did not reach N even after the two tags already showed up. As a result, 12 finally jumped above I event at 661 ms, indicating the molecule left pore 2. Then the event ended.

3. Summary of the Last Cycles in the Multi-Scan Experiments

FIG. 2d in the main text showed the system caught the scan at the probability of p=0.89, which was pretty high. Though the last cycles were studied to figure out the reason why the molecule escaped the multi-scan. FIG. 18 showed the signal of the FPGA state and 12 of the last cycles, which include the (n−1) th and n th scan.

FIG. 18a showed a missing tag in the n th scan. The FPGA calculates the baseline at the hold (18) state. Because the baseline changed its value when the $V_1$ changes due to cross talk. Any spikes show up during state 18 would not be detected. Missing that tag, the tag counter can not reach to the user set value N. Thus system wouldn't trigger to switch the major state to continue the multi-scan. The molecule exits the pore at 11 ms.

FIG. 18b showed another case when the FPGA detected a false positive in the (n−1) th scam. The tiny spike around the 1.8 ms might be caused by some free protein instead of a real tag along the DNA. Thus the system switched the major state without reaching tag count N=2 at the (n−1) th state. As a result, there would be no second tag to trigger in the n th state. The molecule exits the pore at 12.5 ms.

FIG. 18c showed a false negative spike in the n th scan. Sometimes the tag get stuck in the pore and produces a long spike. Once its duration exceeds the maximum value (2 ms) in the setting. The FPGA won't count it a valid one. Failing to switch to the other major state, the molecule exits at around 15 ms.

FIG. 18d showed the molecule exits the pore at the delay (17) state before the FPGA switch to the other major state. The molecule exits the pore at around 5.5 ms, before the FPGA switch to the other major state at 6 ms.

Empirical values were set to optimize the system to maximize the total count of scans in each event. Spike duration was set with 7 μs minimum and 2 ms maximum, delay for 1.5 ms and hold for 0.5 ms. Too long delay time in state 17 would cause more failing cases in FIG. 18 d, while short delay time would cause more failing cases in FIG. 18a. Because the tag tends to be driven back too soon if it was too close to the pore. Too long hold time in state 18 causes more failing cases in FIG. 18a, while too short hold time masses up the calculation of baseline value. Wrong baseline value would cause more false positive or negative spike detection, which increases the failing cases in FIG. 18b and FIG. 18c.

4. Multi-Scan Experiments with Three-Tags Triggering

FIG. 19 showed the experiment with three-tags triggering. FIG. 19a showed the signal trace from a 6 cycle event. FIG. 19b showed the zoom-in signal of the 2 nd cycle. FIG. 19c showed the distribution of scans count per event.

5. Tag Location Map

For the tag location map, the nicking sites location was along the λDNA. The NbBbvCI nicking enzyme locates the sequence of "CCTCA↑GC" and cut one strend. Then the biotinylated dNTP binds the nicking sites. So the monostreptavidin tags were supposed to locate at the nicking sites. The distance between any two binding sites, from short to long, were d 45 was 301 bp: 102 nm, d 23 was 323 bp: 110 nm, d 56 was 614 bp: 209 nm, d 46 was 915 bp: 311 nm, d 67 was 3982 bp: 1354 nm, d 57 was 4596 bp: 1563 nm, d 47 was 4897 bp: 1665 nm, d 12 was 10135 bp: 3446 nm, d 13 was 10458 bp: 3556 nm, d 34 was 12451 bp: 4233 nm, d 35 was 12752 bp: 4336 nm, d 24 was 12774 bp: 4343 nm, d 25 was 13075 bp: 4446 nm, d 36 was 13366 bp: 4544 nm, d 26 was 13689 bp: 4654 nm, d 37 was 17348 bp: 5898 nm, d 27 was 17671 bp: 6008 nm, d 14 was 22909 bp: 7789 nm, d 15 was 23210 bp: 7891 nm, d 16 was 23824 bp: 8100 nm, d 17 was 27806 bp: 9454 nm.

The nicking sequence along the lambda DNA was found. The base pair distance between two adjacent sites were learned. 0.34 nm/bp was used to calculate the distance between the tags.

6. Tag Profile Characterization Via Least-Squares Fitting

In this section the approach for the study was described for obtaining peak-position and peak width at half-maximum using least-squares fitting of a model tag blockade profile. First, the raw multi-scan event was broken up into all component L-to-R and R-to-L scans. Then, the data was inverted (by reversing the sign of the current values) and Matlab's findpeaks algorithm was used to identify local maxima corresponding to the individual tag blockades. For pore 1 (entry pore for L-to-R polarity), voltages were changed upon termination of a scan to enable directional reversal, inducing capacitance transients in the current. These transients xacare fit to an exponential model. Note that, prior to fitting the transient, a fixed region of 400 μs around each identified tag was removed to ensure the tag blockades do not interfere with the background fit. The fitted transient background for the pore 1 channel was removed and then each tag blockade was fitted to a model profile. While the transient was mostly removed, there was a small residual within about 1 ms of the scan start, as the exponential was not an exact model. There was no risk of mistaking this residual as a tag blockade, as it corresponds to a current increase above baseline and occurs in the same location for each rescan.

This model profile has the following functional form:

$$I(t) = I_{b1} + I_{b2}t - \frac{I_o}{2}\left[erf\left(\frac{t-(t_o-\Delta t/2)}{\sqrt{2}\,\sigma}\right) - erf\left(\frac{t-(t_o+\Delta t/2)}{\sqrt{2}\,\sigma}\right)\right] \quad S2$$

This form was based on the convolution of a box of width $\Delta t$ and height Io with a normalized Gaussian of width $\sigma$. In limit that $\Delta t \gg \sigma$ this model has the form of a broadened box; in the limit $\Delta t \ll \sigma$ it has the form of a Gaussian function. For the purposes of tag-profile characterization, this model has the advantage that it can describe both tag transits of long duration with a broadened box shape and rapid tag transits with a more peaked shape. The width at half maximum can be obtained as a function of $\Delta t$ and $\sigma$ (in the limit $\Delta \gg \sigma$, the width was $\Delta t$, in the limit $\sigma \ll \Delta t$ the width was that of a Gaussian function, in the intermediate case, the width at half-maximum was computed numerically as a function of $\Delta t/\sigma$ and then interpolation used to obtain the width from any combination of t and $\sigma$). In addition, it was found that the fitting was more robust if a linear function was added to account for any residual background variation that was not captured by the exponential fit. In practice, this fitting was performed using Matlab's lsqcurvefit for each tag over a range of fixed duration (typically ~0.5-1 ms) centered on the location of the preliminary tag position identified by findpeaks. The parameters determining the linear background (Ib1 and Ib2) were determined by averaging the background over 60 μs at the beginning and end of the tag-centered interval (in cases where the background was flat, note that Ib2≈0). For pore 2 (exit pore on L-to-R) the same procedure was applied, except there was no need to remove a capacitance transient as the voltage at pore 2 was held constant. Note that the model can accommodate both the peaked Gaussian shape of the tag blockades and the flatter box-like shape of the blockades.

7. Tag Alignment Procedure

The details of the tag alignment algorithm were described herein. Each successive scan represents a measurement of an underlying binding pattern of tags over a certain region of the molecule. The scans in each series of fixed polarity (i.e. L-to-R or R-to-L) have a relative translational offset, arising from the fact that different portions of the molecule were observed in each scan. There was also stochastic variation in tag positions, arising from Brownian fluctuations (see FIG. 16a, 16e, these events correspond to results shown in manuscript FIG. 5). These effects complicate correct association of tags across multiple scans (i.e. how was it ensured that a tag observed in scan i corresponds to the same tag in scan j, with "same" implying that the tags correspond to a single tag at the same sequence position?). The objective of this algorithm was to introduce a systematic procedure for aligning scans in a given series (L-to-R or R-to-L for pore 1 or pore 2) by identifying the correct corresponding tag pairs between successive scans and then removing translational offset between the scan pairs.

The core of the algorithm was a function, pairalign, that computes a measure of alignment error based on the squared difference between the i th and j th scans in a given scan set. This function assumes that at least two tags were shared, or were 'common,' between the i th and j th scan. In order to show that this assumption was valid for the multi-scan data, the spacing between the tags in each scan can be computed and compared. What was observed typically were cases where the spacing in each scan fluctuates around a fixed mean value (see FIG. 20b), or occasionally bimodal situations where two mean spacing values were observed (see FIG. 20O. In bimodal situations, the spacings often exchange at a scan where three tags were observed. Thus, it was reasonable to assume that two common tags will be present between successive scan pairs (scans i and j=i−1).

In order to identify the common tags in a scan pair, pairalign computes a measurement of alignment error over all potential alignments of the two scans. Each of these potential, or test alignments, was determined by choosing a tag pair between scan i and j and then shifting scan I by the correct time interval to bring this chosen tag pair into alignment (This tag pair was called the "aligned pair"). Then, omitting the aligned pair, the squared distance was computed for all possible tag pairs that can be formed between the scans. The list of these possible pairings was sorted by squared difference and the distinct pairings with minimum squared difference were obtained (note that the number of distinct pairs was equal to min(n tag,i, n tag,j) where n tag,i was the number of tags on the i th scan and n tag,j was the number of tags on the j th scan). The overall alignment error, for a given choice of aligned pair, was the sum of the squared differences of these distinct pairings with minimum squared difference. The aligned pair taken as the correct common tag between the two scans was the aligned pair that yields the minimum overall alignment error. As a consequence of this procedure, which identifies a set of pairings between tags in the scan, a correspondence table can be constructed between the tags in scan i and scan j, yielding all common tag pairs shared between the scans. Blue circles were spacings for scans with only two tags observed (for which there was only one spacing). Red squares and magenta triangles represent the two distinct nearest neighbor spacings when three tags were observed. (g) Aligned tag positions; meaning of data color and shape scheme same as in (e). (h) Aligned and distance calibrated tag positions: the data color and shape scheme now reflects the group assignments and corresponds to true physical tags (tag A, blue circles; tag B, red squares and tag C magenta triangles). Black circles were final averaged tag positions corresponding to tags A, B and C. Note that the first scan corresponds to an alignment with an error over threshold and was removed from computation of the averaged tag position (indicated by cross).

Figure 20:
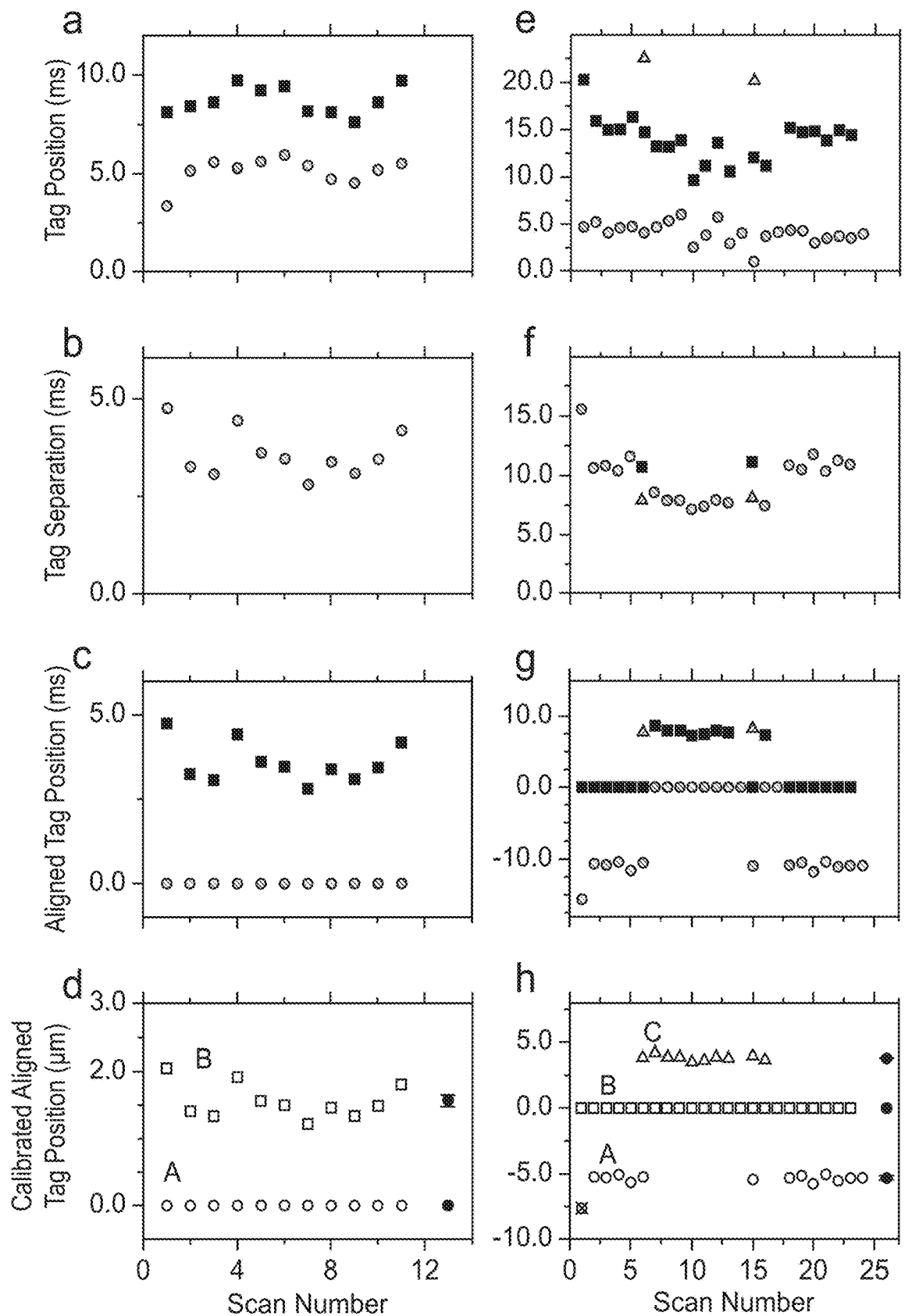
FIG. 20 depicts tag alignment procedure. (a) Example of tag-position versus scan number for an event with two tags (blue circles, tag measured closest to scan start in each scan, red squares tag observed furthest from scan start). (b) Spacing between tags as a function of scan number for event in (a). (c) Aligned tag positions for event in (a). The distance calibrated and aligned tag position for event in (a) with final averaged tag positions (here blue circles correspond to associated measurements for tag A, red squares correspond to associated measurements for tag B). (e) Example of tag-position versus scan number for an event with three tags (blue circles, tag position closest to event start, red squares tag at intermediate distance, magenta triangles tag observed furthest away from event start). (f) Spacing between tags for event in (e).
Figure 22:
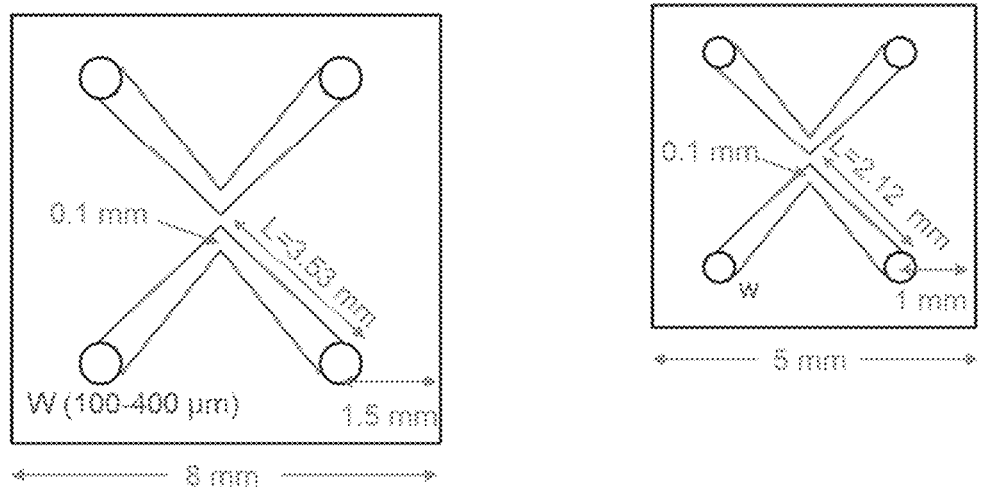
FIG. 22 depicts a non-limiting example of the geometric configuration of a nanopore device of the present disclosure.
Figure 23:
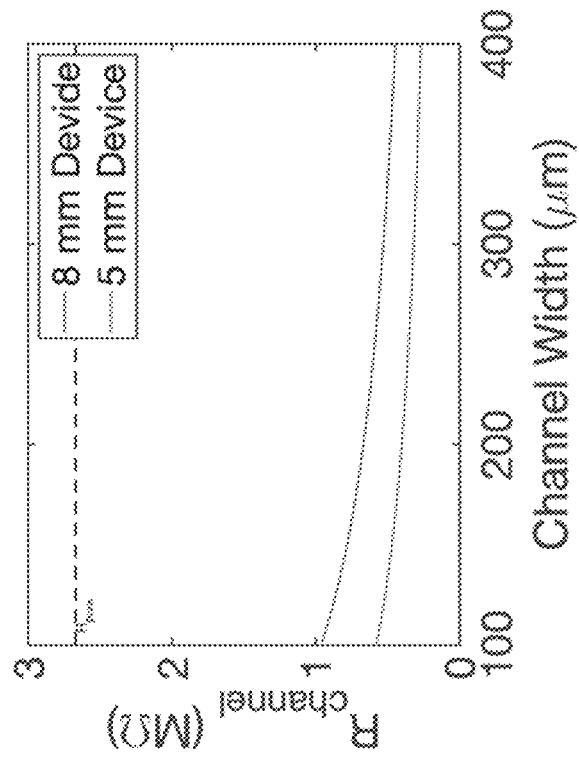
FIG. 23 shows a graph depicting a correlation between channel resistance and channel width for devices with different geometric configurations.
Figure 24:
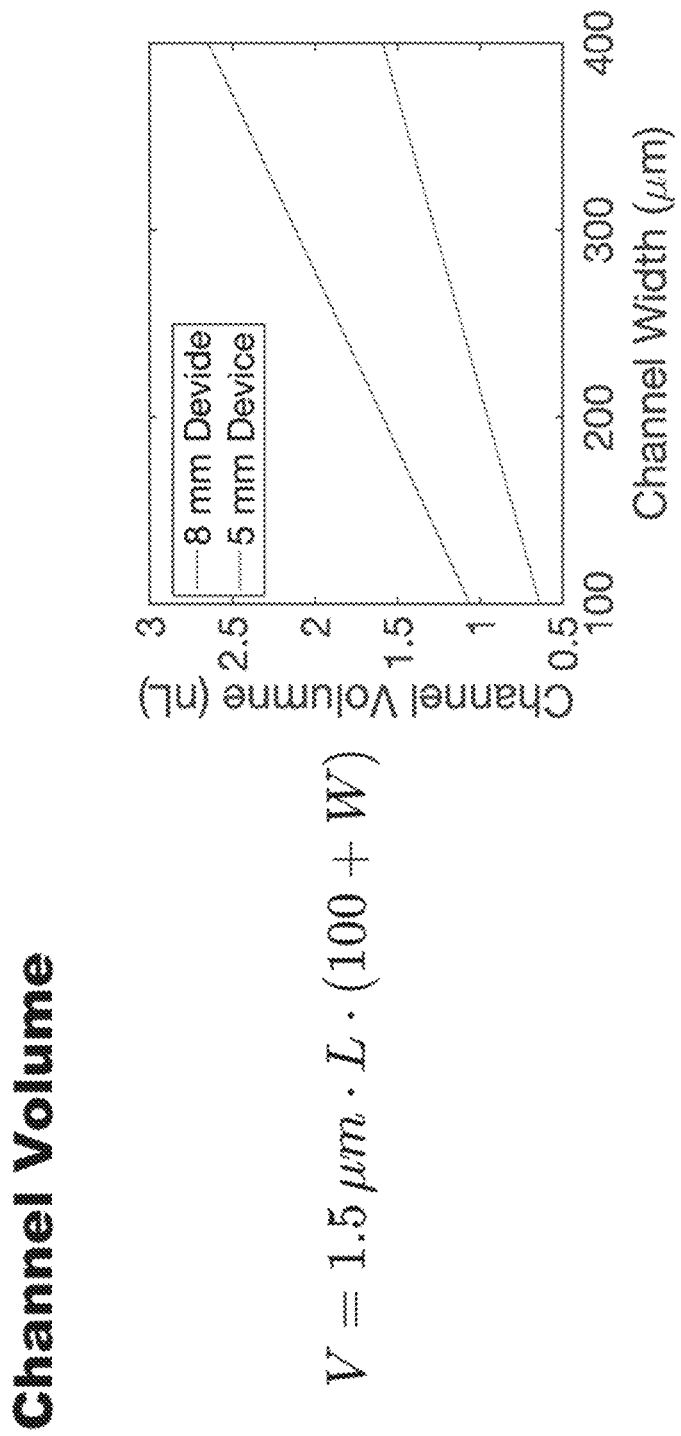
FIG. 24 shows a graph depicting a correlation between channel volume and channel width for devices with different geometric configurations.
Figure 25:
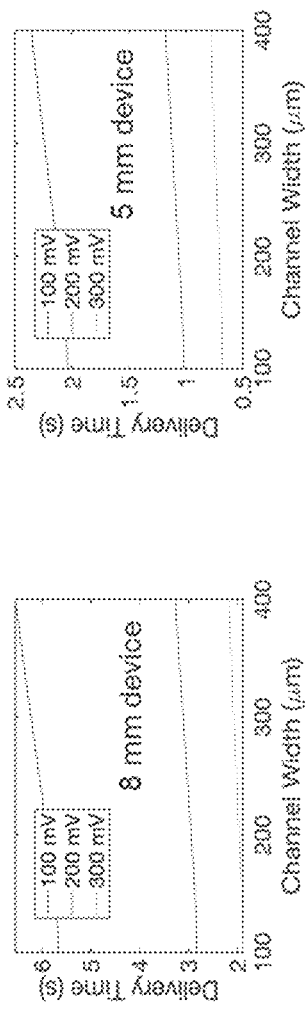
FIG. 25 shows a graph depicting a correlation between polynucleotide delivery time and channel width.
Figure 26:
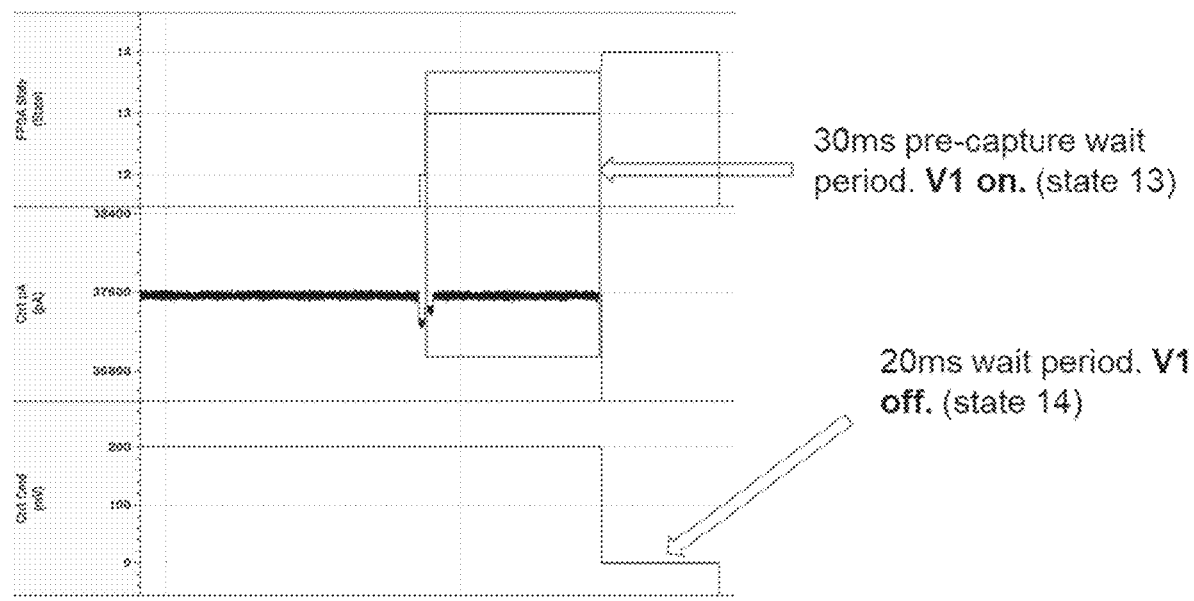
FIG. 26 depicts a non-limiting example of wait time periods during "pre-capture" as shown in FIGS. 20A-20C, where the target polynucleotide in "pre-i" comprises a wait time period of approximately 30 ms, thereby allowing the target polynucleotide to be pushed further into the first fluidic channel in a first direction; and a second wait time period "pre-ii", where the voltage is adjusted to 0 mV "OFF" for approximately 20 ms before changing the direction of the target polynucleotide. The total time period was approximately 50 ms.
Figure 27:
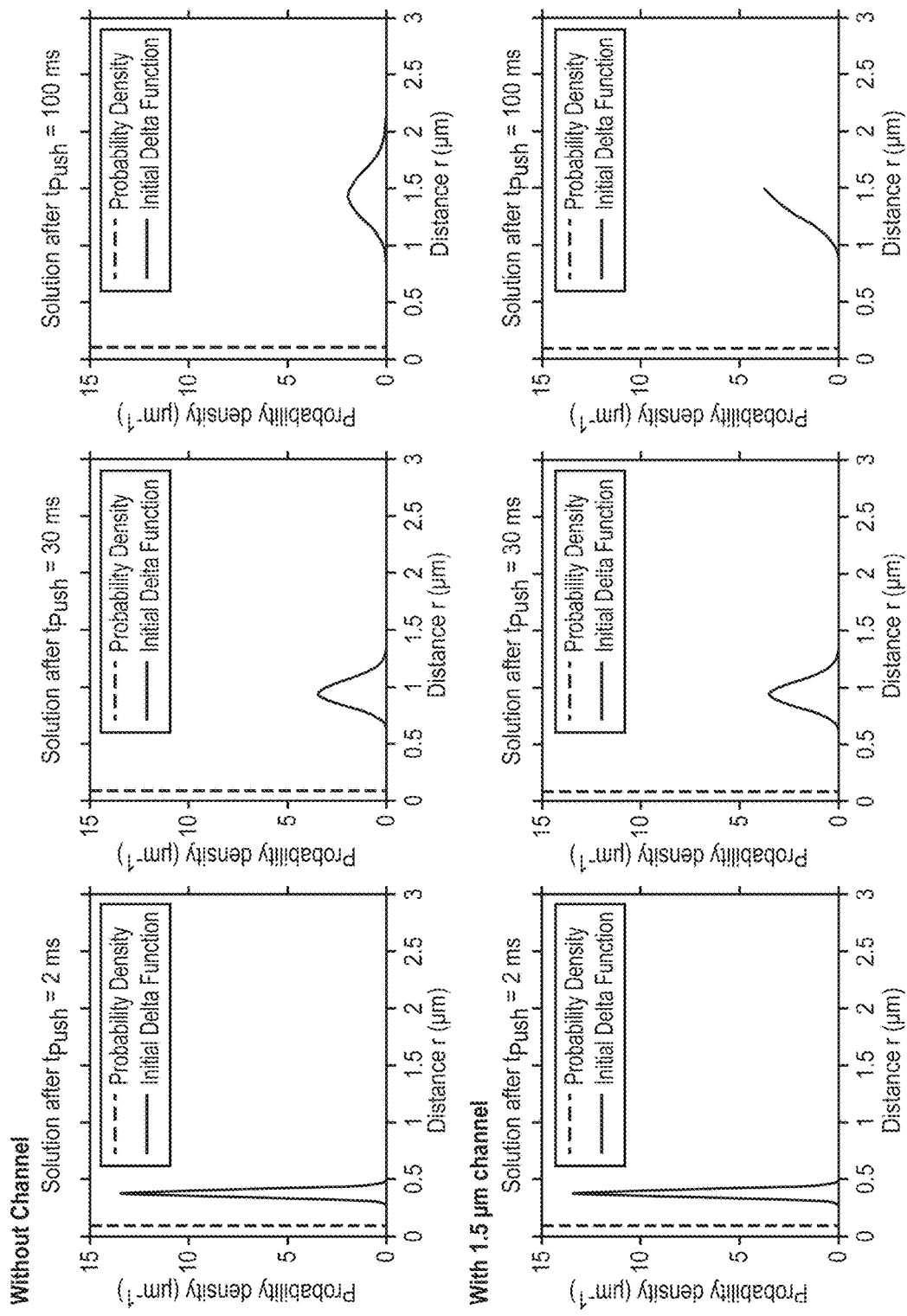
FIG. 27 shows a non-limiting example distribution of the target polynucleotide after translocation with and without a channel.

Pairalign was applied between successive scan pairs in a scan set. The correspondence table, applied iteratively, enables association of tags observed in each scan into groups that correspond to the true physical tags present on the molecule (FIG. 20d,20h). The initial number of groups corresponds to the number of tags in the first scan. If scan i has more tags than scan j, then new groups were introduced.

A problem occurs when a scan has only one tag. If scan i has one tag, then the common tag in j=i−1 was chosen as the tag with minimum separation to the one tag in scan i. If scan j=i−1 has only one tag, then the algorithm seeks to bring the i th scan into alignment with the i−2 scan. Another problem was that tags corresponding to different groups can be inadvertently associated together, particularly if a third tag was missed in the scan bordering the groups. The code seeks to prevent this in the following way. If the overall alignment error of the i th and i−1 scans was greater than a preset threshold, yet the alignment to successive tags was below threshold, then this indicates a junction between two different tag groups that were incorrectly grouped together. The code will check the alignment between the i th scan and scans preceding the i−1 scan that yielded the large alignment error. All alignments that also yield an error over the threshold value were assumed to belong to a different group and assigned a new group number. Groups which correspond to only one scan were further checked by associating the scan with all other scans; if alignments were found yielding an error below the threshold value than these groups were consolidated (example was scan 15 in FIG. 20h). If a single over-threshold scan cannot be associated with additional scans, i.e. was a group corresponding to only one scan, it was removed from the analysis as an outlier (an example was the first scan for event shown in FIG. 20h). At this point the largest group was defined to be the origin tag. All scans were shifted by the amount required to bring the origin tag to zero. For a scan i that does not contain the origin tag, the scan was associated through a common tag pair to a scan j that does contain the origin tag. The scan I was then shifted to bring the common tag to the same position as in scan j. This step removes residual translational offset. Lastly, a final single molecule barcode was constructed by averaging together all tag measurements that belong to a given group (FIG. 20d, 20h). The error on a given tag location can be obtained as the standard-deviation of the mean for the group.

Figure 3:
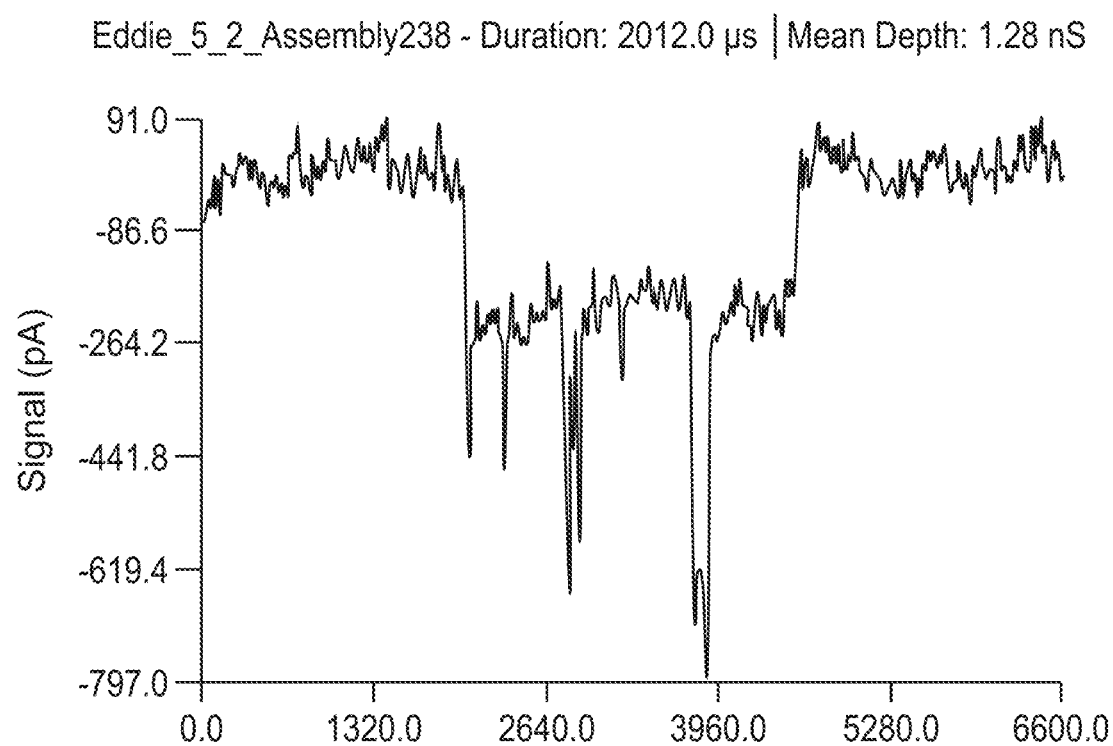
FIG. 3 depicts an example of measuring ionic current over time as a detection parameter of a DNA molecule in a single pore and validation of tagging the DNA molecule with one or more probes.
Figure 3:
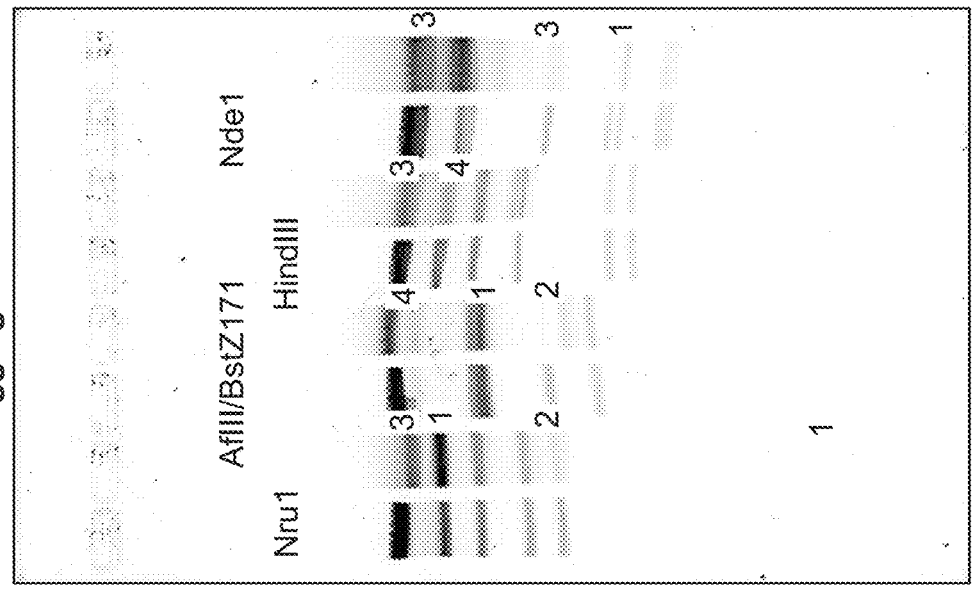

The pore-to-pore speed coefficient of variation (CV, equal to standard deviation divided by the mean) provides a metric that can be used to assess how reliable the distances estimates were, since its a measure of heterogeneity of motion from scan to scan. The pore-to-pore speed CV was high at 83% for the L-to-R scans and more reasonable at 20% for the R-to-L scans for event (i) (also event (i) in main text Table 1). As described in main text FIG. 3, only the shorter tag-pair distance estimates were available in $I_2$ for event (i), and so the second longer tag-pair spacing (B-C in FIG. 3) was averaged and reported in Table S3 using only data from I1.

Tag-to-Tag Separation Statistics from Nine Multi-Scan Events

Table S3 showed data on nine different multi-scan events, five of which were summarized in the main text as Table 1 (unique cycle numbers reveal the correspondence). Observe that more data can come from one pore versus the other, or can be balanced in volume across both pores. One of the two scan directions will also produce more data than the other, and this appears to be device dependent and/or voltage-setting dependent. By example for pore 2 data, (iii) and (iv) were from one experiment that produced more data L-to-R than R-to-L, while (viii) and (ix) were from another experiment that produced more data R-to-L than L-to-R.

The pore-to-pore speed coefficient of variation (CV, equal to standard deviation divided by the mean) provides a metric that can be used to assess how reliable the distances estimates were, since its a measure of heterogeneity of motion from scan to scan. The pore-to-pore speed CV was high at 83% for the L-to-R scans and more reasonable at 20% for the R-to-L scans for event (i) (also event (i) in main text Table 1). As described in main text FIG. 3, only the shorter tag-pair distance estimates were available in $I_2$ for event (i), and so the second longer tag-pair spacing (B-C in FIG. 3) was averaged and reported in Table S3 using only data from I1.

Example 2: Automated Searching and Surveying for Map Generation of a Molecule

DNA methylation was of paramount importance for mammalian development and disease. In fact, deregulation of DNA methylation was a defining feature of virtually all cancer types. The most common methylation was at the fifth carbon of cytosines (5-methylcytosine (5mC)), and in eukaryotes was primarily found in the context of symmetrical CpG dinucleotides. Although mammals have roughly 5-fold fewer CpG dinucleotides than expected from the nucleotide composition of their genome, 70-80% of CpGs were methylated. The 5mC modification at CpGs was associated with transcriptional repression, and has been implicated in the epigenetic phenomena of genomic imprinting and X-chromosome inactivation. The modification 5-hydroxymethylcytosine (5hmC), second only to 5mC in frequency, plays an important role in cell differentiation, development, aging and neurological disorders, and whole-genome profiles of 5hmC provide robust diagnostic biomarkers in adult patients with cancer.

While the importance of 5mC and 5hmC in understanding development and disease was well recognized, in many contexts the precise roles these epigenetic modifications play are not fully understood. Standard tools (NGS, microarrays) are insufficient for detecting long-range changes in methylation, and time-resolved DNA methylation analysis is experimentally challenging in cost and time. Time-resolved processes of interest include: replication dependant methylation changes, time resolved mitotic and meiotic DNA methylation events, DNA changes induced by chemical exposure, as well as methylation and demethylation rates and processes associated with transcription and nucleosome assembly and remodelling. New tools are needed to efficiently and comprehensively monitor the dynamic processes of DNA methylation and demethylation, by tracking methylation states and their locations in DNA, and at single-molecule resolution.

The dual-pore approach as described in the present disclosure can perform genome-wide and multiplexed methylation analysis on longer reads (Mb) in >10× reduced time. Time reduction was due, in part, because the dual-pore can generate significantly higher methyl-site throughput per nanopore by removing the burden of ratcheting through each base. Specifically, a 1D nanopore sequencing read of 1 kb would comprise up to 100 CpG calls and take ~2 seconds (median ~450 bases/sec), while the dual-pore generates 100+ reads of 50 kb that comprises up to 500 CpG calls in less than 2 seconds (preliminary data). Time reduction was also possible because the dual-pore data computational requirements were lower than nanopore sequence assembly, as discussed in "5mC and 5hmC labeling methods as single-plex assays with model reagents on dual-pore instrumentation" Approach. Note that a 100 bp resolution was a byproduct of using 30 nm length pores, and thinner membranes (e.g., 10 nm for ~30 bp resolution) were explored to push spatial resolution limits with modest adjustment to the current fabrication process. Lastly, individual molecule-to-molecule differences can be deconvoluted through a multi-read dual-pore approach, while protein-pore sequencing was limited to 1D reads and so produces averaged CpG calls across a set of molecules at ~10 bp resolution. Optical mapping of long fragments (>100 kb) in nanochannels was a non-sequencing method that assays a motif (GCTCTTC) for genome mapping, primarily to scaffold contigs produced by assembly and to discover large (>500 bp) structural variants and inversions. Non-methylated CpGs were simultaneously assayed with a secondary fluorescent reporter. Although high throughput (3.2 Gb at 100× coverage/12 hours), the commercial price was high ($5 k/run) and CpG resolution was low (1 call/kb). The 100 bp resolution as described in the present disclosure falls in between the ~10 bp (nanopore sequencing) and ~1 kb (optical mapping) resolutions, which have separately provided valuable epigenetics insights. Thus, achieving high-accuracy CpG calls at ~100 bp resolution within long DNA provides an enabling epigenetics research tool.

The instrument as described in the present disclosure contains the following features:
1. Multiplexed analysis of 5mC and 5hmC;
2. Mapping the methylation state of CpGs at 100 bp resolution in long DNA reads (100 kb to 2 Mb);
3. High accuracy in CpG-state calling (>90%) and position mapping (10% error) within single molecules;
4. High throughput and cost effective-targeting 50× haploid genome coverage in 4 hours.

The technology enables single-molecule control and multi-read sensing, and has been applied to 50-150 kb DNA, and has shown accurate mapping of sequence-specific protein tags on the DNA. Preliminary data showed that 5mC-binding proteins were detectable during dual-pore scanning of 48 kb DNA, and the 50 kDa proteins and 150 kDa antibodies were differentially detectable, suggesting a path for multiplexing. Use of a barcode labeling can both identify DNA molecules and map the relative location of CpG-call sites in heterogeneous samples.

The dual-pore method provides reporting coarse methylation state and location in single long DNA molecules with unparalleled accuracy. The accuracy-enabling feature of the dual pore method was that, by using real-time feedback control logic, each molecule can be electrically scanned as many times as required to achieve the desired level of accuracy (preliminary data). The enabling access to global context was significant: up to 10,000 CpGs could be accessed in a single, continuous Mb-length DNA molecule. Additionally, by leveraging a silicon-based fabrication flow process, the devices can be made a wafer scale and in high volumes inexpensively, comprising a 50 dual-pore array.

Objective: Using a model methylatable sequence, establish 5mC and 5hmC protein-binding assays that can scale with the instrument, and establish assay efficiency and performance in terms of fractions (±CI) of molecules and sites per molecule that were correctly labeled, detected and mapped using dual-pore technology.

Background: A solid-state nanopore is a nano-scale hole formed in a membrane. DNA passing through the pore under an electric field produces a transient blockade in the trans-pore ionic current, containing information regarding the chemical and conformational state of the molecule. Solid-state pores can target a more diverse analyte pool than protein pores due to their larger size.

Preliminary Data: The dual nanopore platform solves the limitations of single-nanopore technology by enabling res-canning of each molecule to the required accuracy, for enhanced mapping of features. The dual-pore platform features an all-insulator, lithography-based construction with two solid-state nanopores 20 nm in diameter and spaced 500 nm apart, and with the capability of independent voltage-force biasing and current sensing at each pore. Using this platform dual-pore capture of λ-DNA was demonstrated. A Field Programmable Gate Array (FPGA) executes active-control logic to form a tug-of-war linearization on 75% of captured DNA molecules. The active-logic control was extended for bidirectional "rescanning" control (FIG. 9). In this approach, λ-DNA was labeled with mono-streptavidin (MS) protein tags incorporated at nick sites of Nt.BbvC1 nicking endonuclease. The labeled λ-DNA was then dual-captured in a tug-of-war state. The protein tags produce pronounced blockade "spikes" below the dsDNA blockade level. The FPGA implements bidirectional control that counts a set number of detectable tags through pore 2 (via current 12), then triggers a change in DNA direction by changing the net force bias (via voltage $V_1$ change) during sensing. In FIG. 9b, changes in direction occur when detecting 2 tags in $I_2$. 100s of such multi-scans were demonstrated, for varying tag detection numbers and spacing.

Mapping tag-to-tag distances was achieved by multiplying the mean tag-to-tag times by the mean tag velocity, which was computed by dividing the known distance between the pores by the tags time-of-flight from pore to pore. The genomic distance predictions give good agreement with the expected labeling spacing of this model system, including (301 bp, 323 bp, 614 bp, 915 bp) with divergence growing appreciably above 5 kb or 1.6 μm.

Synthesize a set of model reagents. (a) Created a 200 bp model comprising the promoter region of the TERT gene, upstream from the ATG of exon 1 with 21 CpGs, to explore a CpG spacing relevant for carcinogenesis. Created one unmethylated version, and four methylated versions: (i) only 3 CpGs spaced ~100 bp apart were 5mC; (ii) all CpGs were 5mC; (iii-iv) same as (i,ii) but with 5hmC instead of 5mC. (b) Ligated each 200 bp variant with 20 kb non-methylated DNA fragments at both ends (40.2 kb total), with symmetric detectable sequence-landmarks 500 bp outside both ends of the 200 bp models (1.2 kb between landmarks).

Metrics: Model 200 bp sequences and methylated variants can be commercially ordered (IDT). Ligated products were evaluated by gel electrophoresis and nanopore analysis with target yield of 95%.

Model oligonucleotide synthesis, duplex formation and evaluation. Complimentary 200 bp oligonucleotides containing the appropriate site-specific 5mC or 5hmC were chemically synthesized on each appropriate CpG for the model being synthesized, with 5' phosphate groups to prepare them for ligation.

Figure 15:
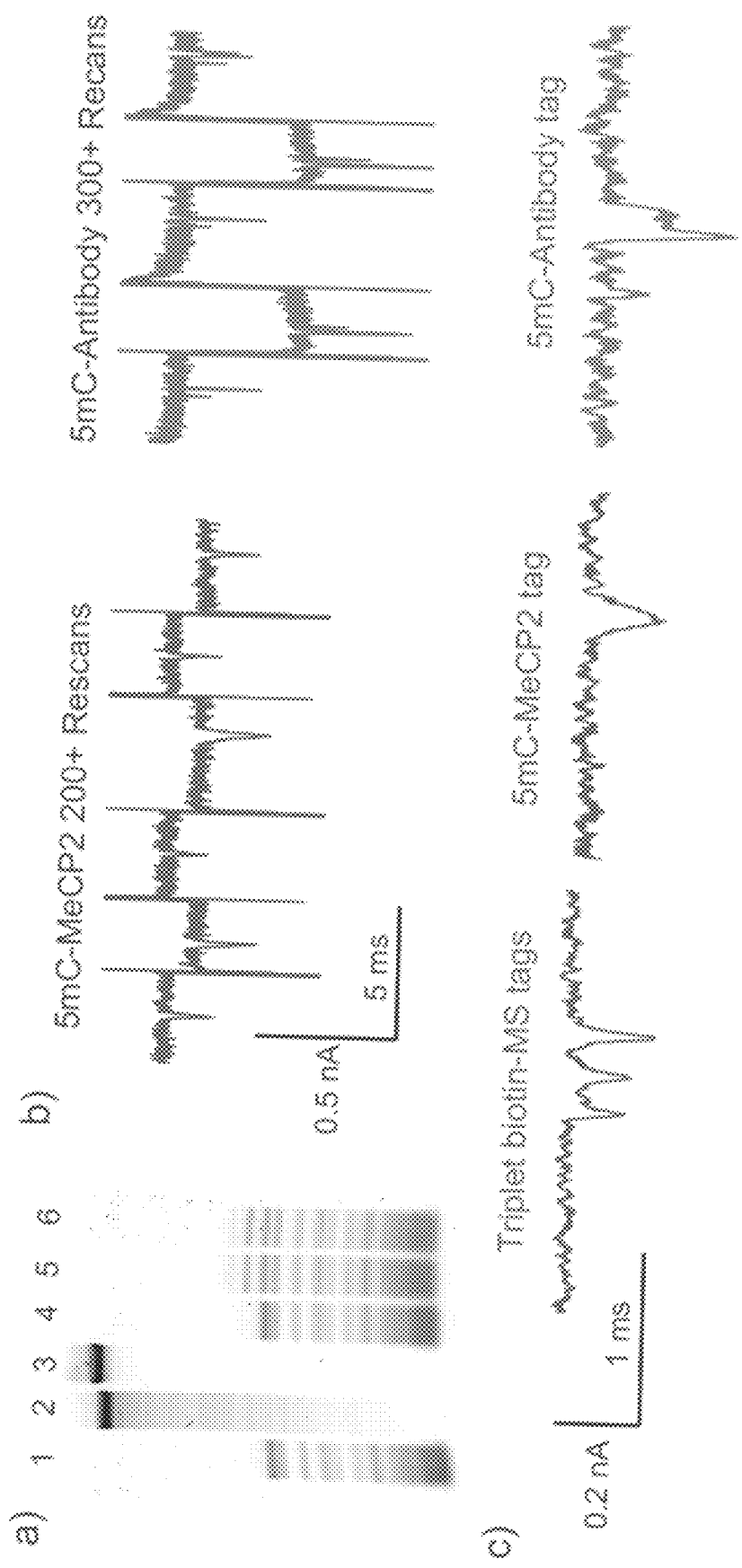
FIG. 15 depicts restriction enzyme analysis of methylated λ-DNA for 0, 30, 60 min incubation with HpaII (lanes 1-3) and MspI (lanes 4-6). (b) Dual-pore rescanning data for MeCP2 and Antibody bound to 5mC sites on lambda DNA with 100s of scans. (c) Comparing Tag signals for MS protein (3 tags spaced 301 bp, 323 bp) bound to biotin [19], versus MeCP2 and Antibody bound to 5mC. Proteins ~50 kDa in size produce similar blockades, while 150 kDa Antibody produces deeper blockades, which can be levered for multiplexing.

Evaluated annealed DNA oligonucleotides for cleavage by the methylation sensitive restriction enzyme HpaII, which was sensitive to methylation state, unlike MspI. DNA containing 5mC methylation at CpG sites were created using M.ssp1 methylase transferase. Results show that methylated lambda DNA was refractory to cleavage by HpaII as a function of methylation reaction time (FIG. 15*a*).

Production of long DNA dual-pore methylation constructs. Complementary oligonucleotides were annealed for each model by heating to 95° C. then cooling to 25° C. for 20 min. Oligonucleotides were A-tailed using Klenow polymerase and dATP. Blunt ended Lambda DNA fragments were prepared by restriction enzymes that cut Lambda only once and leave blunt ends. SnaB1, NaeI and Sfo1 produced blunt end fragments suitable for T-tailing. SnaB1 fragments were T-tailed using Terminal transferase and ddTTP. Annealed and tailed oligonucleotide duplexes were then ligated to 20 kb fragments using T4 DNA ligase at 12° C. for 12-18 hours.

Outcome and assessment. Only complementary T-A cloning ends will produce full-length molecules (40.2 kb). The amount of full-length molecules after the ligation period will indicate the efficiency. An alternative ligation strategy using the reverse transcriptase tailing method can be employed if efficiency was too low. Gel electrophoresis was used to assess efficiency, with the goal of 95% yield. Single nanopores can be used to assess DNA length with clear doubling of single molecule event duration for 40 kb vs. 20 kb.

5mC and 5hmC labeling methods as single-plex assays with model reagents on dual-pore instrumentation (4-10 months). (a) Used binding proteins and antibodies of varying sizes to establish nanopore differentiable detectability of each motif (b) Used sequence landmarks to trigger rescanning of the interior 200 bp methylatable region during dual-pore interrogation.

Metrics: 200 bp models were assessed by gel electrophoresis for methyl-binding, and should exceed 90% yield. Replicate dual-pore data (>10 experiments per reagent set) demonstrated interrogating 75% of molecules with at least 10 scans, and match confirmed methylation status with 95% CI; dual-pore mapping performance achieved 10% mean relative position-error per molecule. Biochemical measurement of 5mC and 5hmC interaction with binding proteins. To confirm stable and highly specific binding of antibodies and proteins electrophoretic mobility shift assays (EMSA) were conducted using the 200 bp model fragments. Binding protein titrations with duplex oligonucleotides was performed and assessed using native polyacrylamide gels. Methylation in ligated models using the South-Western technique was confirmed. In this technique, DNA was transferred to a nylon membrane and subsequently probed with antibodies specific for 5mC or 5hmC.

Preliminary Data: Dual-pore experiments with detection of 5mC antibody and protein binding. As proof of concept for the antibody based detection of 5mC, methylated Lambda DNA was incubated with a commercially available polyclonal antibody (Thermo Fisher Scientific PA1-30675). The antibody was bound to the DNA at low stoichiometry (1 ul of 1:50,000 dilution) ensuring a low binding frequency to methylated DNA. Binding reactions were tested directly in dual-pore tug of war and rescanning experiments (FIG. 15*b-c*), resulting in 55% of DNA with 1 or more detectable antibody tags, and 10% had 4 or more tags. These results demonstrate that the antibody tag was stably bound to DNA containing 5mC during dual-pore rescanning interrogation. Monoclonal antibodies directed against 5mC and 5hmC were expected to perform better than the polyclonal tested. To test the potential for nanopore differentiable detectability, MeCP2 methyl-binding protein was selected because it was smaller (50 kDa) than an antibody (150 kDa). Single pore work showed that this difference in size can be detected when bound to a DNA molecule, and others have tested MeCP2 bound to methylated CpG dinucleotides in short DNA. In a proof of concept, methylated DNA was bound to MeCP2 protein (1:50 stoichiometry) and tested on the dual-pore device. The results (FIG. 15*b-c*) give confidence that MeCP2 has a resolvable electronic signature, which was comparable to MS as a similar-sized protein, and demonstrating that proteins of different sizes bound to methylated CpGs on DNA can be electronically detected during dual-pore interrogation.

Dual-Pore Methods:

Devices were made using a known procedure. The 30 nm thick nitride membrane sets the spatial sensing footprint (~100 bp), and FIB milling produces ~20 nm diameter nanopores.

The dual-pore chip was mounted in a 3D printed flow-cell with access ports interfacing to the chip via O-ring seals. A dual-channel voltage-clamp amplifier (MultiClamp 700B, Molecular Devices) applies transmembrane voltages and measure ionic current (filter set at 30 kHz). A digitizer (Digidata 1440A, Molecular Devices) samples data at 250 kHz, and the amplifier was interfaced to the FPGA with control protocols described in programmed in Labview (NI PCIe-7851).

Electronic differentiation of 5hmC from 5mC using chemical tagging. The T4 phage enzyme T4 glucosyltransferase catalyzes the transfer of a glucose moiety from uridine diphosphoglucose (UDPG) to existing 5-hmC in DNA to form glucosyl-5-hydroxymethylcytosine (glucosyl-5-hmC). This enzyme does not modify cytosines or 5-mC and thus represents a method specific for the detection of 5hmC. A twostep labeling process was used in which a uridine analog containing an azide moiety (uridine diphosphate-6-azideglucose) was transferred to the hydroxl group of 5hmC (click chemistry). With this method, electronically detectable moieties containing alkenes can be attached, such as proteins, polyethylene glycols (PEG) and oligonucleotides. Using this labeling scheme, an electronically detectable tag was developed for 5hmC that was distinct from 5mC-tagged sites.

Data analysis methods: Developed algorithms for differential detection of antibody vs. protein and varying size PEG structures when bound to DNA. Principal component analysis and support vector machines were leveraged to automate, in a scalable fashion, the classification of nanopore event signatures based on training data and probabilistic models. Such methods were used to automate classification of the 5mC-tagged and 5hmC-tagged states.

Figure 4:
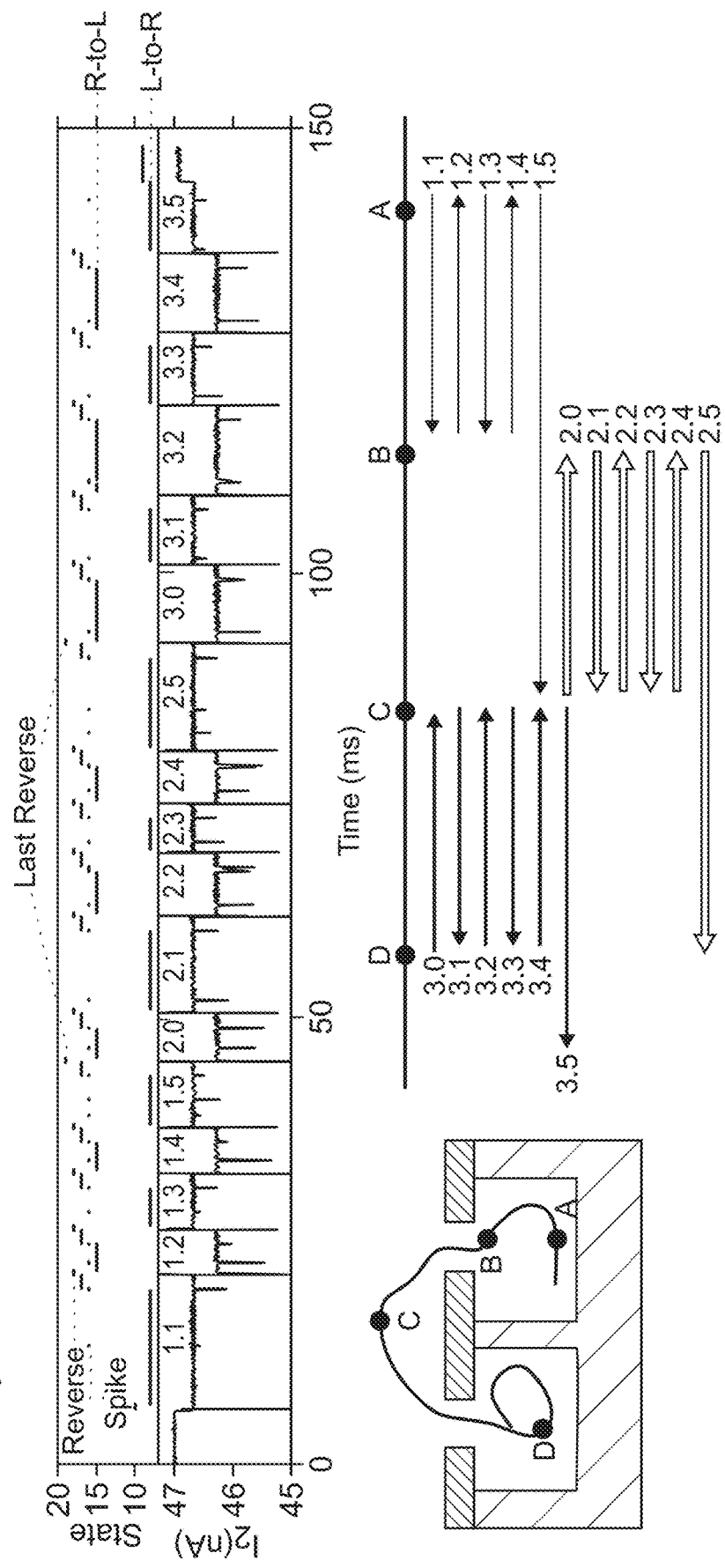
FIG. 4 depicts an example of reading a region of a tagged molecule and then panning/gliding the molecule to a different region for detection. The algorithm involved in the mapping one or more features of a molecule in this non-limiting example includes the following: (a) Initialize scan count=0; (b) The dual system initially detects $N_{tag}$ ($N_{tag}$=2 in this example) tags and starts flossing; (c) Increment scan count each time a new scan starts; (d) After a certain number of flossing scans $N_{scan}$ ($N_{scan}$=4 in this example), the system scans $N_{tag}$+1 tag for the next scan; (e) The system keeps flossing based on $N_{tag}$, Scan count restart from 0; (f) Repeat steps (b) to (e) until the molecule exits.
Figure 5:
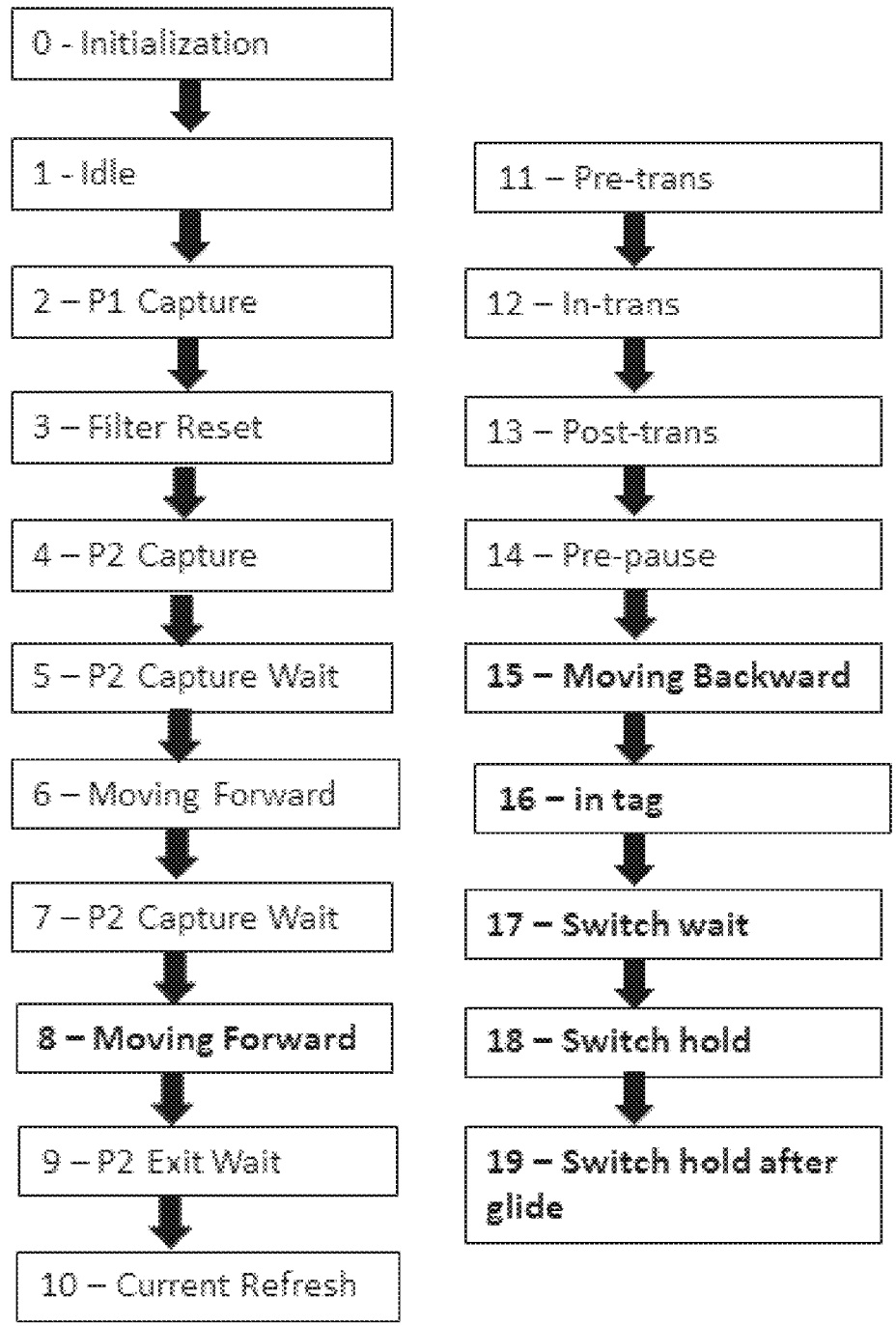
FIG. 5 depicts a flow chart of steps of the processor, highlighting steps 8, and 15-19 which are involved in rescan and gliding, where the states shown in bold text are the key states strongly related in rescan and gliding.
Figure 6:
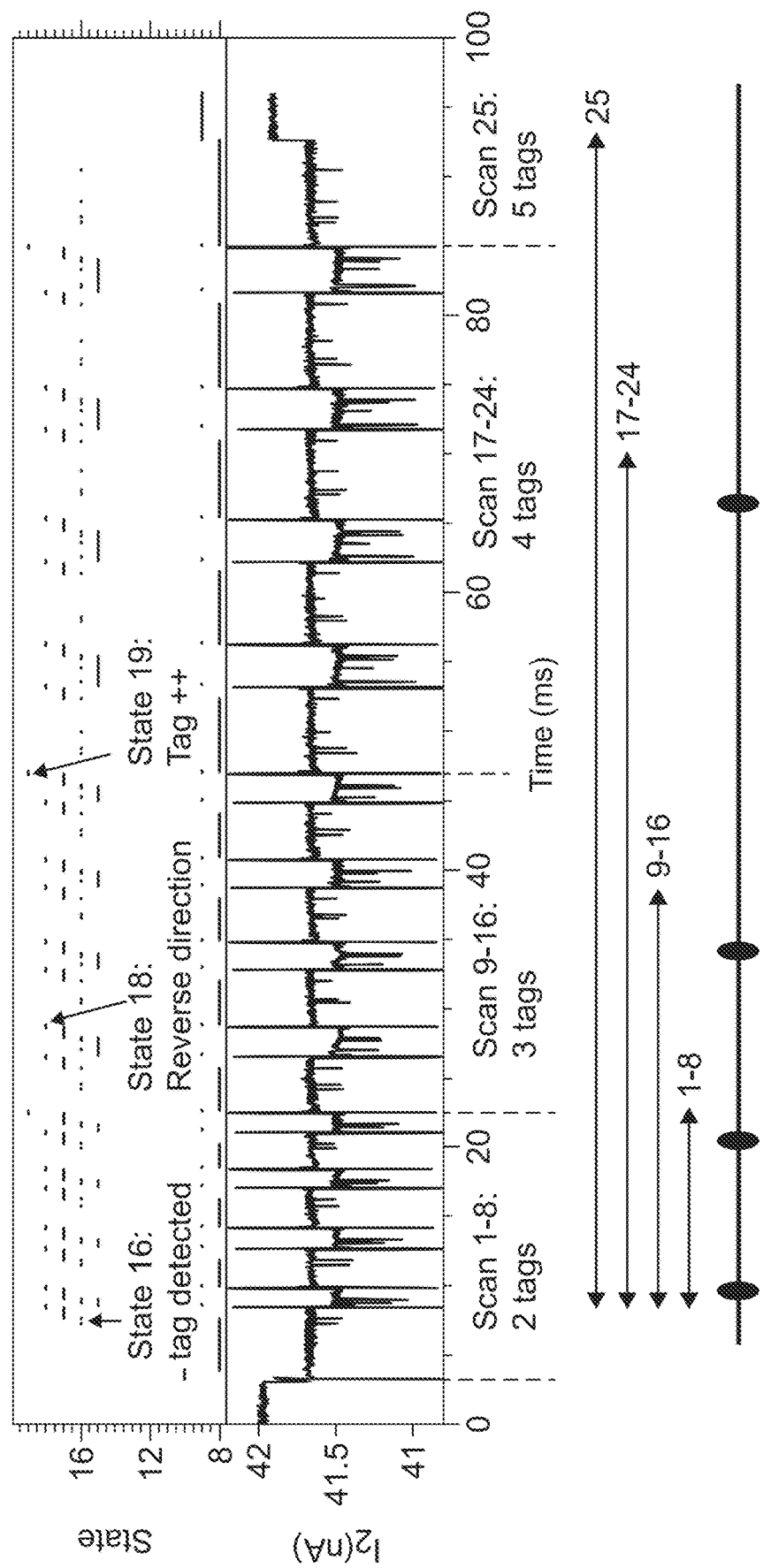
FIG. 6 depicts an example of a basic zoom that depicts bidirectional scanning and detection of multiple tags (e.g., multiple probes) on a biomolecule (DNA). The algorithm involved in the mapping of one or more features of a molecule in this non-limiting example includes the following: (a) Initialize scan count=0; (b) The dual system initially detects $N_{tag}$ ($N_{tag}$=2 in the example) tags and starts flossing; (c) Increment scan count each time a new scan starts; (d) After a certain number of flossing scans $N_{scan}$ ($N_{scan}$=4 in the example), the system increases the number of triggering tags $N_{tag}$=$N_{tag}$+1. Reset scan count to 0; (e) The system continue to floss based on new $N_{tag}$; and (0 Repeat steps (b) to (e) until the molecule exits.
Figure 7:
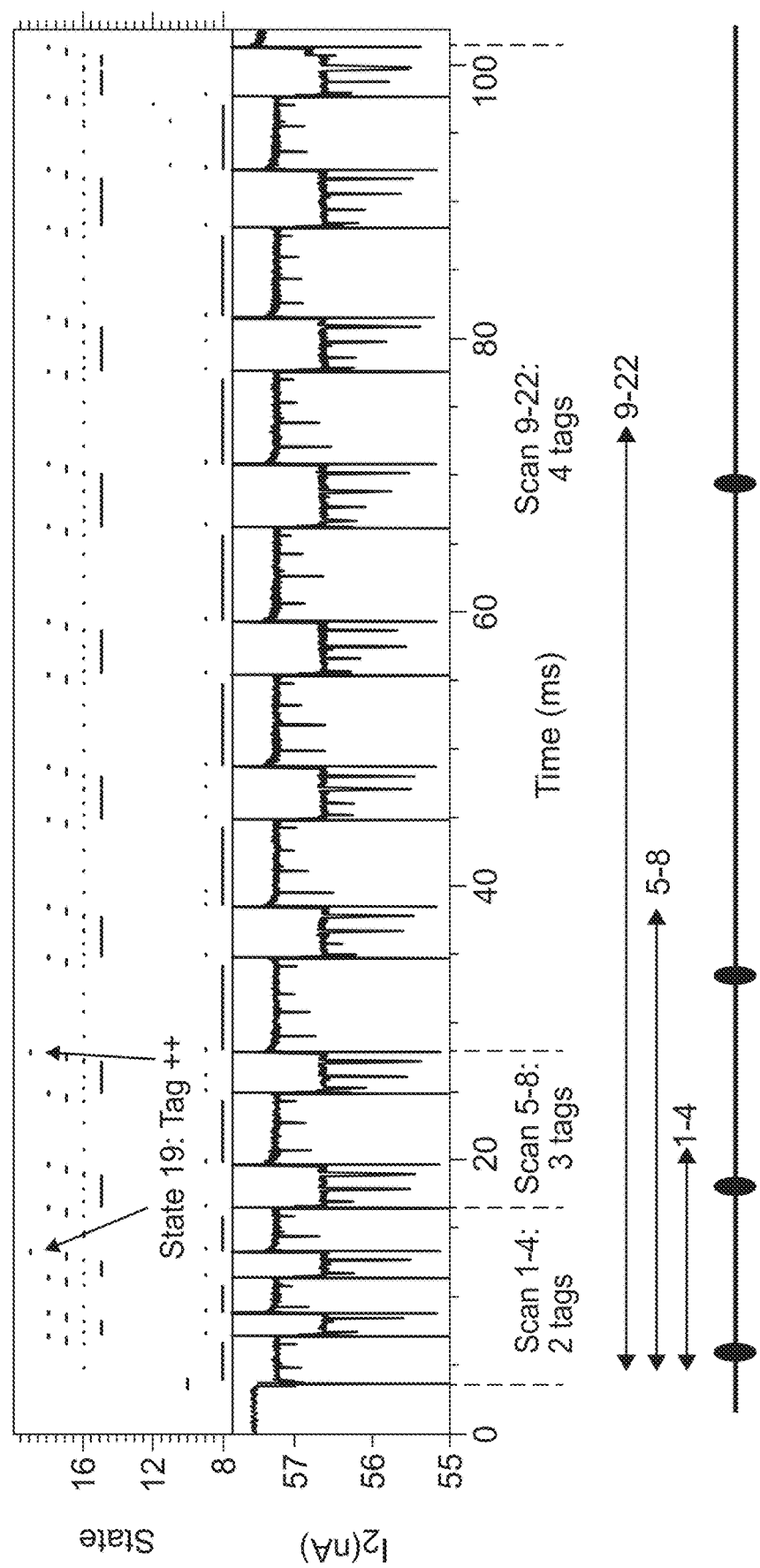
FIG. 7 depicts a non-limiting example of a terminated zoom with the following algorithm: (a) Initialize scan count=0; (b) The dual system initially detects $N_{tag}$ ($N_{tag}$=2 in the example) tags and starts flossing; (c) Increment scan count each time a new scan starts; (d) After a certain number of flossing scans $N_{scan}$ ($N_{scan}$=4 in the example), the system increases the number of triggering tags $N_{tag}$=$N_{tag}$+1. Reset scan count to 0; (e) The system continue to floss based on new $N_{tag}$; (f) Repeat steps (b) to (e) until $N_{tag}$ reaches to $N_{max}$ ($N_{max}$=4 in the example); (g) The system continue to floss based on $N_{max}$; (h) Stop incrementing scan count. Keep flossing based on $N_{max}$ until the molecule exits.

The experiments of "5mC and 5hmC labeling methods as single-plex assays with model reagents on dual-pore instrumentation" generated the necessary training data for model building, and cross validation sets for testing the performance of the method. Performance metrics included: model accuracy, false-positive/false-negative of molecule calls, fraction of CpGs correctly called per molecule, and CpG distance/mapping prediction performance. In single-plex form, the dual-pore Yes/No CpG-state call looks only for a baseline shift that signals the presence of a protein bound to a methylated CpG site within the 100 bp sensing footprint. In multiplex form, the algorithms were used for differential detection. When the 200 bp model was CpG methylated at 100 bp intervals, the data was anticipated to be in its simplest form for analysis. Since the tags were 100 bp apart instead of 300 bp, the triplet tag blockade will appear more condensed. The approach to ensuring these blockades remain resolvable (i.e., as 3 distinct downward spikes) has two parts: 1) use higher bandwidth (FIG. 4 showed 10 kHz, and also 30 kHz) for faster temporal response in the nanopore signal—this will give faster rise/fall response; and 2) slow the DNA speed down using tug-of-war voltages, as described in [18-19]—when the voltages come into force balance, the DNA motion becomes more random and the molecule slows up to 1000×. Using voltages below the force balance value ensure DNA motion was directionally uniform (i.e., avoid motion jitter), but close enough to that value to ensure clear CpG-tag blockade resolution for the 3 tag model reagents. In the same experiment, after voltages were identified to resolve the 3 CpG tag models, the fully methylated models will be explored (21 CpGs over 200 bp, FIG. 3). These will generate a distribution of (finite) permutations of CpG-tagged profiles that were distinct from the 3-tag control models with CpG-tags 100 bp apart. Specifically, 2 tags spaced less than ~100 bp apart will be present simultaneously present in nanopore, given the nanopore length of 30 nm. Machine learning algorithms were leveraged to classify the resulting compound signals with the aim of resolving tag density and inter-tag distance. However, success of the Aim does not depend on such deconvolution. An objective in this example was to correctly call 5mC and, differentially, 5hmC CpG sites within 100 bp "segment" sizes. Subtler features can be also mined from the fully methylated data, being empowered by the many-read feature of the dual-pore rescanning function.

Outcome and Assessment. The preliminary data demonstrated that antibodies bound to 5mC were detected and provided substantial confidence in the proposed strategy of using antibodies that target 5mC and 5hmC sites present in the 200 bp TERT promoter models outlined in Aim1. Generally, larger binding molecules will give rise to larger signals, while smaller binding molecules (either bound or chemically attached) will give smaller and distinct signals. Major expected outcomes of specific "5mC and 5hmC labeling methods as single-plex assays with model reagents on dual-pore instrumentation" were 1) Biochemical methods for the attachment of electronically detectable tags to both 5mC and 5hmC, and 2) tags that generate electronic signatures that distinguish between 5mC and 5hmC (albeit in distinct molecules).

Simultaneous 5mC and 5hmC detection and mapping using dual-pore instrumentation. Examined equal (1:1) and limiting (9:1) mixtures of 5mC:5hmC positive reagents, and with unmethylated background. Metrics: Replicate dualpore data (>10 experiments per reagent set) should match proportional confirmed methylation status and ratios of each reagent with 2% mean absolute call-error across replicates (e.g., 50% unmethylated, 5% 5hmC, 45% 5mC mixture=48-52% unmethylated, 3-7% 5hmC, 43-47% 5mC) with 95% CI, while recapitulating mapping performance of "5mC and 5hmC labeling methods as single-plex assays with model reagents on dual-pore instrumentation" for each molecule with 10 or more scans. Dual pore discrimination of 5mC and 5hmC on long DNA molecules. In Specific "Simultaneous 5mC and 5hmC detection and mapping using dual-pore instrumentation", the basis for multiplex assay was established to detect 5mC and 5hmC with single molecule precision. Initially 1:1 mixtures of model substrates were tested that were tagged either for 5mC or 5hmC using electronically distinct tags using ~100 bp spacing (previously described "Synthesize a set of model reagents"). Relative detection of 5hmC in a background of 5mC. In human genomes, about 4% of cytosines were methylated, and most of these were present at CG dinucleotide sequences. In contrast, the presence of 5hmC was an order of magnitude lower. This distribution was emulated by serial dilution 5hmC tagged DNA into 5mC tagged DNA at 1:5, 1:10 and 1:100 dilutions. The mixtures were measured on the dual nanopore device, and fractional predictions of 5hmC vs. 5mC and were compared to the known rations, leveraging logic.

Outcome and Assessment. Clearly identified populations of molecules tagged with 5mC and those tagged with 5hmC.

Developed (I) prototype chips, housings and instrumentation with arrayed dual-pore functionality, and molecular barcoding schemes to identify long DNA from a mixture for higher throughput analysis; (II) enhanced multiplexed analysis of both 5mC and 5hmC within single molecules; and (III) algorithms that explore efficient probabilistic methylation assignments, with the aim of achieving greater levels of accuracy. Instrument feature #4 pursued targeted 50× haploid genome coverage in 4 hours. In terms of coverage and time, extrapolating the 100× per 50 kb every 2 seconds per dual-pore shown and considering a new molecule was captured every 10 seconds, that's 3.2 Gb at 100× in 64 min.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for partially or fully recapturing a polynucleotide in a nanopore device that was previously captured, the method comprising:
   a) providing a device with at least one nanopore, the device comprising:
      (i) a first pore positioned between, and fluidically connecting, a chamber and a first fluidic volume, the first fluidic volume being a geometrically constrained enclosure,
      (ii) the first fluidic volume comprising an inlet and an outlet for fluidic filling and electrode access, wherein the first pore is connected to the first fluidic volume in a location in between the inlet and outlet,
      (iii) at least one electrode positioned within the first fluidic volume, and at least one electrode positioned within the chamber,
      (iv) a sensor configured to provide:
         a voltage between the electrode within the first fluidic volume and the electrode within the chamber, and
         a current measurement that detects capture and translocation of the polynucleotide into and through the first pore;
   b) loading the polynucleotide into the chamber of the device;
   c) applying a first voltage to capture and translocate the polynucleotide from the chamber through the first pore and into the first fluidic volume;
   d) detecting in a first sensor current when the polynucleotide has translocated through the first pore;
   e) applying a second voltage equal to zero mV for a time period while the polynucleotide is contained within the first fluidic volume;
   f) applying a third voltage to recapture and partially or fully translocate the polynucleotide from the first fluidic volume through the first pore and into the chamber; and
   g) detecting in the first sensor current when the polynucleotide has partially or fully translocated through the first pore.

2. The method of claim 1, wherein the first fluidic volume is a fluidic channel having a depth of at least 0.5 microns.

3. The method of claim 1, wherein the detecting in step (d) that the polynucleotide was captured and translocated through the first pore at the first voltage, wherein the first voltage is maintained for a time period ranging from 30 ms to 500 ms.

4. The method of claim 1, wherein the second voltage equal to zero in step (e) is maintained for a time period ranging from 10 ms to 5 sec.

5. The method of claim 4, wherein the second voltage equal to zero in step (e) is maintained for a time sufficient to allow the molecule to entropically relax to an equilibrium configuration.

6. The method of claim 1, wherein in step (e) the end of the polynucleotide closest to the at least first pore is positioned away from the at least first pore at a distance of up to 5 millimeters.

7. The method of claim 1, wherein the nanopore device further comprises a second pore, between, and fluidically connecting, the chamber and a second fluidic volume, the second fluidic volume being a geometrically constrained enclosure with a second inlet and a second outlet, and the second pore is fluidically connected to the second fluidic volume between the inlet and the outlet.

8. The method of claim 1, wherein the at least one electrode positioned within the second fluidic volume, and at least one electrode positioned within the chamber, enable a sensor configured to provide a voltage between the electrode within the second fluidic volume and the electrode within the chamber, and a current measurement that detects capture and translocation of a polynucleotide into and through the second pore.

9. A method for mapping one or more features of a target polynucleotide, the method comprising the steps of: a) providing a device for controlling the movement of the target polynucleotide through a first and second pore simultaneously, the device comprising: (i) a first pore positioned between, and fluidically connecting, a chamber and a first fluidic volume, the first fluidic volume being a geometrically constrained enclosure, (ii) a second pore positioned between, and fluidically connecting, the chamber and a second fluidic volume, the second fluidic volume being a geometrically constrained enclosure; (iii) the first fluidic volume and the second fluidic volume, each comprising an inlet and an outlet for fluidic filling and electrode access, wherein the first pore is connected to the geometrically constrained enclosure of the first fluidic volume in a location in between the inlet and outlet, and wherein the second pore is connected to the geometrically constrained enclosure of the second fluidic volume in a location in between the inlet and outlet, (iv) at least one electrode positioned within the first fluidic volume, at least one electrode positioned within the second fluidic volume, and at least one electrode positioned within the chamber, (v) a sensor configured to provide: a voltage between the said electrode within the first fluidic volume and said electrode within the chamber; and a voltage between the said electrode within the second fluidic volume and said electrode within the chamber, and a current measurement that detects capture and partial or full translocation of the polynucleotide into and through the first pore; and a current measurement that detects capture and partial or full translocation of the polynucleotide into and through the second pore; b) loading the target polynucleotide into the first fluid volume of the device; c) applying a first voltage at the first pore to capture and translocate a first portion of the target polynucleotide from the first fluid volume, through the first pore and into the chamber; d) detecting with the current measurement the capture and translocation of the first portion of the polynucleotide into and through the first pore and into the chamber; e) applying a second voltage at the first pore and a second voltage at the second pore to capture and translocate the first portion of the target polynucleotide from the chamber through the second pore and into the second fluidic volume by the second pore while a separate portion of the target nucleotide remains in the first pore; f) detecting with the current measurement the capture and translocation of the first portion of the polynucleotide into and through the second pore and into the second fluid chamber; g) applying a third voltage at the first pore and a third voltage at the second pore to control a direction of motion of the target polynucleotide through the first pore and the second pore; h) detecting in the current measurement of the first pore a set of features on the polynucleotide; as each feature passes through the first pore, and detecting in the current measurement of the second pore the same set of features on the polynucleotide as each feature passes through the second pore; and i) applying a fourth voltage at the first pore and a fourth voltage at the second pore to reverse the direction of motion of the target polynucleotide through the first pore and the second pore.

10. The method of claim 9, wherein the third voltage at the second pore in step (g) is greater in magnitude than the third voltage at the first pore so that the direction of motion of the target polynucleotide through the first pore is from the first fluid volume and into the chamber, and the direction of motion of the target polynucleotide through the second pore is from the chamber and into the second fluid volume.

11. The method of claim 10, wherein in step (h) detecting in the current measurement of the first pore the set of features on the polynucleotide as each feature passes through the first pore occurs in time before detecting in the current measurement of the second pore the same set of features on the polynucleotide as each feature passes through the second pore.

12. The method of claim 9, wherein the fourth voltage at the first pore in step (i) is greater in magnitude than the fourth voltage at the second pore so that the direction of motion of the target polynucleotide is reversed compared to the voltage in step (g).

13. The method of claim 7, wherein the reverse in direction of motion in step (i) occurs after a predetermined number of features are detected in the measured current of the first pore or the second pore in step (h).

14. The method of claim 11, wherein the set of features detected in the first pore or in the second pore in step (h) are detected again and in reverse order after step (i).

15. The method of claim 14, wherein a return to step (g) occurs after a predetermined number of features are detected again in the measured current of the first pore or the second pore.

16. The method of claim 15, wherein the predetermined of features is increased to increase the length of the target polynucleotide that moves through the pores, in either direction.

17. The method of claim 9, wherein the method further comprises computing, with a processor: (a) the speed of a feature of the polynucleotide, from the time period between detection of the features in the first pore and the second pore, and the known distance between the first pore and the second pore; and/or (b) the distances between adjacent features of the set of features, by using the computed speed of at least one of these features or other features of the same polynucleotide, and integrating the speed profile over the time period between the adjacent features of the set of features as detected in the current measurement of the first pore or the second pore, or both.

18. The method of claim 10, wherein the method further comprises controlling, with a controller, the:
    a) number of features to scan for;
    b) number of features to re-scan;
    c) type of features to scan or re-scan for;
    d) number of cycles to scan or re-scan for;
    e) movement of the target polynucleotide;
    f) direction of the target polynucleotide;
    g) speed of the target polynucleotide; or
    h) a combination thereof.

19. The method of claim 15, wherein the method further comprises repeating steps g) through i), and with detecting the set of features in the first pore or in the second pore in reverse order after step i) prior to returning to step g), until the target polynucleotide exits the first pore and the second pore.

20. The method of claim 1, wherein the first voltage creates a voltage gradient across the first pore and along the length of the first fluidic volume and up to the inlet and to the outlet of the first fluidic volume.

21. The method of claim 1, wherein the first voltage creates voltage gradient across the first pore and along the length of the first fluidic volume and up to the inlet and to the outlet of the first fluidic volume.

22. A method for fully capturing, partially recapturing and then mapping one or more features of a target polynucleotide, the method comprising the steps of:
    a) providing a device for controlling the movement of the target polynucleotide through a first and second pore simultaneously, the device comprising:
        (i) a first pore positioned between, and fluidically connecting, a chamber and a first fluidic volume, the first fluidic volume being a geometrically constrained enclosure,
        (ii) a second pore positioned between, and fluidically connecting, the chamber and a second fluidic volume, the second fluidic volume being a geometrically constrained enclosure,
        (iii) the first fluidic volume and the second fluidic volume, each comprising an inlet and an outlet for fluidic filling and electrode access, wherein the first pore is connected to the geometrically constrained enclosure of the first fluidic volume in a location in between the inlet and outlet, and wherein the second pore is connected to the geometrically constrained enclosure of the second fluidic volume in a location in between the inlet and outlet,
        (iv) at least one electrode positioned within the first fluidic volume, at least one electrode positioned within the second fluidic volume, and at least one electrode positioned within the chamber, (v) a sensor configured to provide:
- a voltage between the said electrode within the first fluidic volume and said electrode within the chamber; and
- a voltage between the said electrode within the second fluidic volume and said electrode within the chamber; and
- a current measurement that detects capture and partial or full translocation of the polynucleotide into and through the first pore; and
- a current measurement that detects capture and partial or full translocation of the polynucleotide into and through the second pore;

b) loading the target polynucleotide into the chamber of the device;

c) applying a first voltage to capture and translocate the polynucleotide from the chamber through the first pore and into the first fluidic volume;

d) detecting in a first sensor current when the polynucleotide has translocated through the first pore;

e) applying a second voltage equal to zero mV for a time period while the polynucleotide is contained within the first fluidic volume;

f) applying a third voltage at the first pore to capture and translocate a first portion of the target polynucleotide from the first fluid volume, through the first pore and into the chamber;

g) detecting in a first sensor current the capture and translocation of the first portion of the polynucleotide into and through the first pore and into the chamber;

h) applying a fourth voltage at the first pore and a fourth voltage at the second to capture and translocate the first portion of the target polynucleotide from the chamber through the second pore and into the second fluid volume, while a separate portion of the target polynucleotide remains in the first pore;

i) detecting in a second sensor current the capture and translocation of the first portion of the polynucleotide into and through the second pore and into the second fluid chamber;

j) applying a fifth voltage at the first pore and a fifth voltage at the second pore to control the direction of motion of the target polynucleotide through the first pore and the second pore;

k) detecting in a first sensor current a set of features on the target polynucleotide as each feature passes through the first pore, and detecting in a second sensor current the same set of features on the target polynucleotide as each feature passes through the second pore; and l) applying a sixth voltage at the first pore and a sixth voltage at the second pore to reverse the direction of motion of the target polynucleotide through the first pore and the second pore.

* * * * *

SEQUENCE LISTING

```
<160> NUMBER OF SEQ ID NOS: 1

<210> SEQ ID NO 1
<211> LENGTH: 90
<212> TYPE: DNA
<213> ORGANISM: Artificial Sequence
<220> FEATURE:
<223> OTHER INFORMATION: Synthetic sequence

<400> SEQUENCE: 1
aaaaaaaaaa gggaaaggga aagggaaaga aaaaaaaaaa aaaaaaaaag ggaaagggaa      60
aaaaaaaaga gagagagaga gagagaagag                                       90
```